US007541383B2

(12) United States Patent
Fu et al.

(10) Patent No.: US 7,541,383 B2
(45) Date of Patent: Jun. 2, 2009

(54) ASTHMA AND ALLERGIC INFLAMMATION MODULATORS

(75) Inventors: Zice Fu, Burlingame, CA (US); Xi Alan Huang, San Mateo, CA (US); Jiwen Liu, Foster City, CA (US); Julio C. Medina, San Carlos, CA (US); Michael J. Schmitt, San Francisco, CA (US); H. Lucy Tang, San Francisco, CA (US); Yingcai Wang, Fremont, CA (US); Qingge Xu, Burlingame, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/986,863

(22) Filed: Nov. 26, 2007

(65) Prior Publication Data

US 2008/0085891 A1 Apr. 10, 2008

Related U.S. Application Data

(62) Division of application No. 10/742,281, filed on Dec. 19, 2003, now Pat. No. 7,321,001.

(60) Provisional application No. 60/435,366, filed on Dec. 20, 2002.

(51) Int. Cl.
*A61K 31/18* (2006.01)
*C07C 31/30* (2006.01)

(52) U.S. Cl. .................. 514/602; 514/562; 514/604; 514/605; 562/430; 564/83; 564/92; 564/97; 564/99

(58) Field of Classification Search .................. 514/562, 514/602, 604, 605; 562/430; 564/83, 92, 564/97, 99
See application file for complete search history.

(56) References Cited

U.S. PATENT DOCUMENTS

| 5,545,669 | A | * | 8/1996 | Adams et al. ............... 514/562 |
| 5,962,682 | A | | 10/1999 | Breu et al. |
| 6,008,234 | A | | 12/1999 | Kochanny et al. |
| 6,133,442 | A | | 10/2000 | Breu et al. |
| 6,531,291 | B1 | | 3/2003 | Kabbash et al. |
| 2002/0022218 | A1 | | 2/2002 | Li et al. |

FOREIGN PATENT DOCUMENTS

| EP | 0284202 | 9/1988 |
| EP | 0930528 | 7/1999 |
| EP | 0947500 | 10/1999 |
| EP | 1170594 | 1/2002 |
| GB | 2 388 540 | 11/2003 |
| WO | WO 95/01326 | 1/1995 |
| WO | WO 95/33461 | 12/1995 |
| WO | WO 96/19455 | 6/1996 |
| WO | WO 98/11094 | 3/1998 |
| WO | WO 99/55663 | 11/1999 |
| WO | WO 00/17204 | 3/2000 |
| WO | WO 00/40561 | 7/2000 |
| WO | WO 00/53573 | 9/2000 |
| WO | WO 01/14882 | 3/2001 |
| WO | WO 01/79169 | 10/2001 |
| WO | WO 01/94309 | 12/2001 |
| WO | WO 02/45718 | 6/2002 |
| WO | WO 02/094830 | 11/2002 |
| WO | WO 03/016254 | 2/2003 |
| WO | WO 03/066046 | 8/2003 |
| WO | WO 03/066047 | 8/2003 |
| WO | WO 03/078409 | 9/2003 |
| WO | WO 03/097042 | 11/2003 |
| WO | WO 03/097598 | 11/2003 |
| WO | WO 03/101961 | 12/2003 |
| WO | WO 03/101981 | 12/2003 |

OTHER PUBLICATIONS

Cosmi et al., "Chemoattractant Receptors Expressed on Type 3 T Cells and Their Role in Disease," Int. Arch. Allergy Immunol., 125:273-279 (2001).
Fujitani et al., "Pronounced Eosinophilic Lung Inflammation and Th2 Cytokine Release in Human Lipocalin-Type Prostaglandin D Synthase Transgenic Mice," J. Immunol., 168:443-449 (2002).
Hirai et al., "Prostaglandin D2 Selectively Induces Chemotaxis in T Helper Type 2 Cells, Eosinophils, and Basophils via Seven-Transmembrane Receptor CRTH2," J. Exp. Med., 193(2):255-261 (2001).
Iwasaki et al., "Association of a New-Type Prostaglandin D2 Receptor CRTH2 with Circulating T Helper 2 Cells in Patients with Atoipic Dermatitis," J. Investigative Dermatology, 119(3):609-616 (2002).
Matsuoka et al., "Prostaglandin D2 as a Mediator of Allergic Asthma," Science, 287(17):2013-2017 (2000).
Monneret et al., "Prostaglandin D2 is a Potent Chemoattractant for Human Eosinophils that Act via a Novel DP Receptor," J. Exp. Med., 193(2):255-261 (2001).
Munns et al., "Contribution of Type 27 II PLA2 to Prostaglandin Formation: A Study Using a Type II PLA2 Specific Inhibitor SB 203347," Prostaglandins & Other Lipid Mediators 57:5,6):361-370 (1999).
Romagnani et al., "Cytokines and Chemoattractants in Allergic Inflammation," Molecular Immunology, 38:881-885 (2001).
Saito et al., "Prostaglandin D2 and Reproduction," Am. J. of Reproductive Immunology, 47:295-302 (2002).

* cited by examiner

*Primary Examiner*—Rei-Tsang Shiao
*Assistant Examiner*—Janet L Coppins
(74) *Attorney, Agent, or Firm*—Jones Day

(57) ABSTRACT

Compounds, pharmaceutical compositions and methods are provided that are useful in the treatment of inflammatory and immune-related diseases and conditions. In particular, the invention provides compounds which modulate the function and/or expression of proteins involved in atopic diseases, inflammatory conditions and cancer. The subject compounds are carboxylic acid derivatives.

24 Claims, No Drawings

ASTHMA AND ALLERGIC INFLAMMATION MODULATORS

This application is a divisional of U.S. application Ser. No. 10/742,281, filed Dec. 19, 2003, now U.S. Pat. No. 7,321,001 which claims the benefit under 35 U.S.C. § 119 of U.S. provisional application No. 60/435,366, filed Dec. 20, 2002 the contents of which are hereby incorporated by reference in their entirety.

BACKGROUND OF THE INVENTION

G-protein coupled receptors play important roles in diverse signaling processes, including those involved in host defense mechanisms. Immune responses to infectious diseases, injury, tumors and organ transplantation and in diseases and conditions such as asthma, allergy, rheumatoid arthritis and neoplasia have been linked to GPCR regulation. Exaggerated or misdirected immune responses are responsible for many inflammatory and hypersensitivity diseases which, left untreated, can result in tissue or organ damage, pain and/or loss of function. Tissue inflammation is largely implicated in the pathogenesis of such diseases, of which asthma and allergic diseases are among the most well characterized. The mechanisms underlying airway inflammation and hyperreactivity are similar to those underlying allergic inflammation in other tissues, such as the skin and gut.

Prostaglandins are lipid-derived inflammatory mediators that recruit macrophages, T cells, eosinophils, basophils and neutrophils from peripheral blood to damaged or inflamed tissues. In addition, prostaglandins can, depending on the target cell type, induce or inhibit intracellular $Ca^{2+}$ mobilization, cAMP production, platelet aggregation, leukocyte aggregation, T cell proliferation, lymphocyte migration, and Th2 cell chemotaxis, IL-1a and IL-2 secretion and vascular and non-vascular smooth muscle contraction in responsive cells. Prostaglandins have been implicated in fever, various allergic diseases, vascular and non-vascular smooth muscle relaxation, pain perception, sleep, platelet aggregation and reproductive processes. Prostaglandins exert their effects by interacting with specific GPCRs.

Prostaglandin $D_2$ ($PGD_2$) is the major inflammatory mediator released by activated mast cells, typically found near skin surfaces, mucous membranes and blood vessels, upon immunological challenge (Lewis et al. (1982) *J. Immunol.* 129:1627-1631). During asthma and allergic responses, $PGD_2$ is released in large amounts. The role of $PGD_2$ in the initiation and maintenance of allergic inflammation has been well established in mouse models of asthma. For example, it has been demonstrated that overproduction of $PGD_2$ in vivo by $PGD_2$ synthase exacerbates airway inflammation in a mouse model of asthma (Fujitani et al. (2002) *J. Immunol.* 168:443-449).

A $PGD_2$-selective receptor, designated DP, has been identified (Boie et al. (1995) *J. Biol. Chem.* 270:18910-18916). In humans, DP is expressed in smooth muscle, platelets, small intestine and brain, and its expression in lung epithelium is induced by allergic challenge. Receptor activation induces cAMP production and intracellular $Ca^{2+}$ mobilization, and is believed to inhibit platelet aggregation and cell migration and induce relaxation of various smooth muscles. DP is coupled primarily to Gαs protein.

Significantly, in an OVA induced asthma model, $DP^{-/-}$ mice exhibited reduced asthma symptoms, e.g., reduced cellular infiltration of eosinophils and lymphocytes in BAL fluid, reduced Th2 cytokine levels in BAL fluid and reduced airway hyperreactivity to acetylcholine (Matsuoka et al. (2002) *Science* 287:2013-2019). The increased cellular infiltration in lung tissue and mucus secretion by airway epithelial cells characteristic of asthma in humans and observed in wild-type mice was not observed in DP-deficient mice.

Recently, an additional $PGD_2$-selective receptor, designated chemoattractant receptor-homologous molecule expressed on Th2 cells, or CRTH2, has been identified (Hirai et al. (2001) *J. Exp. Med.* 193(2):255-261). The receptor was previously referred to as GPR44 or DL1R. Among peripheral blood T lymphocytes, human CRTH2 is selectively expressed on Th2 cells, and is highly expressed on cell types associated with allergic inflammation such as eosinophils, basophils and Th2 cells. It has been shown that CRTH2 activation induces intracellular $Ca^{2+}$ mobilization and infiltration of Th2 cells, eosinophils and basophils.

Protein sequence analysis indicates that CRTH2 has no significant homology to DP, but rather, is related to members of the N-formyl peptide receptor (FPR) subfamily (Nagata et al. (1999) *J. Immunol.* 162:1278-1286). In contrast to DP, CRTH2 has been shown to couple primarily to Gαi protein.

These observations suggest that CRTH2 and DP may function independently to regulate aspects of allergic inflammation.

The increasing incidence of asthma, allergic diseases and immunologic diseases worldwide underscores the need for new therapies to effectively treat or prevent these diseases. The discovery of small molecules that modulate CRTH2 and/or one or more other $PGD_2$ receptors, e.g., DP, is useful for the study of physiological processes mediated by CRTH2 and/or one or more other $PGD_2$ receptors, e.g., DP, and the development of therapeutic agents for asthma, allergic diseases and other immunologic diseases. Novel compounds which display such desirable activity are described herein.

SUMMARY OF THE INVENTION

The invention provides compounds, pharmaceutical compositions and methods useful for treating or preventing conditions and disorders associated with inflammation processes. In particular, the invention provides compounds, pharmaceutical compositions and methods useful for treating or preventing asthma, allergic diseases, inflammatory conditions, cancer and viral infection.

The compounds of the invention have the general formula (I):

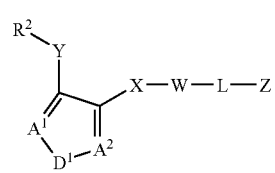

wherein
A¹ is C(R³) or N;
A² is C(R⁶) or N;
when A¹ is C(R³) and A² is C(R⁶), D¹ is selected from the group consisting of C(R⁴)=C(R⁵), C(R⁴)=N, NR⁷, O and S;
when A¹ or A² is N, D¹ is C(R⁴)=C(R⁵) or C(R⁴)=N;
W is a divalent group selected from the group consisting of a single bond, an aromatic ring, a heteroaromatic ring, a cyclo($C_3$-$C_8$)alkane ring and a heterocyclo($C_3$-$C_8$)alkane ring;

optionally, W is combined with $A^2$ to form a 5-, 6-, 7- or 8-membered fused ring containing from 0 to 3 heteroatoms selected from the group consisting of N, O and S;

X is a divalent linkage selected from the group consisting of —O—, —S(O)$_k$—, —CR$^a$R$^b$—, —C(O), —NR$^8$— and —C(NR$^9$)—;

Y is a divalent linkage selected from the group consisting of a single bond, —S(O)$_k$NR$^{10}$—, —C(O)NR$^{10}$—, (C$_1$-C$_4$)alkylene, hetero(C$_2$-C$_4$)alkylene, —N(R$^{11}$)C(O)NR$^{10}$—, —N(R$^{11}$)S(O)$_k$NR$^{10}$—, —N(R$^{11}$)CO$_2$—, —NR$^{11}$—, —O— and —S(O)$_k$—;

optionally, X and Y are combined to form a 5-, 6-, 7- or 8-membered fused ring containing from 0 to 3 heteroatoms selected from the group consisting of N, O and S;

Z is selected from the group consisting of —CO$_2$R$^{12}$, —C(O)NR$^{12}$R$^{13}$ and heteroaryl;

L is a divalent linkage selected from the group consisting of a single bond, (C$_1$-C$_6$)alkylene and (C$_2$-C$_4$)heteroalkylene;

R$^2$ is selected from the group consisting of hydrogen, —OR', (C$_1$-C$_8$)alkyl, hetero(C$_2$-C$_8$)alkyl, aryl, heteroaryl and aryl(C$_1$-C$_4$)alkyl;

R$^3$, R$^4$, R$^5$ and R$^6$ are independently selected from the group consisting of hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R", —OR', —NO$_2$, —CN, —C(O)R', —CO$_2$R', —C(O)NR'R", (C$_1$-C$_4$)alkylene-C(O)NR'R", —S(O)$_m$R', —S(O)$_k$NR'R", —OC(O)OR', —OC(O)R', —OC(O)NR'R", —N(R''')C(O)NR'R", —N(R'')C(O)R' and —N(R'')C(O)OR';

R$^7$ is selected from the group consisting of hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R", —OR', —C(O)R', —CO$_2$R', —C(O)NR'R", —S(O)$_m$R' and —S(O)$_k$NR'R";

R$^a$ and R$^b$ are independently selected from the group consisting of hydrogen, (C$_1$-C$_6$)alkyl, hetero(C$_2$-C$_6$)alkyl, aryl(C$_1$-C$_4$)alkyl, —OR' and —NR'R";

optionally, R$^a$ and R$^b$ are combined to form a 5-, 6-, 7- or 8-membered spiro ring containing from 0 to 3 heteroatoms selected from the group consisting of N, O and S;

R$^8$, R$^{10}$ and R$^{11}$ are independently selected from the group consisting of hydrogen, (C$_1$-C$_8$)alkyl, fluoro(C$_1$-C$_4$)alkyl, hetero(C$_2$-C$_8$)alkyl, aryl, heteroaryl, -aryl(C$_1$-C$_4$)alkyl, —C(O)R', —CO$_2$R', —C(O)NR'R", —S(O)$_m$R' and —S(O)$_k$NR'R";

R$^9$ is selected from the group consisting of (C$_1$-C$_6$)alkyl, hetero(C$_2$-C$_6$)alkyl, aryl(C$_1$-C$_4$)alkyl, —OR' and —NR'R";

optionally, R$^8$ or R$^9$ is combined with W to form a 5-, 6-, 7- or 8-membered fused ring containing from 0 to 3 heteroatoms selected from the group consisting of N, O and S;

optionally, R$^a$, R$^b$, R$^8$ or R$^9$ is combined with Y to form a 5-, 6-, 7- or 8-membered fused ring containing from 0 to 3 heteroatoms selected from the group consisting of N, O and S;

R$^{12}$ and R$^{13}$ are independently selected from the group consisting of hydrogen, (C$_1$-C$_6$)alkyl, hetero(C$_2$-C$_6$)alkyl, aryl, aryl(C$_1$-C$_4$)alkyl and heteroaryl;

optionally, R$^{12}$ and R$^{13}$ are combined with the nitrogen atom to which they are attached to form a 5-, 6- or 7-membered ring containing from 0 to 2 additional heteroatoms selected from the group consisting of N, O and S;

each R', R" and R''' is independently selected from the group consisting of hydrogen, (C$_1$-C$_6$)alkyl, cyclo(C$_3$-C$_8$)alkyl, aryl and aryl(C$_1$-C$_4$)alkyl;

optionally, when R' and R" are attached to the same nitrogen atom, R' and R" may be combined to form a 5-, 6-, 7- or 8-membered ring containing from 1 to 3 heteroatoms selected from the group consisting of N, O and S;

each subscript k is 0, 1 or 2; and
the subscript m is 0, 1, 2 or 3;

with the proviso that when
$A^1$ is C(R$^3$), $D^1$ is C(R$^4$)=C(R$^5$);
W is a benzene ring,
X is —O— or —S—; and
—Y—R$^2$ is —NHSO$_2$-heterocyclo(C$_3$-C$_8$)alkyl, —NHSO$_2$-phenyl or —NHSO$_2$-heteroaryl;
$A^2$ is other than C(O— substituted (C$_2$-C$_4$)alkyl) or C(S-substituted (C$_2$-C$_4$)alkyl).

Unless otherwise indicated, the compounds provided in the above formula are meant to include pharmaceutically acceptable salts and prodrugs thereof.

The invention also provides pharmaceutical compositions comprising a compound of formula I and a pharmaceutically acceptable carrier, excipient or diluent.

The invention also provides methods for treating or preventing inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion and urticaria, comprising administering to a subject in need thereof a therapeutically effective amount of a compound of formula I.

The invention also provides methods for treating or preventing a condition or disorder mediated, regulated or influenced by Th2 cells, eosinophils, basophils, platelets, Langerhans cells, dendritic cells or mast cells, comprising administering to a subject in need thereof a therapeutically effective amount of a compound of formula I.

The invention also provides methods for treating or preventing a condition or disorder mediated, regulated or influenced by PGD$_2$ and metabolites thereof, such as 13,14-dihydro-15-keto-PGD$_2$ and 15-deoxy-$\Delta^{12,14}$-PGD$_2$, comprising administering to a subject in need thereof a therapeutically effective amount of a compound of formula I.

The invention further provides methods for treating or preventing a condition or disorder responsive to modulation of CRTH2 and/or one or more other PGD$_2$ receptors, e.g., DP, comprising administering to a subject in need thereof a therapeutically effective amount of a compound of formula I.

The invention also provides methods for treating or preventing a condition or disorder mediated by CRTH2 and/or one or more other PGD$_2$ receptors, e.g., DP, comprising administering to a subject in need thereof a therapeutically effective amount of a compound of formula I.

The invention also provides methods for modulating CRTH2 and/or one or more other PGD$_2$ receptors, e.g., DP, comprising contacting a cell with a compound of formula I.

Other objects, features and advantages of the invention will become apparent to those skilled in the art from the following description and claims.

DETAILED DESCRIPTION OF THE INVENTION

Abbreviations and Definitions

The abbreviations used herein are conventional, unless otherwise defined.

The terms "treat", "treating" and "treatment", as used herein, are meant to include alleviating or abrogating a disease and/or its attendant symptoms and alleviating or eradicating the cause of the disease itself.

The terms "prevent", "preventing" and "prevention", as used herein, refer to a method of delaying or precluding the onset of a disease and/or its attendant symptoms, barring a subject from acquiring a disease or reducing a subject's risk of acquiring a disease.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "CRTH2" refers to a CRTH2 protein (RefSeq Accession No. NP_007469) or variant thereof that is capable of mediating a cellular response to $PGD_2$ in vitro or in vivo. CRTH2 variants include proteins substantially homologous to native CRTH2, i.e., proteins having one or more naturally or non-naturally occurring amino acid deletions, insertions or substitutions (e.g., CRTH2 derivatives, homologs and fragments). The amino acid sequence of CRTH2 variant preferably is at least about 80% identical to a native CRTH2, more preferably at least about 90% identical, and most preferably at least about 95% identical.

As used herein, the terms "other $PGD_2$ receptor", "another $PGD_2$ receptor" and the like refer to a prostanoid receptor protein other than CRTH2, or variant thereof, that is capable of mediating a cellular response to $PGD_2$ in vitro or in vivo. Another $PGD_2$ receptor may be selective for $PGD_2$, e.g., DP (RefSeq Accession No. NP_000944), or other one or more other prostanoids (e.g., $EP_1$, $EP_2$, $EP_3$ and $EP_4$, FP, IP and TP). Other $PGD_2$ receptor variants include proteins substantially homologous to a corresponding native prostanoid receptor other than CRTH2, i.e., proteins having one or more naturally or non-naturally occurring amino acid deletions, insertions or substitutions (e.g., derivatives, homologs and fragments of another $PGD_2$ receptor). The amino acid sequence of other $PGD_2$ receptor variants preferably is at least about 80% identical to the corresponding native other $PGD_2$ receptors, more preferably at least about 90% identical, and most preferably at least about 95% identical. Preferably, another $PGD_2$ receptor is DP.

As used herein, the term "DP" refers to a DP protein (RefSeq Accession No. NP_000944) or variant thereof that is capable of mediating a cellular response to $PGD_2$ in vitro or in vivo. DP variants include proteins substantially homologous to native DP, i.e., proteins having one or more naturally or non-naturally occurring amino acid deletions, insertions or substitutions (e.g., DP derivatives, homologs and fragments). The amino acid sequence of DP variant preferably is at least about 80% identical to a native DP, more preferably at least about 90% identical, and most preferably at least about 95% identical.

The terms "modulate", "modulation" and the like refer to the ability of a compound to increase or decrease the function and/or expression of CRTH2 and/or one or more other $PGD_2$ receptors, e.g., DP, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with CRTH2 and/or one or more other $PGD_2$ receptors, either directly or indirectly, and/or the upregulation or downregulation of the expression of CRTH2 and/or one or more other $PGD_2$ receptors, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of CRTH2 and/or one or more other $PGD_2$ receptors can be demonstrated in a biochemical assay, e.g., binding assay, or a cell-based assay, e.g., a transient transfection assay.

The term "CRTH2-modulating amount" refers to that amount of a compound that is needed to produce a desired effect in any one of the cell-based assays, biochemical assays or animal models described herein or otherwise known to the skilled artisan. Typically, a CRTH2-modulating amount of a compound will be at least that amount which exhibits an $EC_{50}$ in a reporter-gene cell-based assay (relative to an untreated control).

As used herein, the terms "CRTH2-responsive condition or disorder," "condition or disorder responsive to CRTH2" and related terms and phrases refer to a condition or disorder associated with inappropriate, e.g., less than or greater than normal, CRTH2 activity and at least partially responsive to or affected by CRTH2 modulation (e.g., a CRTH2 antagonist or agonist results in some improvement in patient well-being in at least some patients). Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-associated condition or disorder may include a CRTH2-mediated condition or disorder.

As used herein, the phrases "CRTH2-mediated condition or disorder," "a condition or disorder mediated by CRTH2" and related phrases and terms refer to a condition or disorder characterized by inappropriate, e.g., less than or greater than normal, CRTH2 activity. Inappropriate CRTH2 functional activity might arise as the result of CRTH2 expression in cells which normally do not express CRTH2, increased CRTH2 expression or degree of intracellular activation (leading to, e.g., inflammatory and immune-related disorders and diseases) or decreased CRTH2 expression. A CRTH2-mediated condition or disorder may be completely or partially mediated by inappropriate CRTH2 functional activity. However, a CRTH2-mediated condition or disorder is one in which modulation of CRTH2 results in some effect on the underlying condition or disorder (e.g., an CRTH2 antagonist or agonist results in some improvement in patient well-being in at least some patients).

The term "$PGD_2$ receptor-modulating amount" and related terms and phrases refer to that amount of a compound that is needed to produce a desired effect in any one of the cell-based assays, biochemical assays or animal models described herein or otherwise known to the skilled artisan. Typically, a $PGD_2$ receptor-modulating amount of a compound will be at least that amount which exhibits an $EC_{50}$ in a reporter-gene cell-based assay (relative to an untreated control).

As used herein, the term "condition or disorder responsive to another $PGD_2$ receptor" and related terms and phrases refer to a condition or disorder associated with inappropriate, e.g., less than or greater than normal, activity of another $PGD_2$ receptor and at least partially responsive to or affected by modulation of another $PGD_2$ receptor (e.g., another $PGD_2$ receptor antagonist or agonist results in some improvement in patient well-being in at least some patients). Inappropriate functional activity of another $PGD_2$ receptor might arise as the result of expression of another $PGD_2$ receptor in cells which normally do not express the receptor, increased expression of another $PGD_2$ receptor or degree of intracellular activation (leading to, e.g., inflammatory and immune-related disorders and diseases) or decreased expression of another $PGD_2$ receptor. A condition or disorder associated with another $PGD_2$ receptor may include a condition or disorder mediated by another $PGD_2$ receptor.

As used herein, the phrase "condition or disorder mediated by another $PGD_2$ receptor" and related phrases and terms refer to a condition or disorder characterized by inappropriate, e.g., less than or greater than normal, activity of another $PGD_2$ receptor. Inappropriate functional activity of another $PGD_2$ receptor might arise as the result of expression of another $PGD_2$ receptor in cells which normally do not express the receptor, increased expression of another $PGD_2$ receptor or degree of intracellular activation (leading to, e.g., inflammatory and immune-related disorders and diseases) or decreased expression of another $PGD_2$ receptor. A condition or disorder mediated by another $PGD_2$ receptor may be completely or partially mediated by inappropriate functional activity of another $PGD_2$ receptor. However, a condition or disorder mediated by of another $PGD_2$ receptor is one in which modulation of another $PGD_2$ receptor results in some effect on the underlying condition or disorder (e.g., another $PGD_2$ receptor antagonist or agonist results in some improvement in patient well-being in at least some patients).

The term "DP-modulating amount" refers to that amount of a compound that is needed to produce a desired effect in any one of the cell-based assays, biochemical assays or animal models described herein or otherwise known to the skilled artisan. Typically, a DP-modulating amount of a compound will be at least that amount which exhibits an $EC_{50}$ in a reporter-gene cell-based assay (relative to an untreated control).

As used herein, the terms "DP-responsive condition or disorder," "condition or disorder responsive to DP" and related terms and phrases refer to a condition or disorder associated with inappropriate, e.g., less than or greater than normal, DP activity and at least partially responsive to or affected by DP modulation (e.g., a DP antagonist or agonist results in some improvement in patient well-being in at least some patients). Inappropriate DP functional activity might arise as the result of DP expression in cells which normally do not express DP, increased DP expression or degree of intracellular activation (leading to, e.g., inflammatory and immune-related disorders and diseases) or decreased DP expression. A DP-associated condition or disorder may include a DP-mediated condition or disorder.

As used herein, the phrases "DP-mediated condition or disorder," "a condition or disorder mediated by DP" and related phrases and terms refer to a condition or disorder characterized by inappropriate, e.g., less than or greater than normal, DP activity. Inappropriate DP functional activity might arise as the result of DP expression in cells which normally do not express DP, increased DP expression or degree of intracellular activation (leading to, e.g., inflammatory and immune-related disorders and diseases) or decreased DP expression. A DP-mediated condition or disorder may be completely or partially mediated by inappropriate DP functional activity. However, a DP-mediated condition or disorder is one in which modulation of DP results in some effect on the underlying condition or disorder (e.g., an DP antagonist or agonist results in some improvement in patient well-being in at least some patients).

The term "alkyl," by itself or as part of another substituent, means, unless otherwise stated, a straight or branched chain, or cyclic hydrocarbon radical, or combination thereof, which is fully saturated, having the number of carbon atoms designated (i.e., $C_1$-$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —CH$_2$—NH—OCH$_3$ and —CH$_2$—O—Si(CH$_3$)$_3$. When a prefix such as (C$_2$-C$_8$) is used to refer to a heteroalkyl group, the number of carbons (2-8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Thus, the terms "cycloalkyl" and "heterocycloalkyl" are meant to be included in the terms "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo (C$_1$-C$_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo(C$_1$-C$_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, α-carboline, β-carboline, γ-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl or quinolyl group which is unsubstituted or substituted.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C (NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R''', —OC(O)R', —C(O)R', —CO$_2$R', —CONR'R", —OC(O)NR'R", —NR"C(O)R', —NR"CO$_2$R', —NR'—SO$_2$NR"R''', —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen; —OC(O)R', —CO$_2$R', —CONR'R", —OC(O)NR'R", —NR"C(O)R', —NR"CO$_2$R', —NR'—SO$_2$NR"R''', —SO$_2$R', —SO$_2$NR'R", —NR"SO$_2$R, —CN and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Otherwise, R' is as defined above.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., CRTH2 assay reagents, and diagnostic agents, e.g., in vivo imaging agents. All isotopic variations of the compounds of the invention, whether radioactive or not, are intended to be encompassed within the scope of the invention.

EMBODIMENTS OF THE INVENTION

A class of compounds that modulate CRTH2 and/or DP and/or one or more other $PGD_2$ receptors has been discovered. Depending on the biological environment (e.g., cell type, pathological condition of the host, etc.), these compounds can activate or inhibit the actions of CRTH2 and/or one or more other $PGD_2$ receptors (e.g., ligand binding). By activating or inhibiting CRTH2 and/or one or more other $PGD_2$ receptors, the compounds will find use as therapeutic agents capable of modulating diseases and conditions responsive to modulation of CRTH2 and/or one or more other $PGD_2$ receptors and/or mediated by CRTH2 and/or one or more other PGD, receptors. As noted above, examples of such diseases and conditions include inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion and urticaria. Additionally, the compounds are useful for the treatment and/or prevention of complications of these diseases and disorders (e.g., cardiovascular disease).

While the compounds of the invention are believed to exert their effects by interacting with CRTH2, the mechanism of action by which the compounds act is not a limiting embodiment of the invention. For example, compounds of the invention may interact with $PGD_2$ receptor subtypes other than CRTH2, e.g., DP receptor, and/or other prostanoid receptors, e.g., thromboxane $A_2$ ($TXA_2$) receptor. Indeed, as alluded to above, the present invention specifically contemplates the use of the disclosed compounds to modulate one or more $PGD_2$ receptors other than CRTH2.

Compounds contemplated by the invention include, but are not limited to, the exemplary compounds provided herein.

Compounds

In one aspect, the invention provides compounds of formula (I):

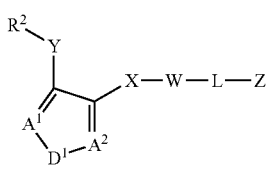

I or a pharmaceutically acceptable salt or prodrug thereof. In formula I, the symbol $A^1$ represents $C(R^3)$ or N and the symbol $A^2$ represents $C(R^6)$ or N. When $A^1$ is $C(R^3)$ and $A^2$ is $C(R^6)$, the symbol $D^1$ represents $C(R^4)=C(R^5)$, $C(R^4)=N$, $NR^7$, O or S. When $A^1$ or $A^2$ is N, the symbol $D^1$ represents $C(R^4)=C(R^5)$ or $C(R^4)=N$. Thus, A1, A2, the carbon atoms to which $A^1$ and $A^2$ are attached and $D^1$ combine to form a 5- or 6-membered ring, e.g.,

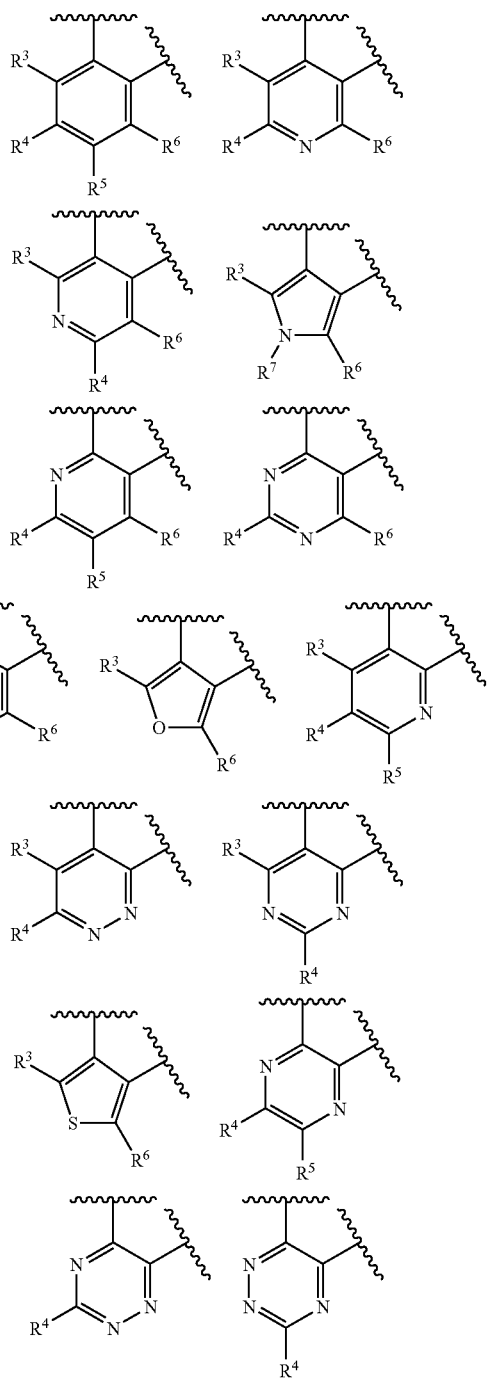

Exemplary combinations of $A^1$, $A^2$, the carbon atoms to which $A^1$ and $A^2$ are attached and $D^1$ are:

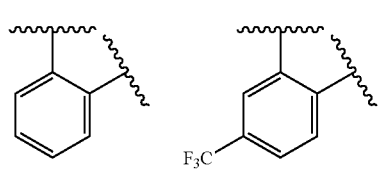

-continued
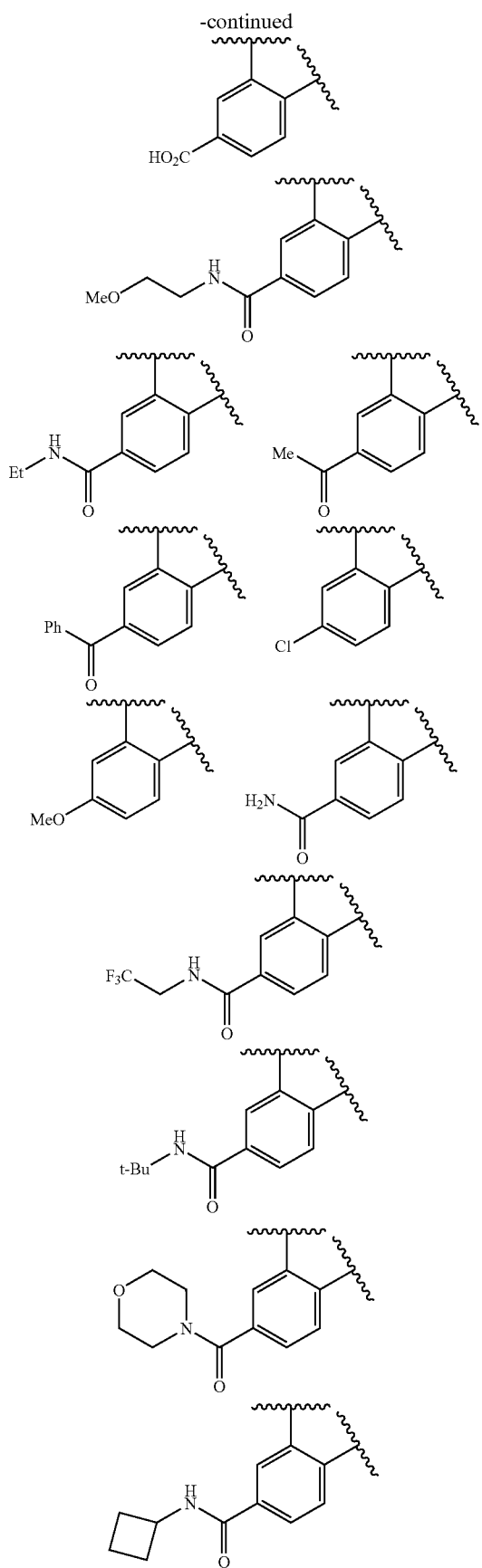
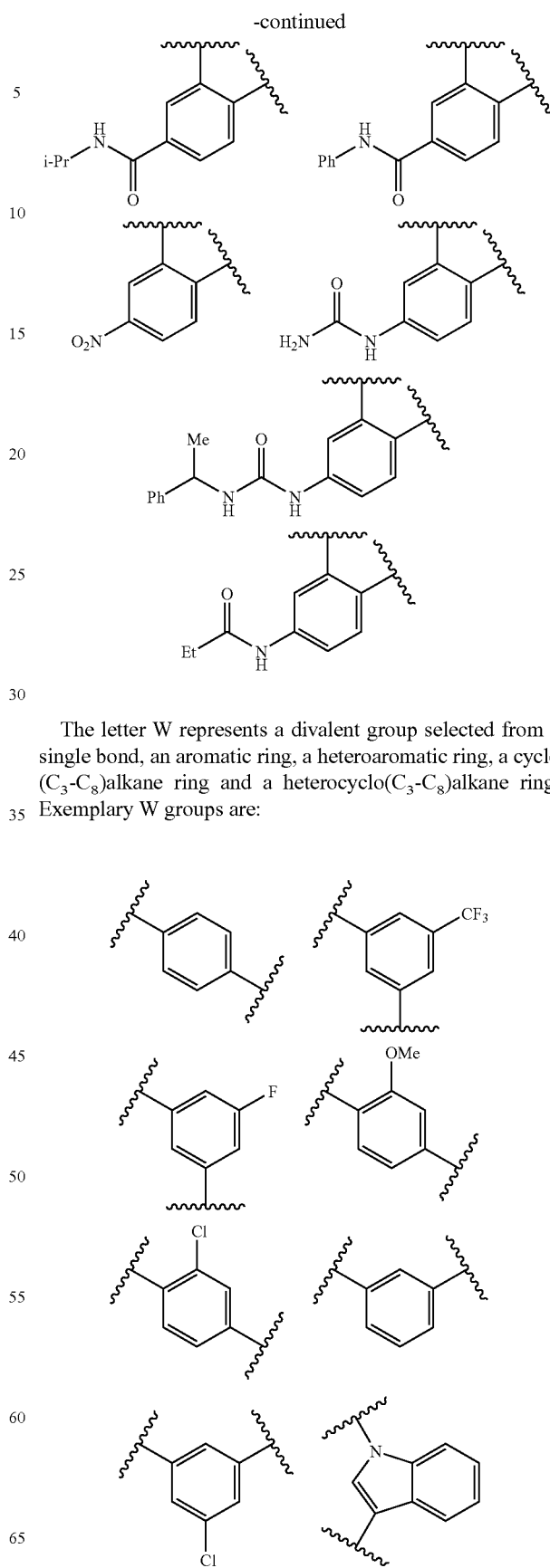
The letter W represents a divalent group selected from a single bond, an aromatic ring, a heteroaromatic ring, a cyclo ($C_3$-$C_8$)alkane ring and a heterocyclo($C_3$-$C_8$)alkane ring. Exemplary W groups are:

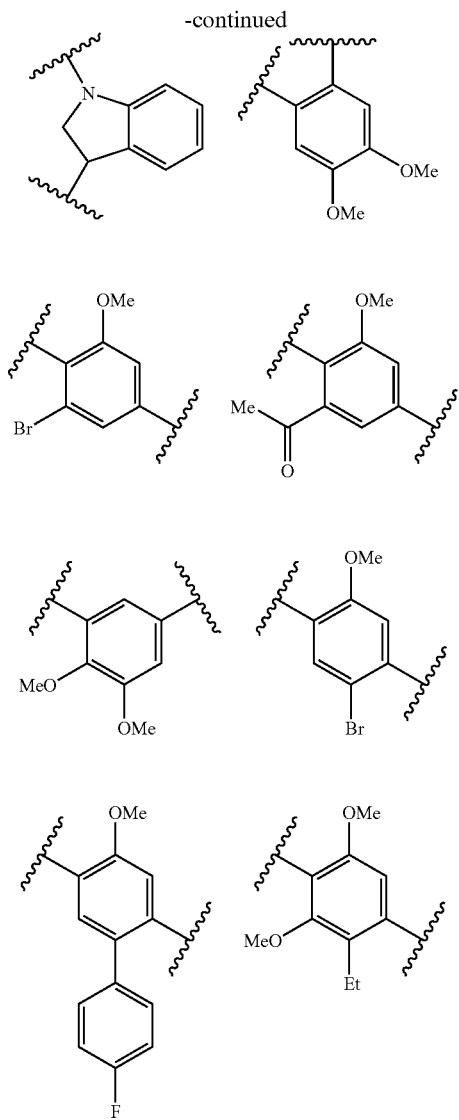

The letter X represents a divalent linkage selected from —O—, —S(O)$_k$—, —CR$^a$R$^b$—, —C(O)—, —NR$^8$— and —C(NR$^9$)—. Exemplary X groups are —O—, —SO$_2$—, —CH$_2$—, —C(O)—, —CH(OH)— and —NH—.

The letter Y represents a divalent linkage selected from a single bond, —S(O)$_k$NR$^{10}$—, —C(O)NR$^{10}$—, (C$_1$-C$_4$)alkylene, hetero(C$_2$-C$_4$)alkylene, —N(R$^{11}$)C(O)NR$^{10}$—, —N(R$^{11}$)S(O)$_k$NR$^{10}$—, —N(R$^{11}$)CO$_2$—, —NR$^{11}$—, —O— and —S(O)$_k$—. Exemplary Y groups are —SO$_2$NH—, —SO$_2$NMe-, —C(O)NH—, —NH—, —NHCO$_2$— and —NHC(O)NMe-.

The letter Z represents —CO$_2$R$^{12}$, —C(O)NR$^{12}$R$^{13}$ or heteroaryl. Exemplary Z groups are —CO$_2$H, —C(O)NHEt, —C(O)NH$_2$, —CO$_2$Et, —CO$_2$Me, —CO$_2$CH$_2$S(O)Me, 5-tetrazolyl and —C(O)NHOH.

The letter L represents a divalent linkage selected from a single bond, (C$_1$-C$_6$)alkylene and (C$_2$-C$_4$)heteroalkylene. Exemplary L groups are methylene, ethylene, chloromethylene, hydroxymethylene and methylmethylene.

The substituent R$^2$ is hydrogen, —OR', (C$_1$-C$_8$)alkyl, hetero(C$_2$-C$_8$)alkyl, aryl, heteroaryl or aryl(C$_1$-C$_4$)alkyl. Exemplary R$^2$ groups are 4-tolyl, 2-naphthyl, methyl, phenyl, 2,4-dichlorophenyl, 4-methoxyphenyl, 4-trifluoromethoxyphenyl, 2-chlorophenyl, 4-chlorophenyl, 3-chlorophenyl, 2,4-dichloro-5-methylphenyl, 4-n-pentylphenyl, 4-cyanophenyl, 4-n-butoxyphenyl, 2-cyano-3-chlorophenyl, 3-chloro-4-methylphenyl, 2-methoxy-5-bromophenyl, 5-trifluoromethoxy-2-pyridyl, 8-quinolyl, 2-thieneyl, 3-methyl-7-chlorobenzothienyl, 1-methyl-4-imidazolyl, benzyl and 2,4-difluorophenyl.

R$^3$, R$^4$, R$^5$ and R$^6$ are independently hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R", —OR', —NO$_2$, —CN, —C(O)R', —CO$_2$R', —C(O)NR'R", (C$_1$-C$_4$)alkylene-C(O)NR'R", —S(O)$_m$R', —S(O)$_k$NR'R", —OC(O)OR', —OC(O)R', —OC(O)NR'R", —N(R''')C(O)NR'R", —N(R")C(O)R' or —N(R")C(O)OR'.

R$^7$ is hydrogen, halogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —NR'R", —OR', —C(O)R', —CO$_2$R', —C(O)NR'R", —S(O)$_m$R' or —S(O)$_k$NR'R".

R$^a$ and R$^b$ are independently hydrogen, (C$_1$-C$_6$)alkyl, hetero(C$_2$-C$_6$)alkyl, aryl(C$_1$-C$_4$)alkyl, —OR' or —NR'R".

R$^8$, R$^{10}$ and R$^{11}$ are independently hydrogen, (C$_1$-C$_8$)alkyl, fluoro(C$_1$-C$_4$)alkyl, hetero(C$_2$-C$_8$)alkyl, aryl, heteroaryl, aryl(C$_1$-C$_4$)alkyl, —C(O)R', —CO$_2$R', —C(O)NR'R", —S(O)$_m$R' or —S(O)$_k$NR'R".

R$^9$ is (C$_1$-C$_6$)alkyl, hetero(C$_2$-C$_6$)alkyl, aryl(C$_1$-C$_4$)alkyl, —OR' or —NR'R".

R$^{12}$ and R$^{13}$ are independently hydrogen, (C$_1$-C$_6$)alkyl, hetero(C$_2$-C$_6$)alkyl, aryl, aryl(C$_1$-C$_4$)alkyl or heteroaryl.

Each R', R" and R''' is independently hydrogen, (C$_1$-C$_6$) alkyl, cyclo(C$_3$-C$_8$)alkyl, aryl or aryl(C$_1$-C$_4$)alkyl.

Each subscript k is 0, 1 or 2.

The subscript m is 0, 1, 2 or 3.

In optional embodiments, A$^2$ and W are combined to form a 5-, 6-, 7- or 8-membered fused ring containing from 0 to 3 heteroatoms selected from N, O and S; X and Y are combined to form a 5-, 6-, 7- or 8-membered fused ring containing from 0 to 3 heteroatoms selected from N, O and S; R$^a$ and R$^b$ are combined to form a 5-, 6-, 7- or 8-membered spiro ring containing from 0 to 3 heteroatoms selected from N, O and S; R$^8$ or R$^9$ is combined with W to form a 5-, 6-, 7- or 8-membered fused ring containing from 0 to 3 heteroatoms selected from N, O and S; R$^a$, R$^b$, R$^8$ or R$^9$ is combined with Y to form a 5-, 6-, 7- or 8-membered fused ring containing from 0 to 3 heteroatoms selected from N, O and S; R$^{12}$ and R$^{13}$ are combined with the nitrogen atom to which they are attached to form a 5-, 6- or 7-membered ring containing from 0 to 2 additional heteroatoms selected from N, O and S; and when R' and R" are attached to the same nitrogen atom, R' and R" are combined to form a 5-, 6-, 7- or 8-membered ring containing from 1 to 3 heteroatoms selected from N, O and S.

Within the above compounds of formula I, compounds wherein A$^2$ is C(O-substituted (C$_2$-C$_4$)alkyl) or C(S-substituted (C$_2$-C$_4$)alkyl); A$^1$ is C(R$^3$), D$^1$ is C(R$^4$)═C(R$^5$); W is a benzene ring; X is —O— or —S—; and —Y—R$^2$ is —NHSO$_2$-heterocyclo(C$_3$-C$_8$)alkyl, —NHSO$_2$-phenyl or —NHSO$_2$-heteroaryl are excluded.

In one group of embodiments, A$^1$ is C(R$^3$), A$^2$ is C(R$^6$) and D$^1$ is C(R$^4$)═C(R$^5$).

One group of embodiments is represented by the formula (II):

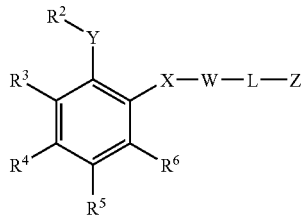

II wherein $R^3$, $R^4$, $R^5$ and $R^6$ are independently hydrogen, halogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —NR'R", —OR', —NO$_2$, —CN, —C(O)R', —CO$_2$R', —C(O)NR'R", ($C_1$-$C_4$)alkylene-C(O)NR'R", —S(O)$_m$R', —S(O)$_k$NR'R", —OC(O)R', —OC(O)R', —OC(O)NR'R", —N(R''')C(O)NR'R", —N(R")C(O)R' or —N(R")C(O)OR'. The other variables, (e.g., W, X, Y, Z, L, $R^2$, R' and R"), have the meanings provided above. Optionally, $R^6$ may be combined with W to form a 5-, 6-, 7- or 8-membered fused ring containing from 0 to 3 heteroatoms selected from N, O and S.

Within the above compounds of formula II, compounds wherein $R^6$ is —O-substituted ($C_2$-$C_4$)alkyl or —S-substituted ($C_2$-$C_4$)alkyl; W is a benzene ring; X is —O— or —S—; and —Y—$R^2$ is —NHSO$_2$-heterocyclo($C_3$-$C_8$)alkyl, —NHSO$_2$-phenyl or —NHSO$_2$-heteroaryl are excluded.

Within formula II are provided several groups of embodiments.

(1) In one group of embodiments, $R^6$ is hydrogen, halogen, ($C_1$-$C_8$)alkyl, fluoro($C_1$-$C_4$)alkyl, aryl, heteroaryl, aryl ($C_1$-$C_4$)alkyl, —NR'R", —NO$_2$, —CN, —C(O)R', —CO$_2$R', —C(O)NR'R", —S(O)$_m$R', —S(O)$_k$NR'R", —OC(O)OR', —OC(O)R', —OC(O)NR'R", —N(R''')C (O)NR'R", —N(R")C(O)R' or —N(R")C(O)OR'.

(2) In another group of embodiments, $R^3$, $R^4$ and $R^5$ are independently hydrogen, halogen, ($C_1$-$C_8$)alkyl, fluoro ($C_1$-$C_4$)alkyl, —OR', —NR'R", —NO$_2$, —CN, —C(O)R', —CO$_2$R', —C(O)NR'R", ($C_1$-$C_4$)alkylene-C(O)NR'R", —N(R")C(O)R', —N(R''')C(O)NR'R" or heteroaryl.

(3) In another group of embodiments, $R^6$ is hydrogen, halogen, ($C_1$-$C_8$)alkyl, fluoro($C_1$-$C_4$)alkyl, —NR'R", —NO$_2$, —CN, —C(O)R', —CO$_2$R', —C(O)NR'R", ($C_1$-$C_4$)alkylene-C(O)NR'R", —N(R")C(O)R', —N(R''')C(O)NR'R" or heteroaryl.

(4) In another group of embodiments, $R^6$ is hydrogen.

(5) In another group of embodiments, $R^3$, $R^5$ and $R^6$ are hydrogen.

(6) In another group of embodiments, $R^4$ is halogen, ($C_1$-$C_8$) alkyl, fluoro($C_1$-$C_4$)alkyl, —OR', —NO$_2$, —C(O)R', —CO$_2$R', C(O)NR'R", ($C_1$-$C_4$)alkylene-C(O)NR'R", —N(R")C(O)R', —N(R''')C(O)NR'R" or heteroaryl.

(7) In another group of embodiments, $R^3$, $R^5$ and $R^6$ are hydrogen and $R^4$ is halogen, ($C_1$-$C_8$)alkyl, fluoro($C_1$-$C_4$) alkyl, —OR', —NO$_2$, —C(O)R', —CO$_2$R', —C(O)NR'R", ($C_1$-$C_4$)alkylene-C(O)NR'R", —N(R")C(O)R', —N(R''')C (O)NR'R" or heteroaryl.

(8) In another group of embodiments, $R^6$ may be combined with W to form a 5-, 6-, 7- or 8-membered fused ring containing from 0 to 3 heteroatoms selected from N, O and S.

(9) In another group of embodiments, W is an aromatic ring, a heteroaromatic ring or a cyclo($C_3$-$C_8$)alkane ring.

(10) In another group of embodiments, W is benzene, indole, benzofuran, benzothiazole, indoline, dihydrobenzofuran, dihydrobenzothiazole, benzimidazole, benzoxazole, benzthiazole or cyclohexane.

(11) In another group of embodiments, W is benzene.

(12) One group of embodiments is represented by formula (III):

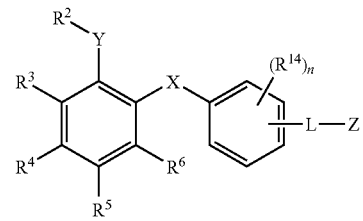

III wherein each $R^{14}$ is independently halogen, ($C_1$-$C_8$)alkyl, fluoro($C_1$-$C_4$)alkyl, —OR', —NR'R", —NO$_2$, —CN, C(O)R' or aryl and the subscript n is 0, 1, 2, 3 or 4. Optionally, any two adjacent $R^{14}$ groups may be combined to form a 5-, 6-, 7- or 8-membered fused ring containing from 0 to 3 heteroatoms selected from N, O and S. The variables X, Y, Z, L, $R^2$, $R^3$, $R^4$, $R^5$, $R^6$, R' and R" have the meanings and groupings provided above. Optionally, when an $R^{14}$ group is adjacent to X, the $R^{14}$ group may be combined with $R^6$ to form a 5-, 6-, 7- or 8-membered fused ring containing from 0 to 3 heteroatoms selected from N, O and S.

One of skill in the art will understand that a number of structural isomers are represented by formula III, for example:

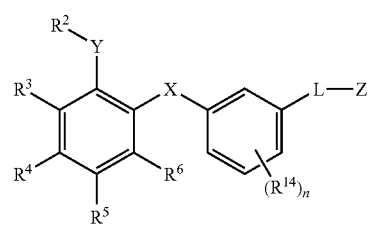

IIIa

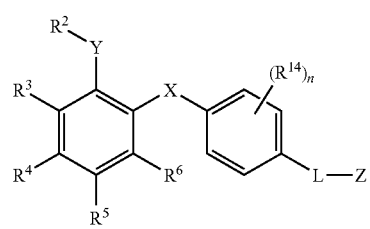

IIIb

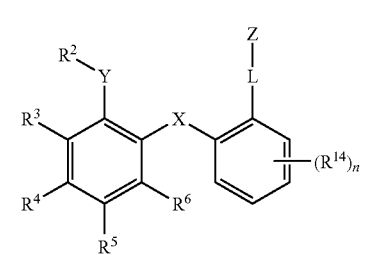

IIIc

Within formula III are provided several groups of embodiments.

(a) In one group of embodiments, n is 0.

(b) In another group of embodiments, n is 1, 2 or 3.

(c) In another group of embodiments, n is 1.

(d) In another group of embodiments, each $R^{14}$ is independently halogen, $(C_1\text{-}C_8)$alkyl, fluoro$(C_1\text{-}C_4)$alkyl, —OR', —C(O)R' or aryl.

(e) In another group of embodiments, $R^{14}$ is halogen, fluoro$(C_1\text{-}C_4)$alkyl or —OR' and n is 1.

(f) In another group of embodiments, each $R^{14}$ is independently $(C_1\text{-}C_6)$alkyl, halogen, fluoro$(C_1\text{-}C_4)$alkyl, —C(O)R', aryl or —OR' and n is 2 or 3.

(g) In another group of embodiments, an $R^{14}$ group adjacent to X is combined with $R^6$ to form a 5-, 6-, 7- or 8-membered fused ring containing from 0 to 3 heteroatoms selected from the group consisting of N, O and S.

(h) One group of embodiments is represented by formula (IV):

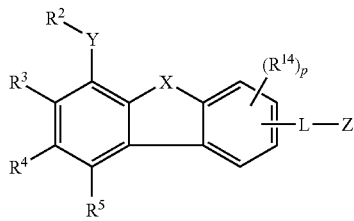

IV wherein the subscript p is 0, 1, 2 or 3. The variables X, Y, Z, L, $R^2$, $R^3$, $R^4$, $R^5$, $R^{14}$, R' and R" have the meanings provided above. In one embodiment, p is 0. In another embodiment, p is 1.

(i) Another group of embodiments is represented by formula (V):

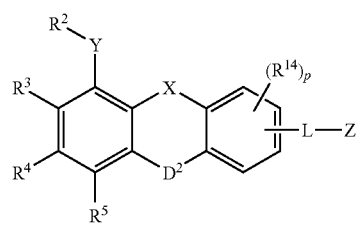

V wherein $D^2$ is O, $S(O)_k$, $CR^aR^b$, C(O) or $NR^8$ and the subscript p is 0, 1, 2 or 3. The variables X, Y, Z, L, $R^2$, $R^3$, $R^4$, $R^5$, $R^6$, $R^a$, $R^b$, $R^8$ and $R^{14}$ and the subscript k have the meanings and groupings provided above.

(i) Another group of embodiments is represented by formula (VI):

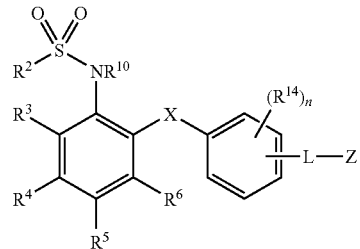

VI wherein the variables X, Z, L, $R^2$, $R^3$, $R^4$, $R^5$, $R^6$, $R^{10}$ and $R^{14}$ and the subscript n have the meanings and groupings provided above.

(j) Another embodiment is represented by formula (VII):

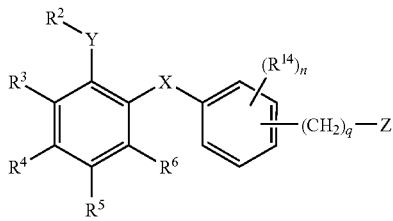

VII wherein the subscript q is 0, 1, 2, 3, 4, 5 or 6. The variables X, Y, Z, $R^2$, $R^3$, $R^4$, $R^5$, $R^6$, $R^{14}$, R' and R" and the subscript n have the meanings and groupings provided above. In one embodiment, q is 0, 1, 2 or 3. In another embodiment, q is 1 or 2. In another embodiment, q is 1.

(k) Another embodiment is represented by formula (VIII):

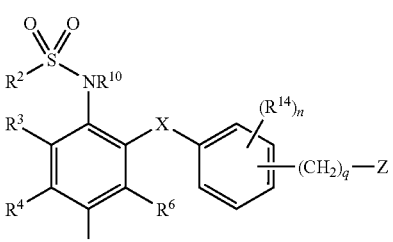

VIII wherein the variables X, Z, $R^2$, $R^3$, $R^4$, $R^5$, $R^6$, $R^{10}$ and $R^{14}$ and the subscripts n and q have the meanings and groupings provided above.

(l) In another group of embodiments, X is —O—, —$CR^aR^b$—, —C(O)— or —$NR^8$—. In one embodiment, X is —O—. In another embodiment, X is —$CR^aR^b$—. In another embodiment, X is —$NR^8$—.

(m) In another group of embodiments, Y is —$S(O)_k$$NR^{10}$—, —C(O)$NR^{10}$—, —$N(R^{11})$C(O)$NR^{10}$—, —$N(R^{11})$$S(O)_k$$NR^{10}$— or —$N(R^{11})$$CO_2$—. In one embodiment, Y is —$S(O)_k$$NR^{10}$—.

(n) In another group of embodiments, X and Y are combined to form a 5-, 6-, 7- or 8-membered fused ring containing from 0 to 3 heteroatoms selected from N, O and S.

(o) One group of embodiments is represented by the formula (IX):

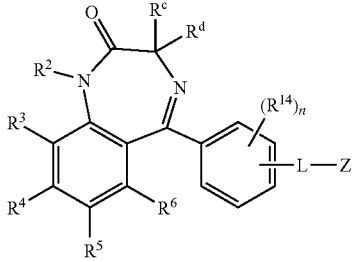

wherein $R^c$ and $R^d$ are independently hydrogen, $(C_1-C_6)$alkyl or =O. The variables Z, L, $R^2$, $R^3$, $R^4$, $R^5$, $R^6$, $R^{14}$, R' and R" and the subscript n have the meanings and groupings provided above.

(p) Another group of embodiments is represented by the formula (X):

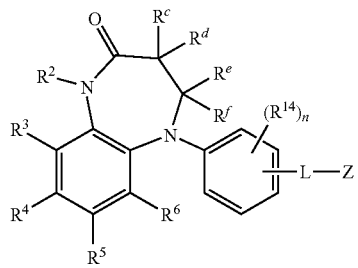

wherein $R^e$ and $R^f$ are independently hydrogen, $(C_1-C_6)$alkyl or =O. The variables Z, L, $R^2$, $R^3$, $R^4$, $R^5$, $R^6$, $R^{14}$, R', R", $R^c$ and $R^d$ and the subscript n have the meanings and groupings provided above.

(q) Another group of embodiments is represented by the formula (XI):

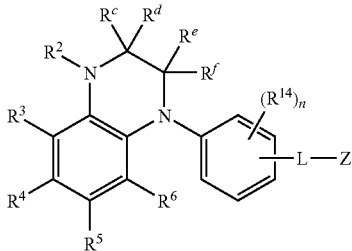

wherein the variables Z, L, $R^2$, $R^3$, $R^4$, $R^5$, $R^6$, $R^{14}$, R', R", $R^c$, $R^d$, $R^e$ and $R^f$ and the subscript n have the meanings and groupings provided above.

(r) In another group of embodiments Z is $CO_2R^{12}$, —C(O)$NR^{12}R^{13}$, imidazolyl or tetrazolyl, wherein $R^{12}$ and $R^{13}$ are as defined above. In one embodiment, Z is $CO_2R^{12}$, or —C(O)$NR^{12}R^{13}$. In another embodiment, Z is $CO_2H$.

It is to be understood that the group —$CO_2H$, as used herein, includes bioisosteric replacements therefor, such as:

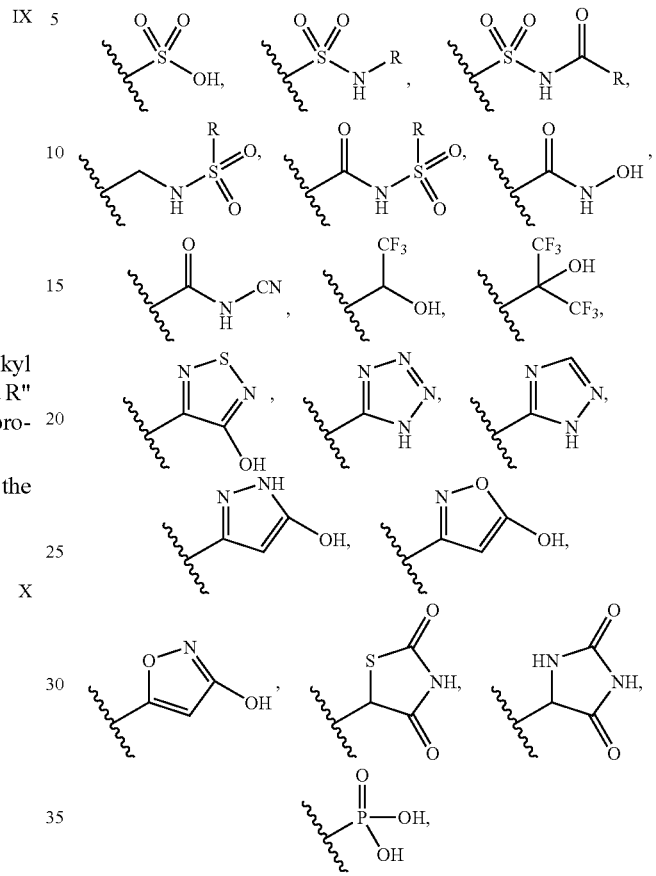

and the like. See, e.g., *The Practice of Medicinal Chemistry*; Wermuth, C. G., Ed.: Academic Press: New York, 1996; p. 203.

(s) In another group of embodiments, L a single bond or $(C_1-C_6)$alkylene. In one embodiment, L is $(C_1-C_6)$alkylene.

(t) In another group of embodiments, $R^2$ is phenyl or naphthyl.

(13) In another group of embodiments, W is benzofuran, benzothiazole, indoline, dihydrobenzofuran, dihydrobenzothiazole, benzimidazole, benzoxazole or benzthiazole.

(14) One group of embodiments is represented by formula (XII):

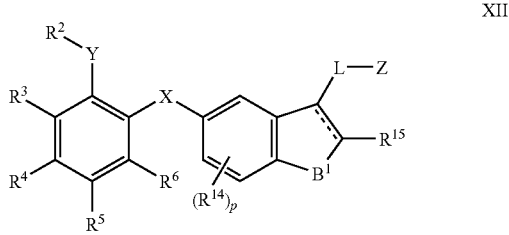

wherein $B^1$ is $N(R^{16})$, N, O or S, wherein $R^{16}$ is hydrogen, halogen, $(C_1-C_8)$alkyl, fluoro$(C_1-C_4)$alkyl, hetero$(C_2-C_8)$alkyl, aryl, heteroaryl, aryl$(C_1-C_4)$alkyl, —NR'R", —OR', —C(O)R', —CO₂R', —C(O)NR'R", —S(O)ₘR' or —S(O)ₖNR'R", R⁵ is hydrogen or (C₁-C₈)alkyl and the dotted line indicates an optional bond. The variables X, Y, Z, L, R², R³, R⁴, R⁵, R⁶, R¹⁴, R' and R" and the subscripts m and p have the meanings and groupings provided above.

(15) Another group of embodiments is represented by formula (XIII):

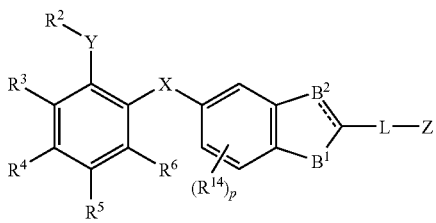

XIII wherein B² is C(R¹⁷) or N and R¹⁷ is hydrogen, halogen, (C₁-C₈)alkyl, fluoro(C₁-C₄)alkyl, hetero(C₂-C₈)alkyl, aryl, heteroaryl, aryl(C₁-C₄)alkyl, —NR'R", —OR', —C(O)R', —CO₂R', —C(O)NR'R", —S(O)ₘR' or —S(O)ₖNR'R". The variables X, Y, Z, L, B¹, R³, R⁴, R⁵, R⁶, R¹⁴, R' and R" and the subscripts m and p have the meanings and groupings provided above.

(16) Another group of embodiments is represented by formula (XIV):

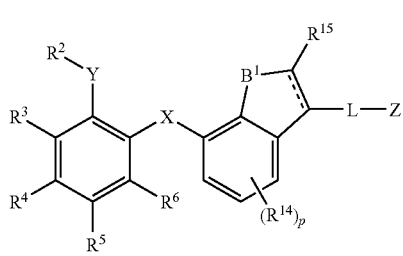

XIV wherein the variables X, Y, Z, L, B¹, R², R³, R⁴, R⁵, R⁶, R¹⁴ and R¹⁵ and the subscript p have the meanings and groupings provided above.

(17) Another group of embodiments is represented by formula (XV):

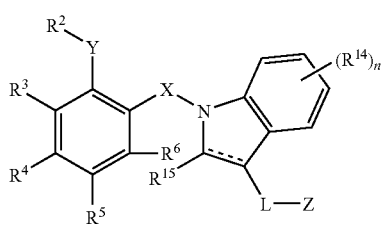

XV wherein the variables X, Y, Z, L, R², R³, R⁴, R⁵, R⁶, R¹⁴ and R¹⁵ and the subscript n have the meanings and groupings provided above.

One group of embodiments is represented by formula (XVI):

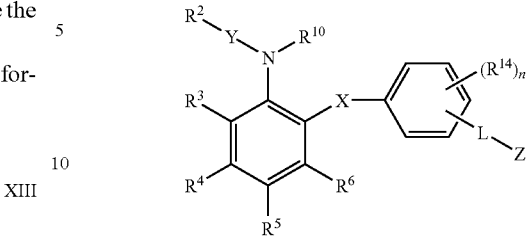

XVI or a pharmaceutically acceptable salt or prodrug thereof. In formula (XVI), the letter X represents a divalent linkage selected from —O— and —S(O)ₖ—. Exemplary X groups are —O—, —S—, and —SO₂—.

The letter Y represents a divalent linkage selected from a single bond, —S(O)ₖ—, —C(O)—, (C₂-C₄)alkylene, hetero(C₂-C₄)alkylene, and —O—. Exemplary Y groups are —SO₂—, —S—, and —C(O)—.

R² is a substituted or unsubstituted benzene ring. A substituted benzene ring will have from one to five substituents. Typically, a substituted benzene ring will have from one to three substituents. Substituents for the benzene ring are varied will include the preferred substituents for the aryl and heteroaryl groups as provided above.

In certain embodiments, R² is an unsubstituted benzene ring.

In other embodiments, R² is a substituted benzene ring and at least one substituent on the benzene ring is selected from the group consisting of halogen, —OCF₃, —OCH₃, —(C₁-C₅)alkyl, —CN, and —NO₂.

In other embodiments, R² is a benzene ring substituted with at least one halogen.

In yet other embodiments, R² is a benzene ring substituted with at least one chlorine.

R³ and R⁵ are independently selected from the group consisting of hydrogen, halogen, (C₁-C₈)alkyl, fluoro(C₁-C₄)alkyl, hetero(C₂-C₈)alkyl, aryl, heteroaryl, aryl(C₁-C₄)alkyl, —NR'R", —OR', —NO₂, —CN, —C(O)R', —CO₂R', —C(O)NR'R", —(C₁-C₄)alkylene-C(O)NR'R", —S(O)ₘR', —S(O)ₖNR'R", —OC(O)OR', —OC(O)R', —OC(O)NR'R", —N(R''')C(O)NR'R", —N(R")C(O)R' and —N(R")C(O)OR', where variables R', R", and R''' have the meanings provided below.

R⁴ is selected from the group consisting of hydrogen, —C(O)NR¹²R¹³ and —NC(O)-alkyl, where R¹² and R¹³ have the meanings provided below.

In certain embodiments, R⁴ is —NC(O)-cyclo(C₅-C₇)alkyl.

In other embodiments, R⁴ is —C(O)NH—(C₁-C₄)alkyl.

R⁶ is selected from the group consisting of hydrogen, halogen, (C₁-C₈)alkyl, fluoro(C₁-C₄)alkyl, hetero(C₂-C₈)alkyl, aryl, heteroaryl, aryl(C₁-C₄)alkyl, —NR'R", —NO₂, —CN, —C(O)R', —CO₂R', —C(O)NR'R", —(C₁-C₄)alkylene-C(O)NR'R", —S(O)ₘR', —S(O)ₖNR'R", —OC(O)OR', —OC(O)R', —OC(O)NR'R", —N(R''')C(O)NR'R", —N(R")C(O)R' and —N(R")C(O)OR'.

In certain embodiments, R⁶ is selected from the group consisting of hydrogen, halogen, (C₁-C₈)alkyl, fluoro(C₁-C₄)alkyl, aryl, heteroaryl, aryl(C₁-C₄)alkyl, —NR'R", —NO₂, —CN, —C(O)R', —CO₂R', —C(O)NR'R", —(C₁-C₄)alkylene-C(O)NR'R", —OC(O)OR', —OC(O)R', —OC(O)NR'R", —N(R''')C(O)NR'R", —N(R")C(O)R' and —N(R")C(O)OR'.

$R^{10}$ is selected from the group consisting of hydrogen, $(C_1\text{-}C_8)$alkyl, fluoro$(C_1\text{-}C_4)$alkyl, hetero$(C_2\text{-}C_8)$alkyl, aryl, heteroaryl, aryl$(C_1\text{-}C_4)$alkyl, —C(O)R', —CO$_2$R', —C(O)NR'R", —S(O)$_m$R' and —S(O)$_k$NR'R".

L is a divalent linkage selected from the group consisting of a single bond, $(C_1\text{-}C_6)$alkylene and $(C_2\text{-}C_4)$heteroalkylene.

Z is selected from the group consisting of —CO$_2$R$^{12}$, —C(O)NR$^{12}$R$^{13}$ and heteroaryl.

$R^{12}$ and $R^{13}$ are independently selected from the group consisting of hydrogen, $(C_1\text{-}C_8)$alkyl, hetero$(C_2\text{-}C_8)$alkyl, aryl, aryl$(C_1\text{-}C_4)$alkyl and heteroaryl.

Each $R^{14}$ is independently selected from the group consisting of halogen, $(C_1\text{-}C_8)$alkyl, fluoro$(C_1\text{-}C_4)$alkyl, —OR', —NR'R", —NO$_2$, —CN, —C(O)R' and aryl.

Each R', R" and R'" is independently selected from the group consisting of hydrogen, $(C_1\text{-}C_6)$alkyl, cyclo$(C_3\text{-}C_8)$alkyl, aryl and aryl$(C_1\text{-}C_4)$alkyl.

Each subscript k is independently 0, 1 or 2.

The subscript m is independently 0, 1, 2 or 3.

The subscript n is 0, 1, 2, 3 or 4.

Within formula (XVI), one group of embodiments is represented by formula (XVII):

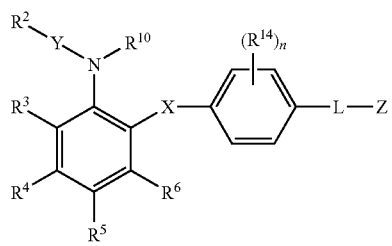

XVII wherein each variable, for example, X, Y, $R^2$, $R^3$, $R^4$, $R^5$, $R^6$, $R^{10}$, L, Z, $R^{12}$, $R^{13}$, $R^{14}$, R', R", and R'", have the meanings and groups as provided for formula (XVI).

Within formula (XVII), several groups of embodiments are provided.

In one group of embodiments, Y is —SO$_2$—, X is —O—, and $R^{10}$ is hydrogen.

In another group of embodiments, $R^4$ is —C(O)NH—$(C_1\text{-}C_4)$alkyl, and $R^6$ is hydrogen.

In another group of embodiments, $R^2$ is a benzene ring substituted with 1, 2, or 3 chlorine atoms.

In another group of embodiments, -L-Z taken together are —CH$_2$COOH.

In another group of embodiments, the subscript n is 1 or 2.

In another group of embodiments, $R^{14}$ is —OCH$_2$CH$_3$ or —OCH$_3$.

In another group of embodiments, $R^3$, $R^5$ and $R^6$ are each hydrogen.

Another group of embodiments within formula (XVII) is represented by formula (XVIII):

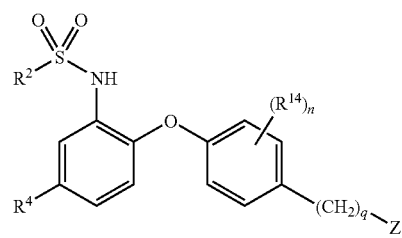

XVIII wherein $R^4$ is —C(O)NH—$(C_1\text{-}C_4)$alkyl, and the subscript q is 0, 1, 2, 3, 4, 5 or 6. Other variables, for example, $R^{14}$ and Z, have the meanings as provided for formula (XVII).

In certain embodiments within formula (XVIII), each $R^{14}$ is independently selected from the group consisting of $(C_1\text{-}C_6)$alkyl, halogen, fluoro$(C_1\text{-}C_4)$alkyl, —C(O)R', aryl and —OR' and subscript n is 2 or 3.

Within formula (XVI), one preferred group of embodiments are

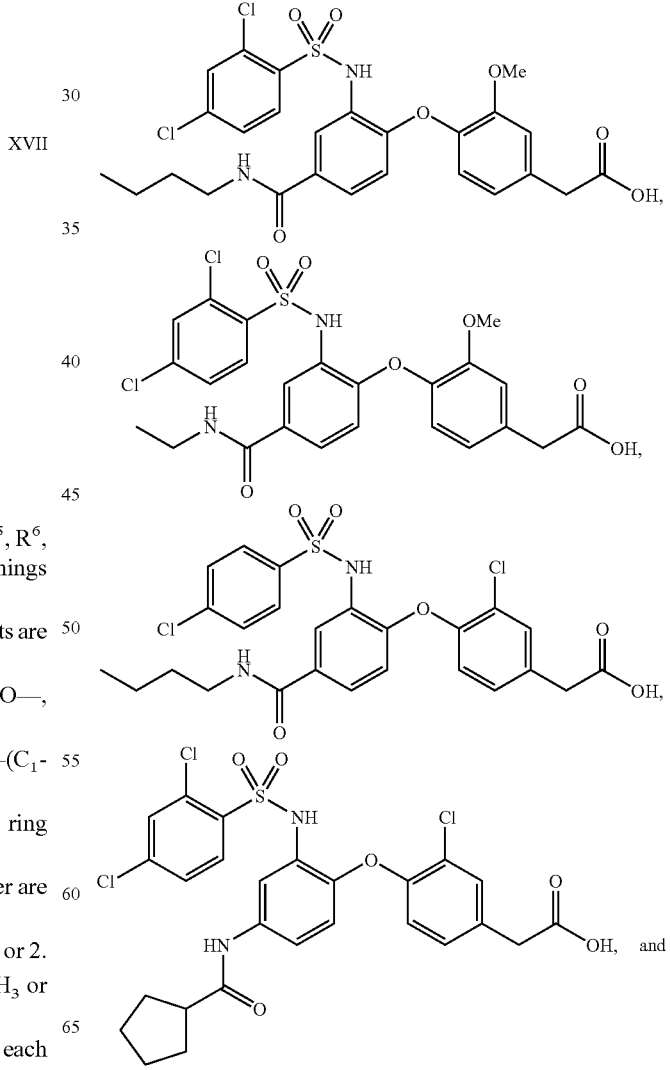

and

-continued

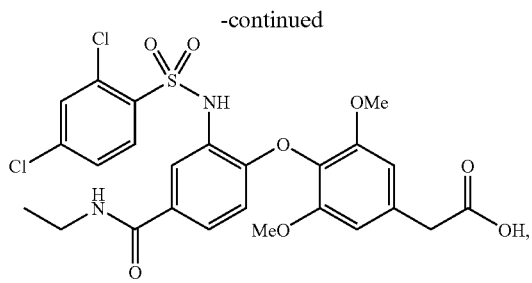

or pharmaceutically acceptable salt or prodrug thereof.

The invention encompasses novel compounds, novel pharmaceutical compositions and/or novel methods of use. While some compounds disclosed herein are available from commercial sources, the pharmaceutical compositions or methods of using these compounds are novel. Unless otherwise indicated, it is to be understood that the invention includes those compounds that are novel, as well as pharmaceutical compositions, various methods (e.g., methods of treating or preventing certain conditions and diseases mediated by CRTH2 and/or one or more other $PGD_2$ receptors), and the like which include both the novel compounds of the invention and compounds that are commercially available.

Preparation of the Compounds

Synthesis routes to the compounds provided herein are described in the Examples. One of skill in the art will understand that the synthetic routes can be modified to use different starting materials and/or alternate reagents to accomplish the desired transformations. Additionally, one of skill in the art will recognize that protecting groups may be necessary for the preparation of certain compounds and will be aware of those conditions compatible with a selected protecting group. Accordingly, the methods and reagents described herein are all expressed as non-limiting embodiments.

Compositions

In another aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

Formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of asthma, allergic diseases, inflammatory conditions and cancer and pathologies associated therewith (e.g., cardiovascular disease) or other adjuvant. In many instances, compositions which include a compounds of the invention and an alternative agent have additive or synergistic effects when administered.

Methods of Use

In yet another aspect, the invention provides methods of treating or preventing a disease or condition associated with CRTH2 and/or one or more other $PGD_2$ receptors by administering to a subject having such a condition or disease, a therapeutically effective amount of a compound or composition of the invention. In one group of embodiments, diseases and conditions, including chronic diseases of humans or other species, can be treated with modulators, or antagonists, of CRTH2 and/or one or more other $PGD_2$ receptors. These diseases and conditions include (1) inflammatory or allergic diseases such as systemic anaphylaxis and hypersensitivity disorders, atopic dermatitis, urticaria, drug allergies, insect sting allergies, food allergies (including celiac disease and the like) and mastocytosis, (2) inflammatory bowel diseases such as Crohn's disease, ulcerative colitis, ileitis and enteritis, (3) vasculitis, Behcet's syndrome, (4) psoriasis and inflammatory dermatoses such as dermatitis, eczema, atopic dermatitis, allergic contact dermatitis, urticaria, viral cutaneous pathologies such as those derived from human papillomavirus, HIV or RLV infection, bacterial, fungal and other parasital cutaneous pathologies, and cutaneous lupus erythematosus, (5) asthma and respiratory allergic diseases such as allergic asthma, allergic rhinitis, otitis media, allergic conjunctivitis, hypersensitivity lung diseases, chronic obstructive pulmonary disease and the like, (6) autoimmune diseases, such as arthritis (including rheumatoid and psoriatic), systemic lupus erythematosus, type I diabetes, myasthenia gravis, multiple sclerosis, Graves' disease, glomerulonephritis and the like, (7) graft rejection (including allograft rejection and graft-v-host disease), e.g., skin graft rejection, solid organ transplant rejection, bone marrow transplant rejection, (8) fever, (9) cardiovascular disorders such as acute heart failure, hypotension, hypertension, angina pectoris, myocardial infarction, cardiomyopathy, congestive heart failure, atherosclerosis, coronary artery disease, restenosis, thrombosis and vascular stenosis, (10) cerebrovascular disorders such as traumatic brain injury, stroke, ischemic reperfusion injury and aneurysm, (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, (12) fibrosis, connective tissue disease and sarcoidosis, (13) genital and reproductive conditions such as erectile dysfunction, (14) gastrointestinal disorders such as gastritis, ulcers, nausea, pancreatitis and vomiting; (15) neurologic disorders, such as Alzheimer's disease, (16) sleep disorders such as insomnia, narcolepsy, sleep apnea syndrome and Pickwick Syndrome, (17) pain, (18) renal disorders, (19) ocular disorders such as glaucoma, (20) infectious diseases, viral infections such as HIV, and bacterial infections such as sepsis, (21) inflammation, (22) flushing and (23) nasal congestion.

In yet another aspect, the invention provides methods of treating or preventing a disease or disorder mediated, regulated or influenced by Th2 cells, eosinophils, basophils, platelets, Langerhans cells, dendritic cells or mast cells, comprising administering to a subject having such as disease or disorder a therapeutically effective amount of one or more of the subject compounds or compositions.

In yet another aspect, the invention provides methods of treating or preventing a condition or disorder mediated, regulated or influenced by $PGD_2$ and metabolites thereof, such as 13,14-dihydro-15-keto-$PGD_2$ and 15-deoxy-$\Delta^{12,14}$-$PGD_2$, comprising administering to a subject having such as disease or disorder a therapeutically effective amount of one or more of the subject compounds or compositions.

In yet another aspect, the invention provides methods of treating or preventing a disease or disorder responsive to modulation of CRTH2 and/or one or more other $PGD_2$ receptors comprising administering to a subject having such a disease or disorder, a therapeutically effective amount of one or more of the subject compounds or compositions.

In yet another aspect, the invention provides methods of treating or preventing a disease or disorder mediated by CRTH2 and/or one or more other PGD$_2$ receptors comprising administering to a subject having such a condition or disease, a therapeutically effective amount of one or more of the subject compounds or compositions.

In yet another aspect, the invention provides methods of modulating CRTH2 and/or one or more other PGD$_2$ receptors comprising contacting a cell with one or more of the subject compounds or compositions.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention of inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion, urticaria or other conditions or disorders associated with CRTH2 and/or one or more other PGD$_2$ receptors, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per, day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including inflammatory conditions, immune disorders, asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, viral infection, thrombosis, fibrosis, flushing, Crohn's disease, ulcerative colitis, chronic obstructive pulmonary disease, inflammation, pain, conjunctivitis, nasal congestion, urticaria and those pathologies noted above.

Such other agents, or drugs, may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, triamcinolone, dexamethasone, fluticasone, flunisolide and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene antagonists (e.g., zafirlukast, montelukast, montelukast sodium (Singulair®), pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) other PGD$_2$ receptor antagonists, especially DP antagonists; (j) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (k) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (l) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); (m) anti-diabetic agents such as insulin and insulin mimetics, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®), ciglitazone, pioglitazone (Actos®) and englitazone; (n) preparations of interferon beta (interferon β-1α, interferon β-1β); (o) gold compounds such as auranofin and aurothioglucose, (p) TNF inhibitors, e.g., etanercept (Enbrel®), antibody therapies such as orthoclone (OKT3), daclizumab (Zenapax®), basiliximab (Simulect®), infliximab (Remicade®) and D2E6 TNF antibody, (q) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (r) multiple sclerosis therapeutic agents such as interferon β-1β (Betaseron®), interferon β-1α (Avonex®), azathioprine (Imurek®, Imuran®), glatiramer acetate (Capoxone®), a glucocorticoid (e.g., prednisolone) and cyclophosphamide; (s) other compounds such as 5-aminosalicylic acid and prodrugs thereof; (t) DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, hormone therapy (e.g., tamoxifen, and flutamide), and cytostatic agents, e.g., imatinib (ST1571, Gleevec®) and rituximab (Rizuxan®). The weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, preferably about 200:1 to about 1:200. Combinations of a compound of the invention and other active ingredients will generally also be within the aforementioned range, but in each case, an effective dose of each active ingredient should be used.

Analysis of the Compounds

In yet another aspect, the invention includes methods to evaluate putative specific agonists or antagonists of CRTH2 and/or one or more other $PGD_2$ receptors. Accordingly, the invention is directed to the use of these compounds in the preparation and execution of screening assays for compounds which modulate the function of CRTH2 and/or one or more other $PGD_2$ receptors. For example, the compounds of this invention are useful for CRTH2 mutants and/or one or more other $PGD_2$ receptor mutants, which are excellent screening tools for potent compounds. Furthermore, the compounds of this invention are useful in establishing or determining the binding site of other compounds to CRTH2 and/or one or more other $PGD_2$ receptors, e.g., by competitive inhibition. The compounds of the instant invention are also useful for the evaluation of putative specific modulators of CRTH2 and/or one or more other $PGD_2$ receptors. One of skill in the art will appreciate that thorough evaluation of specific agonists and antagonists of $PGD_2$ receptors has been hampered by the lack of availability of non-peptidyl (metabolically resistant) compounds with high binding affinity for these receptors. The compounds provided herein are particularly useful in this context.

High Throughput Screening

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to the assays, which are typically run in parallel (e.g., in microtiter formats on microtiter plates in robotic assays). Preferred assays detect enhancement or inhibition of CRTH2 and/or one or more other $PGD_2$ receptors function.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start-up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

The following examples are offered by way of illustration and are not intended to limit the scope of the invention. Those of skill in the art will readily recognize a variety of noncritical parameters that could be modified to yield essentially similar results.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

Example 1

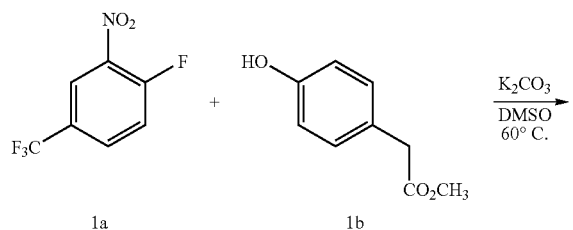

The synthesis of {4-[2-(toluene-4-sulfonylamino)-4-trifluoromethyl-phenoxy]-phenyl}-acetic acid (1) is outlined in Scheme 1 and described below.

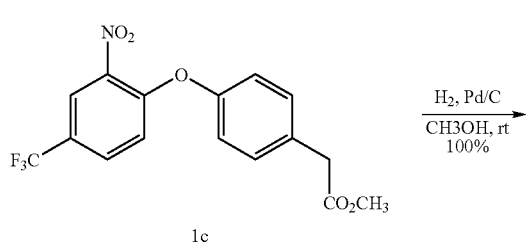

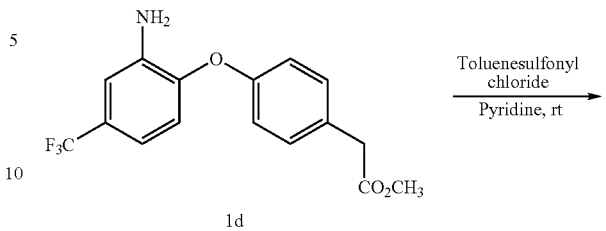

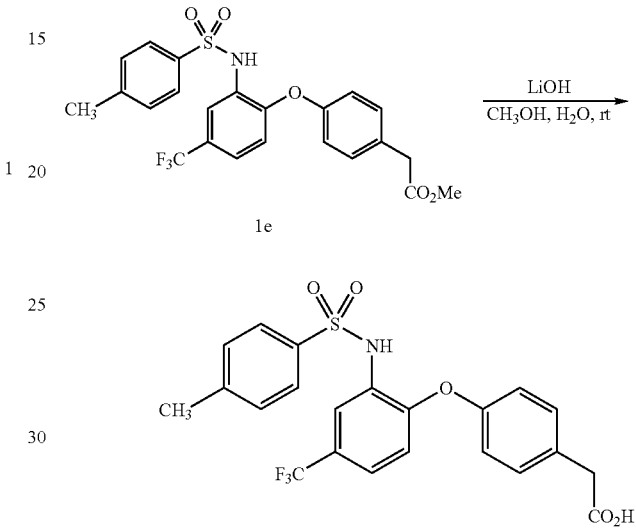

[4-(2-nitro-4-trifluoromethyl-phenoxy)-phenyl]-acetic acid methyl ester (1c). A mixture of 4-fluoro-3-nitrobenzotrifluoride (1a, 1.0 g, 4.78 mmol), methyl 4-hydroxyphenylacetate (1b, 795 mg, 4.78 mmol) and potassium carbonate (661 mg, 4.78 mmol) in 10 mL of DMSO was allowed to stir at 60° C. for 24 h. Upon completion, the mixture was cooled to room temperature and 50 mL of water was added. The resulting mixture was extracted with ethyl acetate (3×30 mL). The combined extracts were washed with water (2×30 mL) and brine, dried over anhydrous sodium sulfate and concentrated in vacuo. The residue was chromatographed on a silica gel column using 20% EtOAc/hexane as the eluent to give 1.31 g of [4-(2-nitro-4-trifluoromethyl-phenoxy)-phenyl]-acetic acid methyl ester. $^1$H NMR (CDCl$_3$): δ 8.22 (d, J=2.00 Hz, 1H), 7.70 (dd, J=8.8, 2.2 Hz, 1H), 7.36 (d, J=8.36 Hz, 2H), 7.08 9s, 1H), 7.07 (d, J=8.48 Hz, 2H).

[4-(2-amino-4-trifluoromethyl-phenoxy)-phenyl]-acetic acid methyl ester (1d). A mixture of [4-(2-nitro-4-trifluoromethyl-phenoxy)-phenyl]-acetic acid methyl ester (1.31 g, 3.54 mmol) and 10% Pd/C (377 mg, 0.354 mmol) in 17 mL of methanol was allowed to stir at room temperature under hydrogen atmosphere for 12 h. Upon completion, the mixture was filtered through a short column of celite and the filtrate was concentrated in vacuo to give 920 mg of [4-(2-Amino-4-trifluoromethyl-phenoxy)-phenyl]-acetic acid methyl ester. $^1$H NMR (CDCl$_3$): δ 7.24-7.33 (m, 3H), 6.80-7.06 (m, 4H), 4.01 (br s, 2H), 3.71 (s, 3H), 3.61 (s, 2H). LCMS (ESI+) 326 (M+1).

{4-[2-(Toluene-4-sulfonylamino)-4-trifluoromethyl-phenoxy]-phenyl}-acetic acid methyl ester (1e). [4-(2-Amino-4-trifluoromethyl-phenoxy)-phenyl]-acetic acid methyl ester (84 mg, 0.542 mmol) was added to a mixture of 150 mg (1.08 mmol) of potassium carbonate in 3 mL of ethyl acetate in presence of 0.5 mL of water. To the resulting mixture was added 155 mg (0.813 mmol) toluenesulfonyl chloride. The resulting mixture was allowed to stir at room temperature overnight. Upon completion, 20 mL of 2N HCl aqueous solution was added and the resulting mixture was extracted with ethyl acetate (3×30 mL). The combined extracts were washed with water and brine, dried over anhydrous sodium sulfate and concentrated in vacuo. The residue was chromatographed to give 97 mg of {4-[2-(toluene-4-sulfonylamino)-4-trifluoromethyl-phenoxy]-phenyl}-acetic acid methyl ester. $^1$H NMR (CDCl$_3$): δ 7.93 (s, 1H), 7.65 (d, J=8.36 Hz, 2H), 7.15-7.28 (m, 5H), 6.68 (d, J=8.68 Hz, 1H), 6.63 9d, J=8.48 Hz, 2H), 3.72 (s, 3H), 3.61 9s, 2H), 2.39 9s, 3H).

{4-[2-(Toluene-4-sulfonylamino)-4-trifluoromethyl-phenoxy]-phenyl}-acetic acid (1). To a solution of {4-[2-(toluene-4-sulfonylamino)-4-trifluoromethyl-phenoxy]-phenyl}-acetic acid methyl ester (97 mg, 0.202 mmol) in 1 mL of methanol was added 1 mL of a suspension of lithium hydroxide (42 mg, 1.01 mmol) in 1 mL of water. The resulting mixture was allowed to stir at room temperature until all starting material disappeared. Upon completion, 50 mL of 1N aqueous HCl was added and the resulting mixture was extracted with ethyl acetate (3×30 mL). The combined extracts were washed with 1N HCl aqueous solution (20 mL), water and brine, dried over anhydrous sodium sulfate and concentrated in vacuo. The residue was purified by column chromatography to give 70 mg of {4-[2-(toluene-4-sulfonylamino)-4-trifluoromethyl-phenoxy]-phenyl}-acetic acid (1). $^1$H NMR (CD$_3$OD): δ 7.84 (d, J=1.92 Hz, 1H), 7.58 (d, J=8.27, 1.6 Hz, 2H). 7.32 (dd, J=8.27, 1.6 Hz, 1H), 7.18-7.30 (m, 5H), 6.73 (d, J=8.53 Hz, 1H), 6.57 (d, J=8.53 Hz, 2H), 3.59 (s, 2H), 2.37 (s, 3H). LCMS (ESI−) 464 (M−1).

Example 2

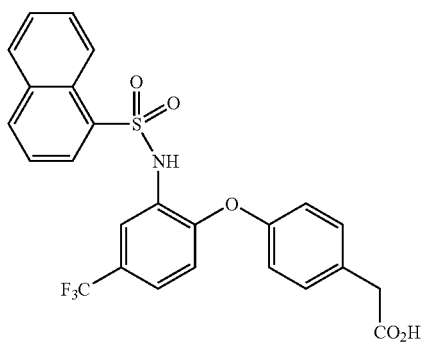

{4-[2-(Naphthalene-1-sulfonylamino)-4-trifluoromethyl-phenoxy]-phenyl}-acetic acid (2) was synthesized using the same synthetic procedures for 1 as shown in Scheme 1. $^1$H NMR (CDCl$_3$): δ 8.60 (d, J=6.67 Hz, 1H), 8.25 (d, J=7.28 Hz, 1H), 8.02 (d, J=8.13 Hz, 1H), 7.80-7.90 (m, 2H), 7.40-7.55 (m, 4H), 7.05-7.15 (m, 3H), 6.53 (d, J=8.60 Hz, 1H), 6.31 (d, J=7.96 Hz, 2H), 3.61 (s, 2H). LCMS (ESI−) 500 (M−1).

Example 3

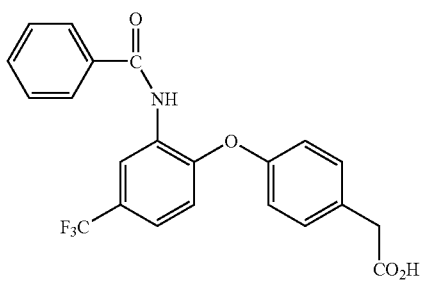

[4-(2-Benzoylamino-4-trifluoromethyl-phenoxy)-phenyl]-acetic acid (3) was synthesized according to the same synthetic procedures for 1 as shown in Scheme 1. $^1$H NMR (CDCl$_3$): δ 8.99 (d, J=1.73 Hz, 1H), 8.61 (s, 1H), 7.84 (d, J=7.76, 2H), 7.45-7.60 (m, 3H), 7.35 (d, J=8.40 Hz, 2H), 7.28 (dd, J=8.72, 1.53 Hz, 1H), 7.08 (d, J=8.44 Hz, 2H), 6.89 (d, J=8.44 Hz, 1H), 3.69 (s, 2H). LCMS (ESI−) 388 (M−1).

Example 4

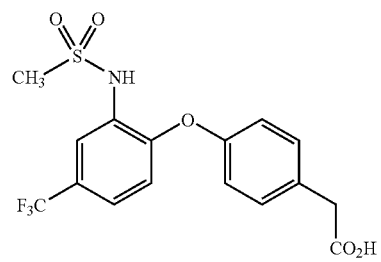

[4-(2-Methanesulfonylamino-4-trifluoromethyl-phenoxy)-phenyl]-acetic acid (4) was synthesized using the same synthetic procedures for 1 as shown in Scheme 1. $^1$H NMR (CDCl$_3$): δ7.89 (d, J=1.76 Hz, 1H), 7.30-7.40 (m, 3H), 7.10 (s, 1H), 7.01 (d, J=8.32 Hz, 2H), 6.89 (d, J=8.48 Hz, 1H), 3.69 (s, 2H), 3.08 (s, 3H). LCMS (ESI−) 388 (M−1).

Example 5

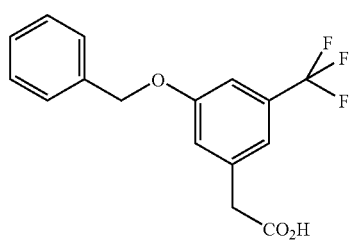

The synthesis of (3-benzyloxy-5-trifluoromethyl-phenyl)-acetic acid (5) is shown in Scheme 2. $^1$H NMR (CDCl$_3$): δ 7.32-7.50 (m, 5H), 7.15 (s, 2H), 7.10 (s, 1H), 5.08 (s, 2H), 3.68 (s, 1H). LCMS (ESI−) 309 (M−1).
Example 6
The synthesis of 3-benzenesulfonylamino-4-(4-carboxymethylphenoxy)-benzoic acid (6) is outlined in Scheme 3, below. $^1$H NMR (CD$_3$OD): δ 8.24 (d, J=2.04 Hz, 1H), 7.68-7.80 (m, 3H), 7.56 (dd, J=7.48, 1.20 Hz, 1H), 7.42 (d, J=7.86 Hz, 1H), 7.40 (d, J=7.76 Hz, 1H), 7.21 (d, J=8.40 Hz, 2H), 6.52-6.68 (m, 3H), 3.58 (s, 2H). LCMS (ESI−) 426 (M−1).
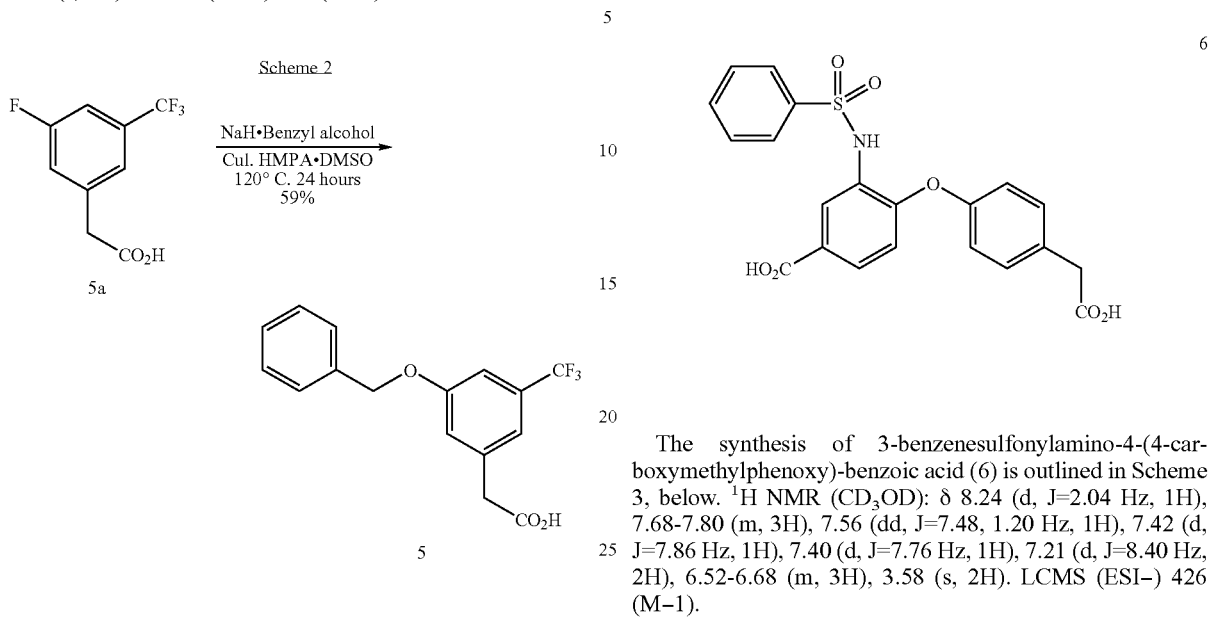
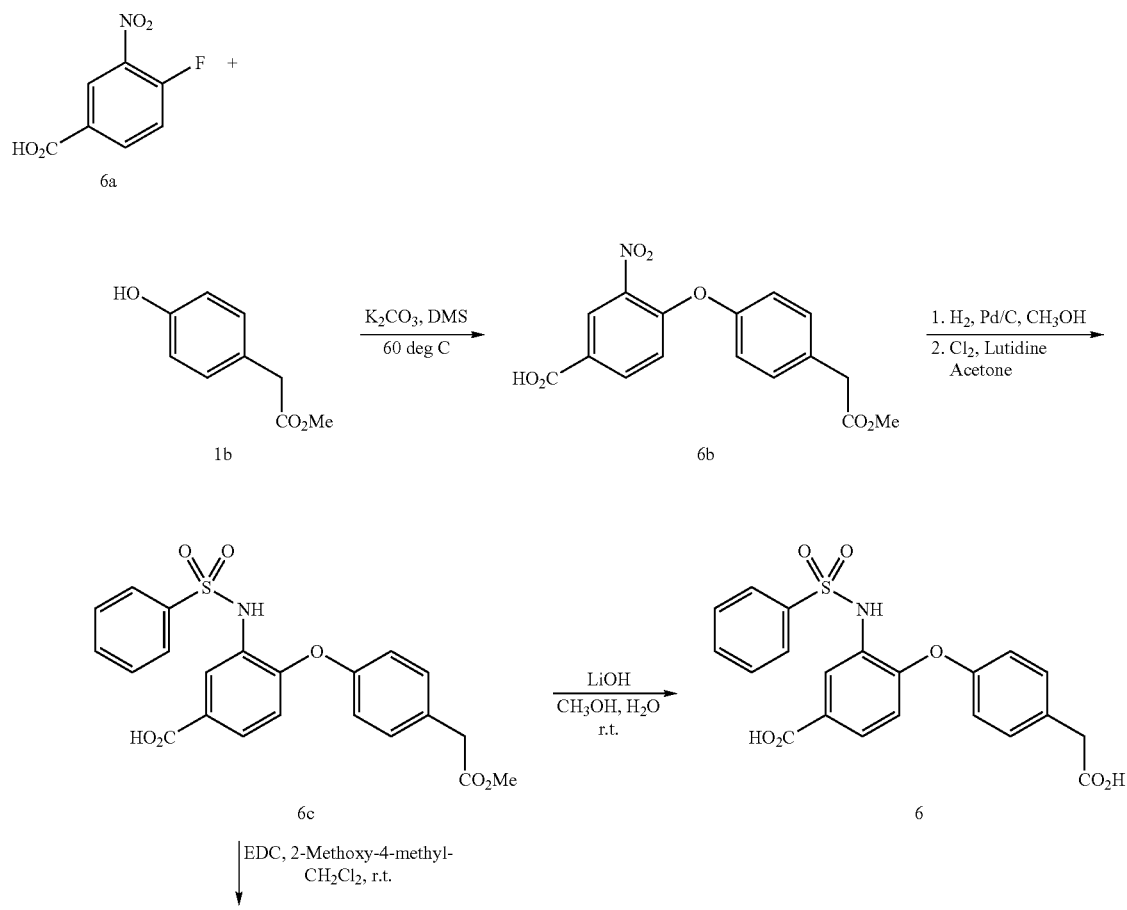

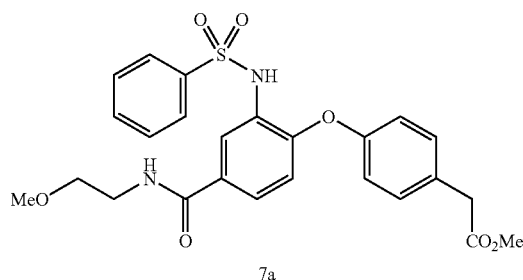

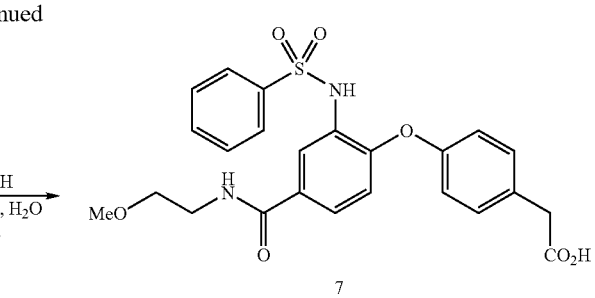

Example 7

The synthesis of 3{4-[2-benzenesulfonylamino-4-(2-methoxy-ethylcarbamoyl)-phenoxy]-phenyl}-acetic acid (7) is outlined in Scheme 3, above. $^1$H NMR (CDCl$_3$): δ 8.01 (d, J=1.72 Hz, 1H), 7.73 (d, J=7.76 Hz, 2H), 7.51 (dd, J=7.76, 7.32 Hz, 2H), 7.38 (dd, J=7.68, 7.68 Hz, 2H), 7.21 (s, 1H), 7.18 (d, J=8.32 Hz, 2H), 6.64 (d, J=8.40 Hz, 2H), 6.55 (d, J=8.18 Hz, 2H), 3.53-3.70 (m, 6H), 3.41 (s, 3H), 1.25 (dd, J=7.07, 7.07 Hz, 3H). LCMS (ESI−) 483 (M−1).

Example 8

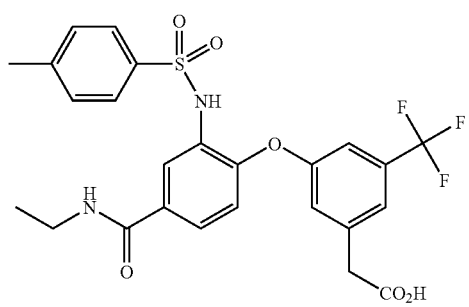

The synthesis of {3-[4-ethylcarbamoyl-2-(toluene-4-sulfonylamino)-phenoxy]-5-trifluoromethyl-phenyl}-acetic acid (8) is shown in Scheme 4, below. $^1$H NMR (CDCl$_3$): δ 7.98 (d, J=2.04 Hz, 1H), 7.55-7.65 (m, 3H), 7.33 (s, 1H), 7.16 (d, J=8.12 Hz, 2H), 7.11 (s, 1H), 6.91 (s, 1H), 6.68 (dd, J=8.36, 2.48 Hz, 2H), 6.25 (br s, 1H), 3.65 (s, 2H), 4.50 (m, 2H), 1.30 (dd, J=7.20, 7.20 Hz, 3H). LCMS (ESI−) 535 (M−1).

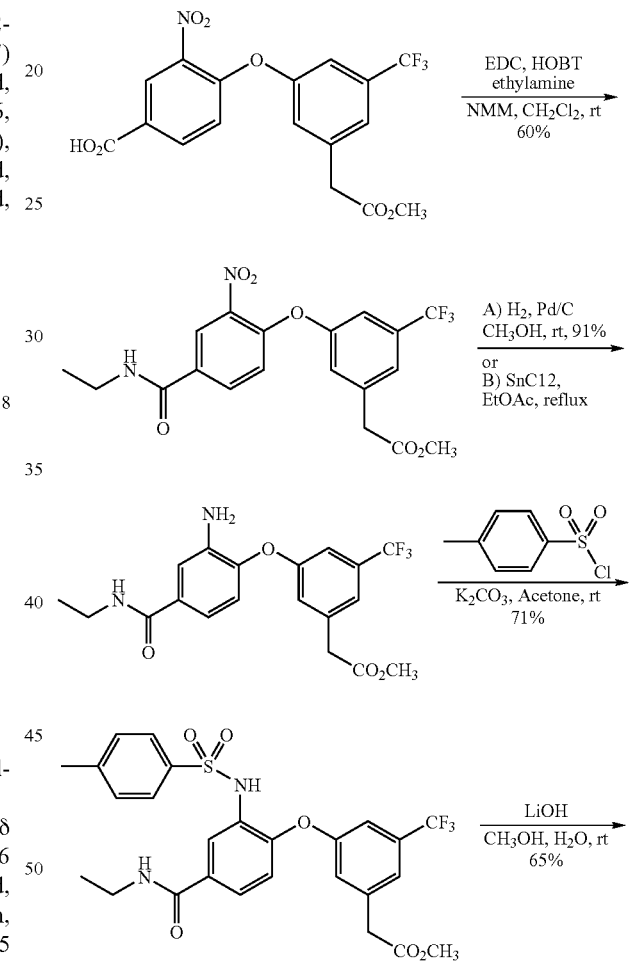

Scheme 4

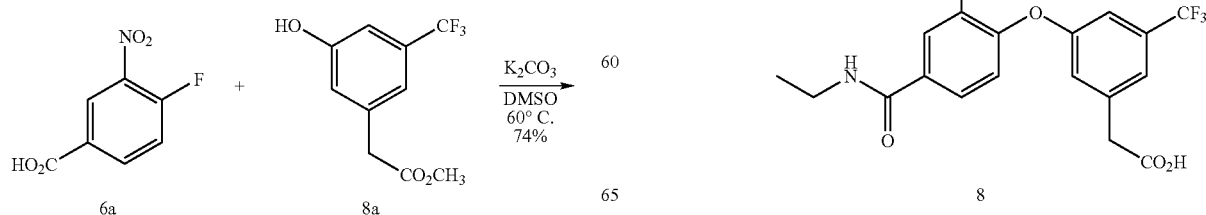

Example 9

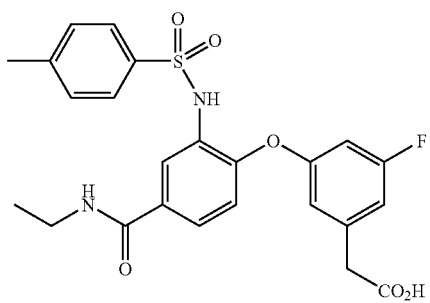

{3-[4-Ethylcarbamoyl-2-(toluene-4-sulfonylamino)-phenoxy]-5-fluoro-phenyl}-acetic acid (9) was synthesized from 3-fluoro-5-hydroxyphenylacetic acid methyl ester according to Scheme 4, above. $^1$H NMR (CDCl$_3$): δ 8.02 (d, J=2.13 Hz, 1H), 7.60 (dd, J=8.60, 2.18 Hz, 1H), 7.57 (d, J=8.57 Hz, 2H), 7.23 (s, 1H), 7.15 (d, J=7.96 Hz, 2H), 6.79 (d, J=8.80 Hz, 1H), 6.73 (d, J=8.56 Hz, 1H), 6.33 (s, 1H), 6.43 (dd, J=5.50, 5.44 Hz, 1H), 5.96 (ddd, J=9.46, 8.53, 2.20 Hz, 1H), 3.59 (s, 2H), 3.52 (m, 2H), 2.37 (s, 3H), 1.26 (dd, J=7.20, 7.20 Hz, 3H). LCMS (ESI−) 485 (M−1).

Example 10

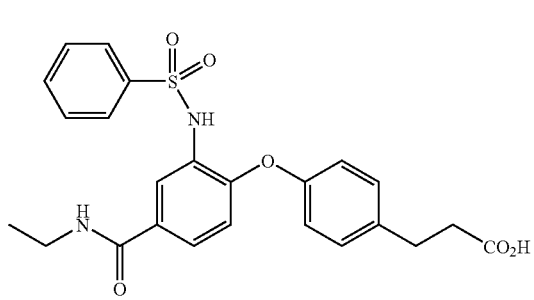

3-[4-(2-Benzenesulfonylamino-4-ethylcarbamoyl-phenoxy)-phenyl]-propionic acid (10) was synthesized from 3-(4-hydroxyphenyl)propionic acid, using benzenesulfonyl chloride, according to Scheme 4, above. $^1$H NMR (CDCl$_3$): δ 8.0 (d, J=2.14 Hz, 1H), 7.74 (dd, J=8.37, 1.27 Hz, 2H), 7.57 (ddd, J=8.58, 7.46, 2.24 Hz, 2H), 7.39 (dd, J=8.26, 7.46 Hz, 2H), 7.18 (s, 1H), 7.12 (d, J=8.60 Hz, 2H), 6.63 (d, J=8.53 Hz, 1H), 6.50 (d, J=8.53 Hz, 2H), 6.22 (br s, 1H), 3.52 (m, 2H), 2.95 (dd, J=7.46, 7.46 Hz, 2H), 2.71 (dd, J=7.46, 7.46 Hz, 2H), 1.28 (dd, J=7.33, 7.33 Hz, 3H). LCMS (ESI−) 467 (M−1).

Example 11

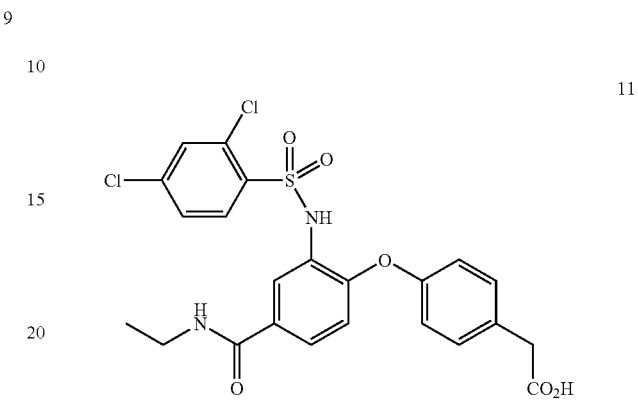

{4-[2-(2,4-Dichloro-benzenesulfonylamino)-4-ethylcarbamoyl-phenoxy]-phenyl}-acetic acid (11) was synthesized from 4-hydroxyphenylacetic acid, using 2,4-dichlorobenzenesulfonyl chloride, according to Scheme 4, above. $^1$H NMR (CDCl$_3$): δ 7.93 (obscured d, J=1.54 Hz, 1H), 7.92 (obscured dd, J=8.13, 0.61 Hz, 1H), 7.80 (br s, 1H), 7.69 (s, 1H), 7.52 (dd, J=8.57, 2.18 Hz, 1H), 7.45 (m, 1H), 7.30 (dd, J=8.13, 2.02 Hz, 1H), 7.25 (d, J=8.68 Hz, 2H), 6.74 (d, J=8.58 Hz, 1H), 6.69 (dd, J=8.64, 2.02 Hz, 2H), 6.28 (br s, 1H), 3.68 (s, 2H), 3.50 (m, 2H), 1.27 (dd, J=7.46, 7.46 Hz, 3H). LCMS (ESI−) 521 (M−1).

Example 12

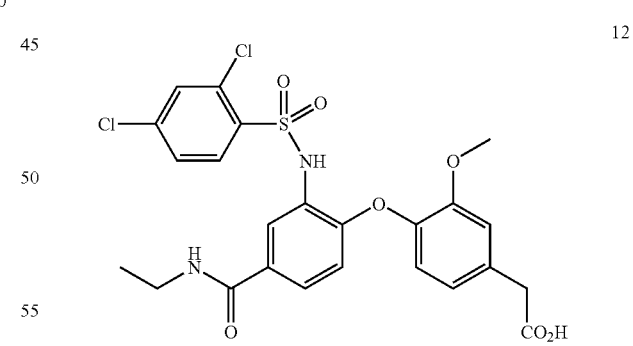

(4-[2-(2,4-Dichloro-benzenesulfonyl-amino)-4-ethylcarbamoyl-phenoxy]-3-methoxy-phenyl)-acetic acid (12) was prepared using 2,4-dichlorobenzenesulfonyl chloride, according to Scheme 4. $^1$H NMR (CDCl$_3$): δ 7.96 (d, J=8.40 Hz, 1H), 7.88 (s, 1H), 7.83 (s, 1H), 7.45 (dd, J=8.56, 1.84 Hz, 1H), 7.39 (d, J=1.84 Hz, 1H), 7.30 (dd, J=8.56, 1.92 Hz, 1H), 6.91 (s, 1H), 6.82 (d, J=8.04 Hz, 1H), 6.69 (d, J=8.12 Hz, 1H), 6.55 (d, J=8.44 Hz, 1H), 6.15 (br s, 1H), 3.67 (s, 3H), 3.65 (s, 2H), 3.46 (m, 2H), 1.24 (dd, J=7.20, 7.20 Hz, 3H). LCMS (ESI−) 551 (M−1).

Example 13

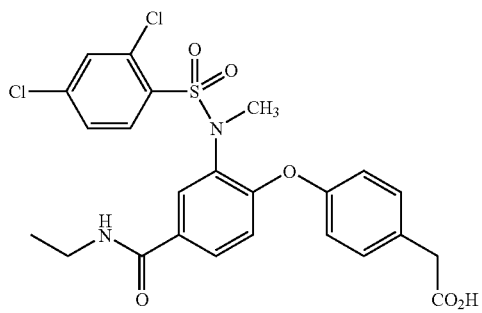

13

(4-{2-[(2,4-Dichloro-benzenesulfonyl)-methyl-amino]-4-ethylcarbamoyl-phenoxy}-phenyl)-acetic acid (13) was prepared from 4-hydroxyphenylacetic acid, using 2,4-dichlorobenzenesulfonyl chloride, according to Scheme 4. $^1$H NMR (CDCl$_3$): δ 7.72-7.83 (m, 3H), 7.17-7.26 (m, 4H), 6.77 (d, J=8.80 Hz, 1H), 6.60 (d, J=8.44 Hz, 2H), 6.23 (br s, 1H), 3.64 (s, 2H), 3.51 (s, 3H), 3.48 (m, 2H), 1.26 (dd, J=7.33, 7.33 Hz, 3H). LCMS (ESI−) 536 (M−1).

Example 14

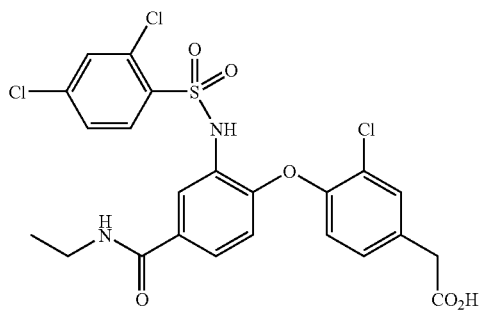

14

{3-Chloro-4-[2-(2,4-dichloro-benzenesulfonylamino)-4-ethylcarbamoyl-phenoxy]-phenyl}-acetic acid (14) was prepared using 2,4-dichlorobenzenesulfonyl chloride, according to Scheme 4. $^1$H NMR (CDCl$_3$): δ 7.94 (d, J=8.56 Hz, 1H), 7.93 (s, 1H), 7.73 (s, 1H), 7.50 (dd, J=8.60, 2.16 Hz, 1H), 7.41 (d, J=1.48 Hz, 1H), 7.36 (d, J=8.48 Hz, 1H), 7.11 (dd, J=8.32, 1.60 Hz, 1H), 6.62 (d, J=8.36 Hz, 1H), 6.55 (d, J=8.72 Hz, 1H), 3.65 (s, 2H), 3.47 (m, 2H), 1.23 (dd, J=7.20, 7.20 Hz, 3H). LCMS (Neg) 556 (M−1).

Example 15

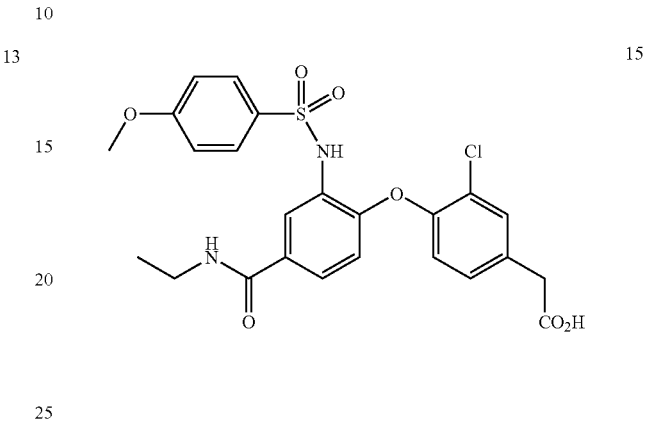

15

{3-Chloro-4-[4-ethylcarbamoyl-2-(4-methoxy-benzenesulfonyl-amino)-phenoxy]-phenyl}-acetic acid (15) was prepared according to Scheme 4. $^1$H NMR (CDCl$_3$): δ 7.99 (d, J=1.44 Hz, 1H), 7.68 (d, J=8.88 Hz, 2H), 7.53 (dd, J=8.60, 1.44 Hz, 1H), 7.35 (s, 1H), 7.26 (s, 1H), 7.08 (dd, J=8.32, 1.36 Hz, 1H), 6.83 (d, J=8.80 Hz, 2H), 6.55 (d, J=8.40 Hz, 1H), 6.48 (d, J=8.56 Hz, 1H), 6.38 (br s, 1H), 3.80 (s, 3H), 3.61 (s, 2H), 3.48 (m, 2H), 1.25 (dd, J=7.20, 7.20 Hz, 3H). LCMS (ESI−) 517 (M−1).

Example 16

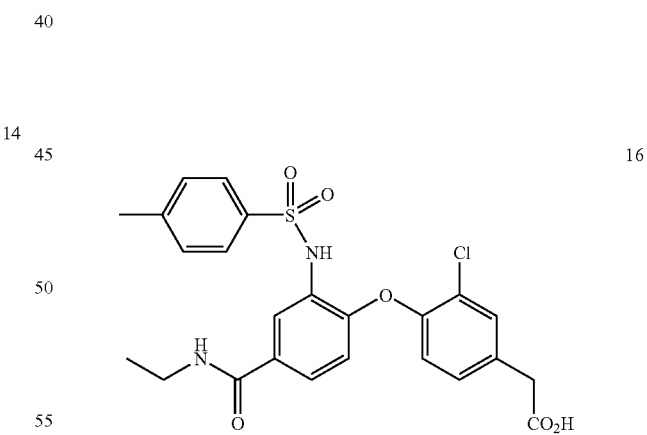

16

{3-Chloro-4-[4-ethylcarbamoyl-2-(toluene-4-sulfonylamino)-phenoxy]-phenyl}-acetic acid (16) was prepared using toluenesulfonyl chloride, according to Scheme 4. $^1$H NMR (CDCl$_3$): δ 7.98 (d, J=2.12 Hz, 1H), 7.63 (d, J=8.32 Hz, 2H), 7.54 (dd, J=8.60, 2.16 Hz, 1H), 7.35 (d, J=1.92 Hz, 1H), 7.25 (s, 1H), 7.17 (d, J=8.40 Hz, 2H), 7.08 (dd, J=8.32, 1.96 Hz, 1H), 6.52 (d, J=8.32 Hz, 1H), 6.46 (d, J=8.52 Hz, 1H), 6.30 (br s, 1H), 3.62 (s, 2H), 3.52 (m, 2H), 2.36 (s, 3H), 1.25 (dd, J=7.20, 7.20 Hz, 3H). LCMS (ESI−) 501 (M−1).

Example 17

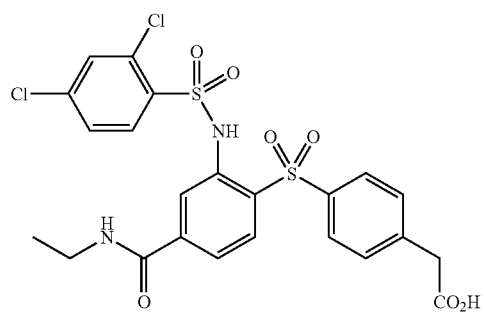

Synthesis of {4-[2-(2,4-dichloro-benzenesulfonyl-amino)-4-ethylcarbamoyl-benzenesulfonyl]-phenyl}-acetic acid (17) is shown in Scheme 5. $^1$H NMR (CDCl$_3$): δ 9.85 (S, 1H), 9.77 (s, 1H), 7.35-8.20 (m, 24H), 6.07 (br s, 2H), 3.75 (s, 4H), 3.35-3.50 (m, 4H), 1.25 (dd, J=5.4, 5.4 Hz, 3H). 1.23 (dd, J=7.20, 7.20 Hz, 3H). LCMS (ESI−) 570 (M−1).

Scheme 5

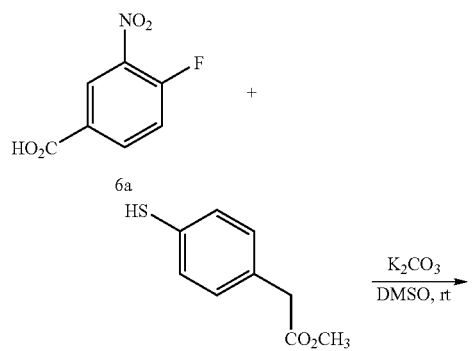

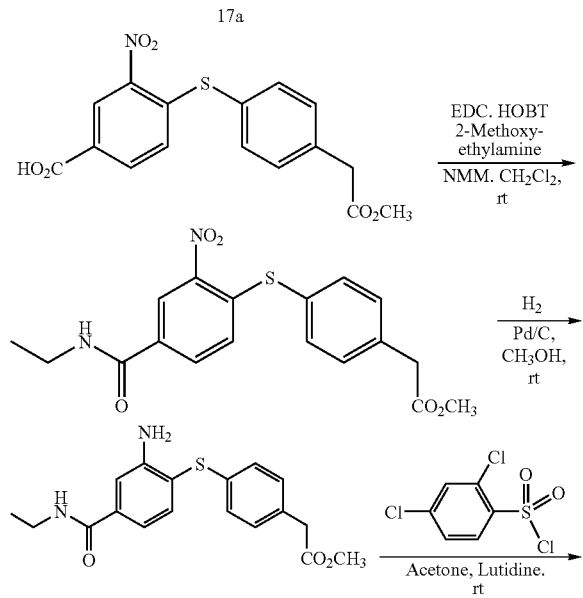

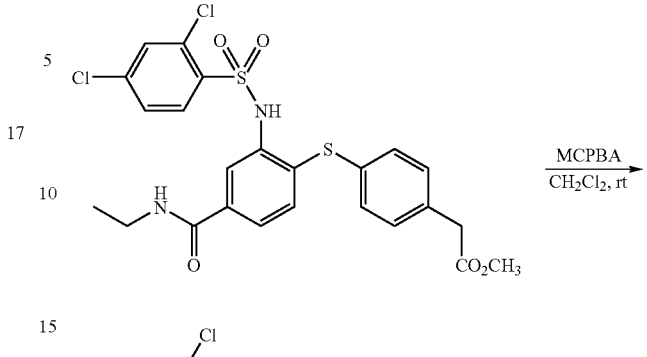

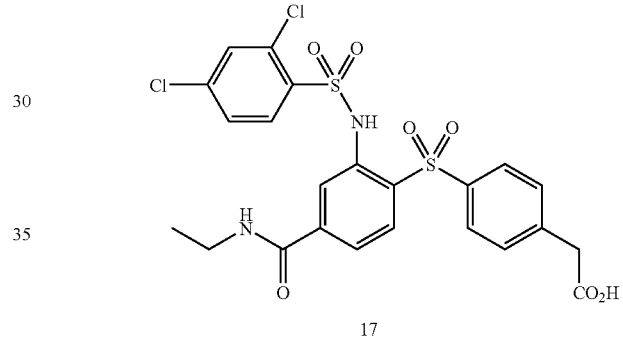

Example 18

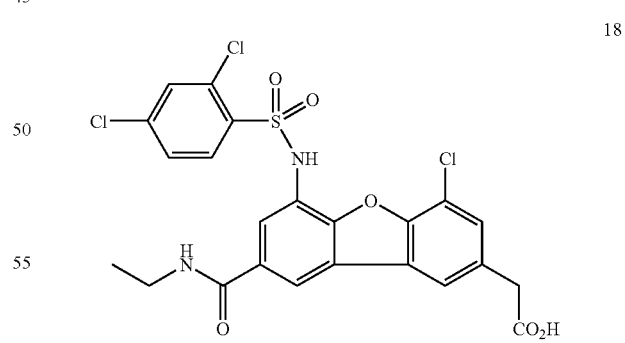

The synthesis of [4-chloro-6-(2,4-dichloro-benzenesulfonyl-amino)-8-ethylcarbamoyl-dibenzofuran-2-yl]-acetic acid (18) is shown in Scheme 6. $^1$H NMR (CD$_3$OD): δ 8.42 (s, 1H), 8.08 (s, 1H), 7.96 (s, 1H), 7.95 (d, J=7.40 Hz, 1H), 7.4 (d, J=1.92 Hz, 1H), 7.57 (s, 1H), 7.40 (dd, J=7.4, 2.04 Hz, 1H), 3.85 (s, 2H), 3.53 (m, 2H), 1.34 (dd, J=7.33, 7.33 Hz, 3H). LCMS (ESI−) 554 (M−1).

Scheme 6

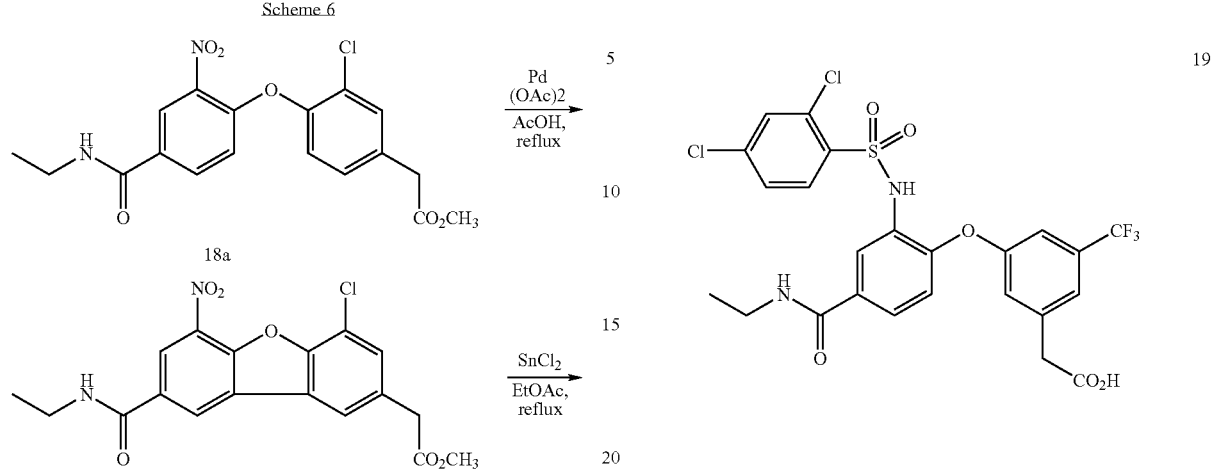

Example 19

{3-[2-(2,4-Dichloro-benzenesulfonyl-amino)-4-ethylcarbamoyl-phenoxy]-5-trifluoromethyl-phenyl}-acetic acid (19) was prepared from 3-hydroxy-5-trifluoromethylphenylacetic acid, using 2,4-dichlorobenzenesulfonyl chloride, according to Scheme 4. $^1$H NMR (Acetone-$d_6$): δ 9.10 (br s, 1H), 8.11 (d, J=2.04 Hz, 1H), 7.90 (d, J=8.40 Hz, 1H), 7.83 (br s, 1H), 7.72 (dd, J=8.48, 2.16 Hz, 1H), 7.46 (s, 2H), 7.43 (d, J=2.04 Hz, 1H), 7.03 (s, 1H), 6.96 (d, J=8.64 Hz, 1H), 6.92 (s, 1H), 3.78 (s, 2H), 3.42 (m, 2H), 1.19 (dd, J=7.28, 7.28 Hz, 3H). LCMS (ESI−) 590 (M−1).

Example 20

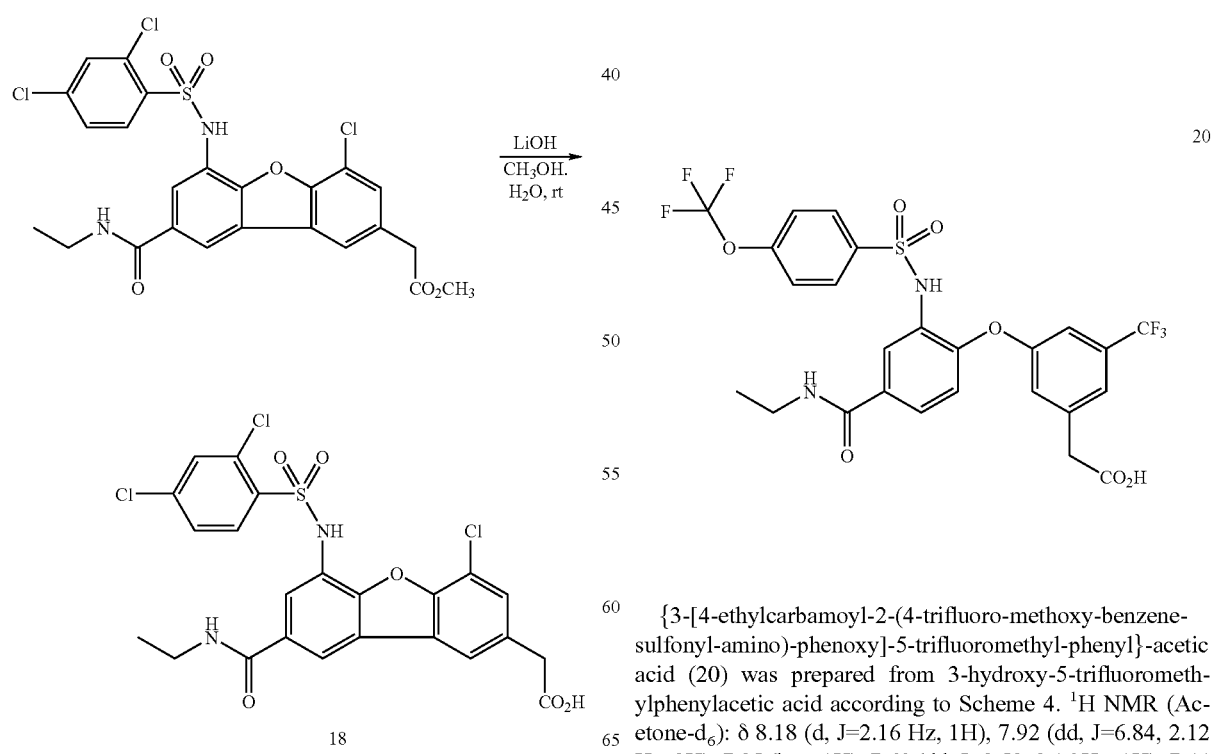

{3-[4-ethylcarbamoyl-2-(4-trifluoro-methoxy-benzenesulfonyl-amino)-phenoxy]-5-trifluoromethyl-phenyl}-acetic acid (20) was prepared from 3-hydroxy-5-trifluoromethylphenylacetic acid according to Scheme 4. $^1$H NMR (Acetone-$d_6$): δ 8.18 (d, J=2.16 Hz, 1H), 7.92 (dd, J=6.84, 2.12 Hz, 2H), 7.85 (br s, 1H), 7.69 (dd, J=8.52, 2.16 Hz, 1H), 7.44 (d, J=8.04 Hz, 1H), 7.42 (d, J=8.04 Hz, 1H), 7.05 (s, 1H), 6.90

(d, J=8.56 Hz, 1H), 6.87 (s, 1H), 3.75 (s, 2H), 3.42 (m, 2H), 1.19 (dd, J=7.24, 7.24 Hz, 3H). LCMS (ESI−) 605 (M−1).

Example 21

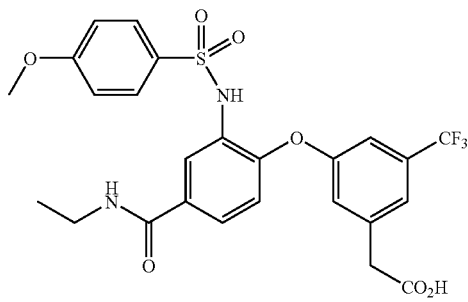

{3-[4-Ethylcarbamoyl-2-(4-methoxy-benzenesulfonylamino)-phenoxy]-5-trifluoromethyl-phenyl}-acetic acid (21) was prepared from 3-hydroxy-5-trifluoromethylphenylacetic acid according to Scheme 4. $^1$H NMR (Acetone-d$_6$): δ 10.5 (br s, 1H), 8.81 (s, 1H), 8.20 (d, J=2.12 Hz. 1H), 7.82 (br s. 1H), 7.63-7.70 (m, 3H), 7.45 (S, 1H), 6.86-6.97 (M, 5H), 3.82 (S, 3H), 3.75 (S, 2H). 3.43 (M, 2H), 1.20 (dd, J=7.20, 7.20 Hz, 3H). LCMS (ESI−) 551 (M−1).

Example 22

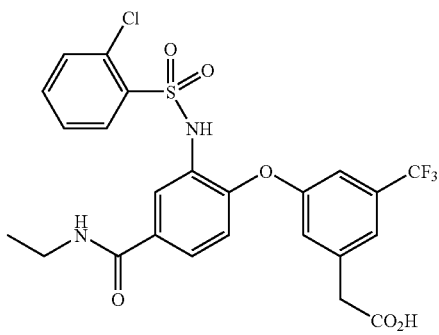

{3-[2-(2-Chloro-benzenesulfonylamino)-4-ethylcarbamoyl-phenoxy]-5-trifluoromethyl-phenyl}-acetic acid (22) was prepared from 3-hydroxy-5-trifluoromethylphenylacetic acid, using 2-chlorobenzenesulfonyl chloride, according to Scheme 4. $^1$H NMR (Acetone-14): δ 10.5 (br s, 1H), 8.93 (s, 1H), 8.12 (d, J=1.59 Hz, 1H), 7.94 (dd, J=8.40, 1.96 Hz, 1H), 7.81 (br s, 1H), 7.67 (dd, J=8.56, 2.16 Hz, 1H), 7.40-7.52 (m, 4H), 7.00 (s, 1H), 6.90 (obscured d, J=8.56 Hz, 1H), 6.90 (s, 1H), 3.76 (s, 2H), 3.41 (m, 2H), 1.19 (dd, J=7.20, 7.20 Hz, 3H). LCMS (ESI−) 555 (M−1).

Example 23

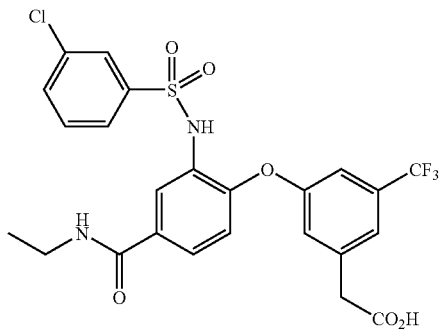

{3-[2-(4-Chloro-benzenesulfonylamino)-4-ethylcarbamoyl-phenoxy]-5-trifluoromethyl-phenyl}-acetic acid (23) was prepared from 3-hydroxy-5-trifluoromethylphenylacetic acid, using 4-chlorobenzenesulfonyl chloride, according to Scheme 4. $^1$H NMR (Acetone-d6): δ 10.5 (br s, 1H), 9.09 (S, 1H), 8.18 (d, J=2.16 Hz, 1H), 7.85 (br s, 1H), 7.68-7.77 (m, 3H), 7.40-7.50 (m, 3H), 6.98 (s. 1H). 6.91 (obscured d, J=8.48, 1H), 6.90 (s, 1H), 3.77 (s, 2H), 3.43 (m, 2H), 1.20 (dd, J=7.24, 7.24 Hz, 3H). LCMS (ESI−) 555 (M−1).

Example 24

{3-[2-(3-Chloro-benzenesulfonylamino)-4-ethylcarbamoyl-phenoxy]-5-trifluoromethyl-phenyl}-acetic acid (24) was synthesized from 3-hydroxy-5-trifluoromethylphenylacetic acid, using 3-chlorobenzenesulfonyl chloride, according to Scheme 4. $^1$H NMR (Acetone-d$_6$): δ 10.5 (br s, 1H), 9.19 (s, 1H), 8.19 (d, J=2.18 Hz, 1H), 7.99 (s, 1H), 7.82 (d, J=1.89 Hz, 1H), 7.55-7.74 (m, 3H), 7.50 (dd, J=7.89, 2.24 Hz, 1H), 7.48 (d, J=8.12 Hz, 1H), 6.98 (s, 1H), 6.91 (dd, J=8.56, 2.29 Hz, 1H), 6.86 (s, 1H), 3.78 (s, 2H), 3.44 (m, 2H), 1.21 (dd, J=7.20, 7.20 Hz, 3H). LCMS (ESI−) 555 (M−1).

Example 25

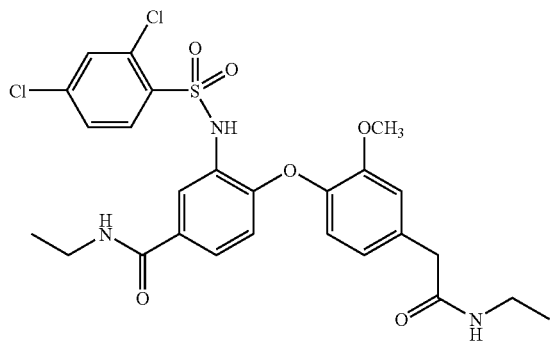

25

Synthesis of 3-(2,4-Dichloro-benzenesulfonylamino)-N-ethyl-4-(4-ethylcarbamoylmethyl-2-methoxy-phenoxy)-benzamide (25). A mixture of acid (12) (63 mg, 0.114 mmol), EDC (44 mg, 0.228 mmol), HOBt (18 mg, 0.114 mmol), 114 μL of 2N ethylamine in THF (0.228 mmol) in 1 mL of methylene chloride was allowed to stir for 24 h at room temperature. Upon completion, the solvent was removed and 10 mL of 2N HCl aqueous solution was added and the resulting mixture was extracted with EtOAc (4×20 mL). The combined extracts were washed with water and brine, dried over anhydrous sodium sulfate and concentrated. The residue was purified by column chromatography on a silica gel column using 50% EtOAc/hexane and EtOAc sequentially as the eluents to give 53.0 mg of the title compound. $^1$H NMR (CDCl$_3$): δ 7.96 (d, J=8.52 Hz, 1H), 7.87 (d, J=2.08 Hz, 1H), 7.83 (br s, 1H), 7.42 (obscured dd, J=8.52, 2.16 Hz, 1H), 7.40 (s, 1H), 7.29 (dd, J=8.12, 2.20 Hz, 1H), 6.90 (d, J=1.72 Hz, 1H), 6.77 (d, J=8.20 Hz, 1H), 6.76 (s, 1H), 6.72 (d, J=8.08 Hz, 1H), 6.54 (d, J=8.52 Hz, 1H), 6.17 (br s, 1H), 5.62 (br s, 1H), 3.67 (s, 3H), 3.52 (s, 2H), 3.45 (m, 2H), 3.29 (m, 2H), 1.23 (dd, J=7.48, 7.48 Hz, 3H), 1.12 (dd, J=7.52, 7.52 Hz, 3H). LCMS (ESI−) 579 (M−1).

Example 26

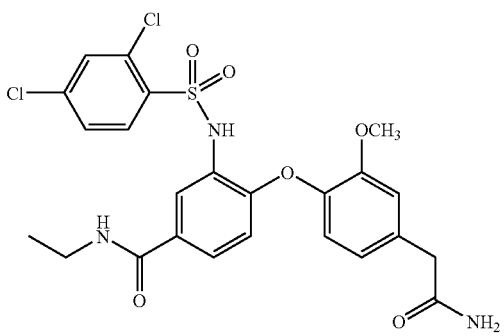

26

Synthesis of 4-(4-Carbamoylmethyl-2-methoxy-phenoxy)-3-(2,4-dichloro-benzenesulfonylamino)-N-ethyl-benzamide (26). A mixture of acid 12 (70 mg, 0.126 mmol) and urea (1.0 g, 16.6 mmol) was heated to 170-180° C. and maintained at this temperature for 4 h, and the mixture was allowed to cool. As soon as the temperature dropped to 110-120° C. 2 mL of 5% sodium carbonate aqueous solution was added, and the mixture was shaken vigorously. After mixture was cooled to room temperature, 20 mL of 3N HCl aqueous solution was added and the resulting mixture was extracted with ethyl acetate (4×20 mL). The combined extracts were washed with water and brine, dried and concentrated. The residue was purified by silica gel chromatography using EtOAc and 10% CH$_3$OH/EtOAc sequentially as the eluents to give 47 mg of product. $^1$H NMR (Acetone-d$_6$): δ 8.77 (s, 1H), 8.04 (d, J=2.13 Hz, 1H), 7.96 (d, J=8.57 Hz, 1H), 7.70 (, br s, 1H), 7.63 (d, J=2.13 Hz, 1H), 7.56 (dd, J=8.53, 2.13 Hz, 1H), 7.51 (dd, J=8.53, 2.13 Hz, 1H), 7.11 (d, J=1.86 Hz, 1H), 6.88 (dd, J=8.13, 1.87 Hz, 1H), 6.85 (br s, 1H), 6.75 (d, J=8.13 Hz, 1H), 6.659 (d, J=8.67 Hz, 1H), 3.67 (s, 3H), 3.51 (s, 2H), 3.38 (m, 2H), 1.17 (dd, J=7.20, 7.20 Hz, 3H). LCMS (ESI−) 551 (M−1).

Example 27

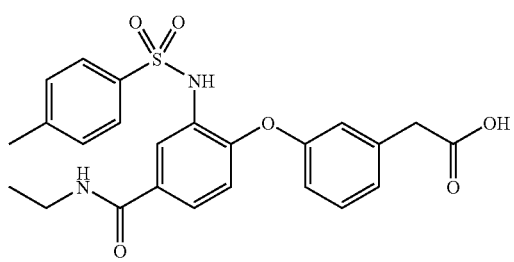

27

Compound 27 was prepared according to Scheme 7, below.

Scheme 7

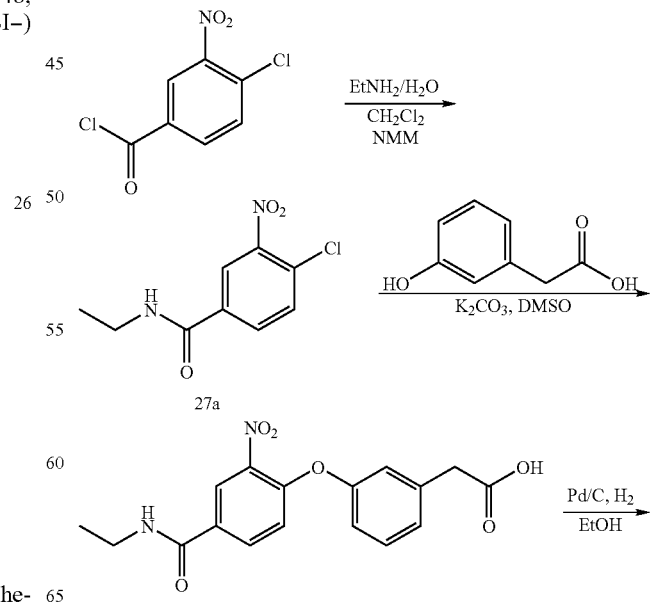

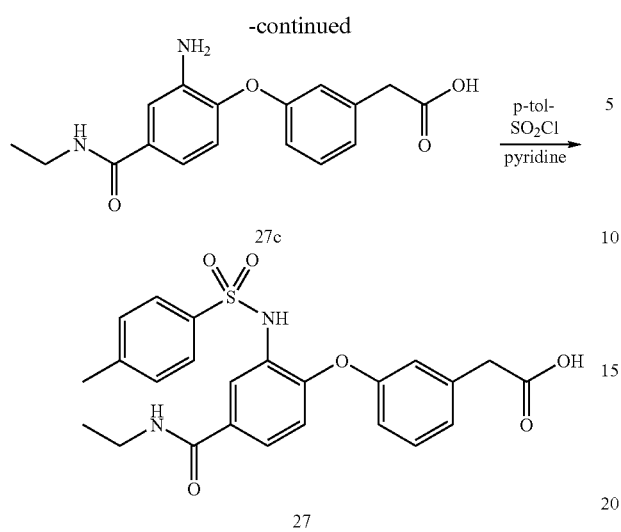

4-Chloro-3-nitro-N-ethyl-benzamide (27a). To a solution of 4-chloro-3-nitrobenzoylchloride (2.2 g, 10 mmol, 1.0 equiv.) and N-methylmorpholine (1.65 mL, 15 mmol, 1.5 equiv.) in 20 mL of dichloromethane was added dropwise a 70% aqueous solution of ethylamine (1.62 mL, 20 mmol, 2.0 equiv.). The mixture was stirred for 1 h, and poured into 40 mL of 10% citric acid. The aqueous layer was extracted with 20 mL of dichloromethane. The combined organic extracts were washed with brine, dried over sodium sulfate, and evaporated in vacuo to give 2.1 g of a yellow solid as product. $^1$H-NMR (DMSO-$d_6$): δ 8.83 (t, J=4.0 Hz, 1H), 8.50 (d, J=2.4 Hz, 1H), 8.14 (dd, $J_1$=8.4 Hz, $J_2$=2.0 Hz, 1H), 7.91 (d, J=8.4 Hz, 1H), 3.31 (m, 2H). 1.14 (t, J=7.2 Hz, 3H). MS (ESI): 229.1 (M+H).

3-(4-Ethylcarbamoyl-2-nitrophenoxy)-phenylacetic acid (27b) To a solution of 27a (229 mg, 1.0 mmol, 1.0 equiv.) and 3-hydroxyphenylacetic acid (152 mg, 1.0 mmol, 1.0 equiv.) in 2 mL of DMSO, was added $K_2CO_3$ powder (414 mg, 3.0 mmol, 3.0 equiv.). The mixture was heated in an 100° C. oil bath for 8 h. After cooling to room temperature, the mixture was poured into 15 mL of 10% aqueous citric acid. After extracting twice with 10 mL of EtOAc, the combined organic extracts were washed with brine, dried over $Na_2SO_4$, and concentrated in vacuo to give a brown solid, which was used without further purification in the subsequent step. $^1$H-NMR (DMSO-$d_6$): δ 12.41 (br s, 1H), 8.74 (t, J=6.0 Hz, 1H), 8.54 (s, 1H), 8.13 (d, J=12 Hz, 1H), 7.41 (t, J=8.0 Hz, 1H), 7.20-7.12 (m, 2H), 7.11-7.01 (m, 2H), 3.62 (s, 2H), 3.31 (m, 2H), 1.13 (t, J=6.0 Hz, 3H). MS (ESI-): 343.1 (M−H).

3-(4-Ethylcarbamoyl-2-aminophenoxy)-phenylacetic acid (27c). To a solution of the product obtained above in 5 mL of EtOH, was added 5% Pd on carbon (43 mg, 0.02 mmol, 0.02 equiv.). The mixture was stirred vigorously under a $H_2$ atmosphere. After 27b was completely consumed, the mixture was diluted with 10 mL of EtOAc and filtered through Celite. The filtrate was concentrated in vacuo to give a brown residue, which was purified by silica gel chromatography to give 27c as an off-white solid. $^1$H-NMR (DMSO-$d_6$): δ 12.3 (br s, 1H), 8.26 (t, J=5.3 Hz, 3H), 7.30 (t, J=7.8 Hz, 2H), 7.00 (m, 2H), 6.88 (s, 1H), 6.82 (m, 1H), 6.77 (d, J=8.3 Hz. 1H), 5.12 (br s, 2H), 3.62 (s, 2H), 3.24 (m, 2H), 1.11 (t, J=7.2 Hz, 3H). MS (ESI-): 313.1 (M−H).

3-(4-Ethylcarbamoyl-2-p-toluenesulfonylamino-phenoxy)phenylacetic acid (27) To a solution of 27c (100 mg, 0.32 mmol, 1.0 equiv.) in 0.5 mL of pyridine, was added p-toluenesulfonyl chloride (73 mg, 0.38 mmol, 1.2 equiv.). The mixture was stirred at room temperature for 4 h, and partitioned between 15 mL of EtOAc and 20 mL of 10% aqueous citric acid. The organic layer was washed with brine, dried over $Na_2SO_4$, and concentrated in vacuo to give a brown solid. The product was purified by silica gel chromatography to give 63 mg of 27 as a white solid. $^1$H-NMR (DMSO-$d_6$): δ 12.38 (br s, 1H), 9.99 (s, 1H), 8.43 (t, J=6.0 Hz, 1H), 7.93 (s, 1H), 7.69-7.65 (m, 3H), 7.29-7.23 (m, 3H), 6.63 (d, J=8.0 Hz, 1H), 6.52 (s, 1H), 6.47 (d, J=8.0 Hz, 1H), 3.53 (s, 2H), 3.25 (m, 2H), 2.33 (s, 3H), 1.10 (t, J=8.0 Hz, 3H). MS (ESI-): 467.2 (M−H).

Example 28

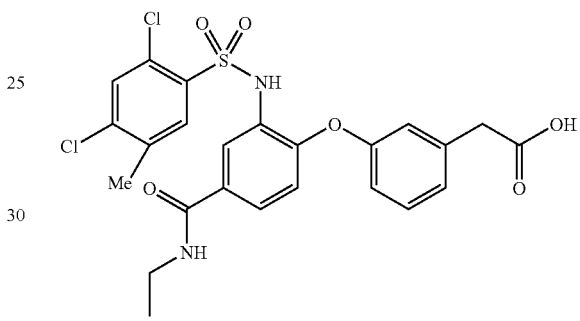

3-[4-Ethylcarbamoyl-2-(2,4-dichloro-5-methylphenylsulfonyl)amino-phenoxy]phenylacetic acid (28) was prepared following the procedure described for 27 above. $^1$H-NMR (DMSO-$d_6$): δ 12.38 (br s, 1H), 10.24 (s, 1H), 8.49 (t, J=6.0 Hz, 1H), 7.91 (s, 1H), 7.74 (s, 1H), 7.66 (d, J=8.0 Hz, 1H), 7.50 (s, 1H), 7.20 (t, J=8.0 Hz, 1H), 7.01 (d, J=8.0 Hz, 1H), 6.75 (d, J=8.0 Hz, 1H), 6.55 (s, 1H), 6.44 (d, J=8.0 Hz, 1H), 3.52 (s, 2H), 3.26 (m, 2H), 2.20 (s, 3H), 1.11 (t, J=6.0 Hz, 3H). MS (ESI-): 535.1 (M−H).

Example 29

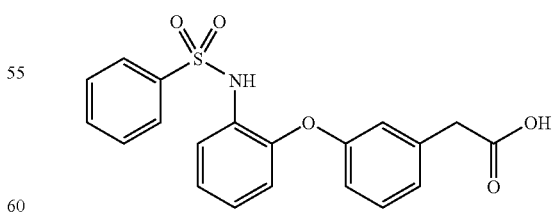

3-(2-Benzenesulfonylamino-phenoxy)phenylacetic acid (29) was prepared following the procedure described for 27 above. $^1$H-NMR (DMSO-$d_6$): δ 12.38 (br s, 1H), 9.98 (s, 1H), 7.71 (d, J=7.2 Hz, 2H), 7.59 (m, 1H), 7.48 (m, 2H), 7.37 (dd, $J_1$=7.6 Hz, $J_2$=2.0 Hz, 1H), 7.23 (t, J=8.0 Hz, 1H), 7.07-6.99

(m, 3H), 6.67 (dd, $J_1$=8.0 Hz, $J_2$=1.6 Hz, 1H), 6.57 (s, 1H), 6.55 (s, 2H), 6.48 (m, 1H), 3.52 (s, 2H). MS (ESI−): 382.1 (M−H).

Example 30

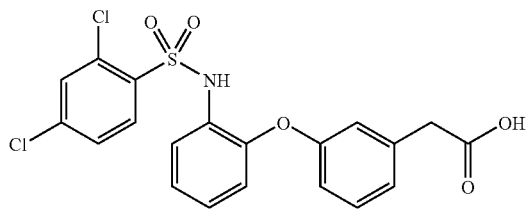

3-[2-(2,4-Dichlorobenzenesulfonyl)amino-phenoxy]phenylacetic acid (30) was prepared following the procedure described for 27 above. $^1$H-NMR (DMSO-$d_6$): δ 12.4 (br s, 1H), 10.19 (s, 1H), 7.77 (d, J=12 Hz, 1H), 7.54 (s, 1H), 7.44 (dd, $J_1$=7 Hz, $J_2$=3 Hz, 1H), 7.37 (d, J=8 Hz, 1H), 7.19 (m, 2H), 7.11 (m, 1H), 6.98 (d, J=8 Hz, 1H), 6.76 (d, J=8 Hz, 1H), 6.75 (s, 1H), 6.44 (m, 1H), 3.52 (s, 2H). MS (ESI−): 450.0 (M−H).

Example 31

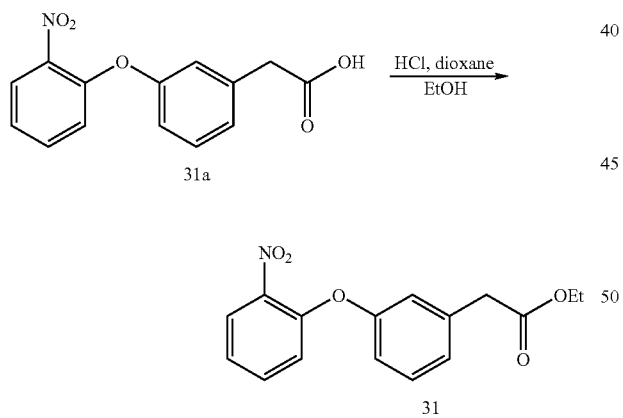

Ethyl 3-(2-nitrophenoxy)phenylacetate (31) To a solution of 31a (1.2 g, 4.39 mmol, 1.0 equiv.) in 30 mL of EtOH, was added 3.0 mL of a 4.0 M solution of HCl in dioxane. The mixture was stirred at room temperature for 48 h, and poured into 60 mL of ether. The organic layer was washed once with 30 mL of water, once with 25 mL of saturated NaHCO$_3$, and once with 25 mL of brine, dried over Na$_2$SO$_4$, and evaporated in vacuo to give 1.15 g of 31 as a light yellow liquid. $^1$H-NMR (DMSO-$d_6$): δ 8.07 (d, $J_1$=8.0 Hz, $J_2$=1.2 Hz, 1H), 7.71 (t, J=7.2 Hz, 1H), 7.38 (t, J=8.0 Hz, 2H), 7.13 (m, 2H), 6.98 (m, 2H), 4.07 (q, J=7.2 Hz, 2H), 3.69 (s, 2H), 1.17 (t, J=7.2 Hz, 3H). MS (ESI$^+$): 302.2 (M+H).

Example 32

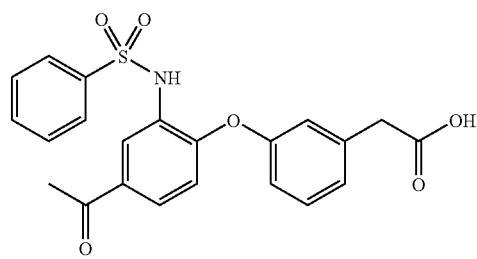

3-(4-Acetyl-2-benzenesulfonylamino-phenoxy)phenylacetic acid (32) was prepared following the procedure described for 27 above. $^1$H-NMR (DMSO-$d_6$): δ 12.40 (br s, 1H), 10.43 (s, 1H), 7.90 (s, 1H), 7.79 (m, 2H), 7.64 (s, 1H), 7.46 (d, J=8 Hz, 1H), 7.27 (t, J=8 Hz, 1H), 7.08 (m, 3H), 6.75 (d, J=8 Hz, 1H), 6.61 (s, 1H), 6.55 (d, J=8 Hz, 1H), 3.55 (s, 2H). MS (ESI−): 424.1 (M−H).

Example 33

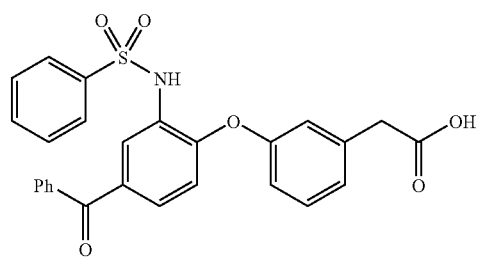

3-(4-Benzoyl-2-benzenesulfonylamino-phenoxy)phenylacetic acid (33) was prepared following the procedure described for 27 above. $^1$H-NMR (DMSO-$d_6$): δ 12.41 (br s, 1H), 10.27 (s, 1H), 7.76-7.49 (m, 12H), 7.32 (t, J=8 Hz, 1H), 7.10 (d, J=8 Hz, 1H), 6.73 (d, J=8 Hz, 1H), 6.63 (m, 2H), 3.57 (s, 2H). MS (ESI−): 486.0 (M−H).

Example 34

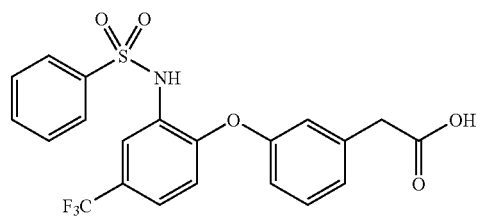

3-(4-Trifluoromethyl-2-benzenesulfonylamino-phenoxy) phenylacetic acid (34) was prepared following the procedure described for 27 above. $^1$H-NMR (DMSO-$d_6$): δ 12.41 (br s, 1H), 10.42 (s, 1H), 7.73 (m, 2H), 7.62 (m, 2H), 7.52 (t, J=7.6

Hz, 2H), 7.47 (m, 1H), 7.30 (t, J=8 Hz, 1H), 7.09 (d, J=8 Hz, 1H), 6.75 (d, J=8.8 Hz, 1H), 6.61 (m, 2H), 3.55 (s, 2H). MS (ESI+): 450.1 (M−H).

Example 35

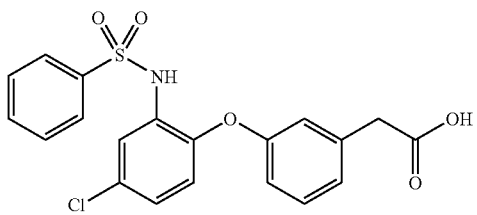

3-(4-Chloro-2-benzenesulfonylamino-phenoxy)phenylacetic acid (35) was prepared following the procedure described for 27 above. ¹H-NMR (DMSO-d$_6$): δ 12.3 (br s, 1H), 10.2 (br s, 1H), 7.72 (m, 2H), 7.60 (m, 1H), 7.50 (m, 2H), 7.37 (d, J=2.4 Hz, 1H), 7.23 (t, J=7.8 Hz, 1H), 7.14-7.01 (m, 1H), 7.01 (d, J=7.6 Hz, 1H), 6.68 (d, J=7.2 Hz, 1H), 6.57 (m, 1H), 6.52 (m, 1H), 3.52 (s, 2H). MS (ESI−): 416.0 (M−H).

Example 36

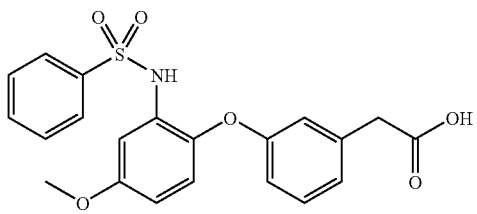

3-(4-Methoxy-2-benzenesulfonylamino-phenoxy)phenylacetic acid (36) was prepared following the procedure described for 27 above. ¹H-NMR (DMSO-d$_6$): δ 12.3 (br s, 1H), 9.33 (s, 1H), 7.71 (d, J=8 Hz, 1H), 7.47 (t, J=8 Hz, 1H), 7.08 (t, J=8 Hz, 1H), 6.90 (m, 2H), 6.75-6.34 (m, 7H), 3.67 (s, 3H), 3.44 (s, 2H). MS (ESI−): 412.0 (M−H).

Example 37

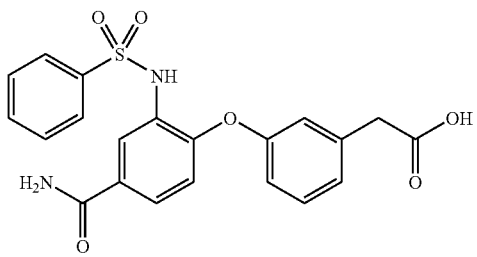

3-(4-Carbamoyl-2-benzenesulfonylamino-phenoxy)phenylacetic acid (37) was prepared following the procedure described for 27 above. ¹H-NMR (DMSO-d$_6$): δ 12.39 (br s, 1H), 10.08 (s, 1H), 7.94 (m, 2H), 7.70 (d, J=4 Hz, 2H), 7.61 (m, 2H), 7.48 (t, J=8 Hz, 2H), 7.32 (s, 1H), 7.26 (t, J=8 Hz, 1H), 7.05 (d, J=8 Hz, 1H), 6.60 (d, J=8 Hz, 1H), 6.52 (m, 2H), 3.53 (s, 2H). MS (ESI−): 425.0 (M−H).

Example 38

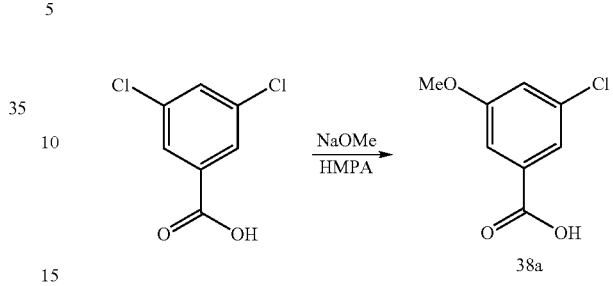

3-Chloro-5-methoxybenzoic acid (38a). To a solution of 3,5-dichlorobenzoic acid (1.91 g, 10 mmol, 1.0 equiv.) in 10 mL of HMPA was added NaOMe (1.62 g, 30 mmol, 3.0 equiv.). The mixture was heated in a 170° C. oil bath for 72 h. After cooling to room temperature, the mixture was poured into 50 mL of 1 M aqueous HCl. The precipitates were collected by filtration, and washed twice with 20 mL of water. The white solid was dried under vacuum to give 1.4 g of 38a. ¹H-NMR (DMSO-d$_6$): δ 14.0 (s, 1H), 7.47 (s, 1H), 7.38 (s, 1H), 7.29 (s, 1H), 3.82 (s, 3H).

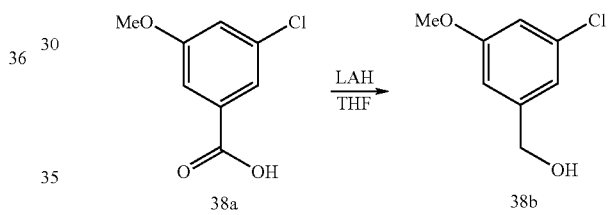

3-Chloro-5-methoxybenzyl alcohol (38b). To a solution of 38a (1.0 g, 5.36 mmol, 1.0 equiv.) in 30 mL of THF was added LAH (0.20 g, 5.36 mmol, 1.0 equiv.) in several portions. The mixture was stirred at room temperature for 2 h, and poured into 50 mL of 1M aqueous HCl. The aqueous layer was extracted twice with 30 mL of EtOAc. The combined EtOAc extracts were washed with 40 mL of saturated NaHCO$_3$, 40 mL of brine, dried over Na$_2$SO$_4$, and evaporated in vacuo to give 0.8 g of a white solid. ¹H-NMR (DMSO-d$_6$): δ 6.93 (s, 1H), 6.87 (m, 1H), 6.85 (m, 1H), 5.32 (t, J=5.8 Hz, 1H), 4.46 (d, J=6.0 Hz, 2H), 3.76 (s, 3H).

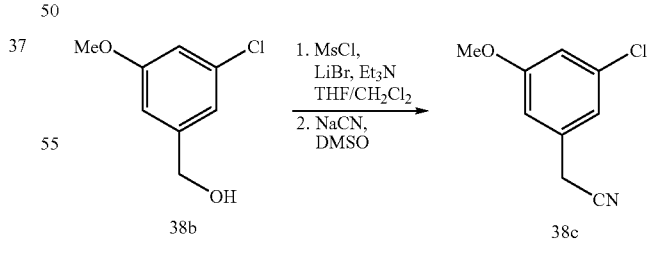

3-Chloro-5-methoxybenzylcyanide (38c). To a solution of 38b (13.3 g, 77 mmol, 1.0 equiv.) in 200 mL of dichloromethane cooled at −40° C. was added methanesulfonyl chloride (7.45 mL, 96 mmol, 1.25 equiv.), followed by dropwise addition of triethylamine (12.9 mL, 92 mmol, 1.2 equiv.). The mixture was stirred at −40° C. for 1 h. LiBr (20.0 g, 231 mmol, 3.0 equiv.) was added, followed by 400 mL of THF. The mixture was warmed to 0° C. After stirring at 0° C. for another 2 h, the mixture was poured into 200 mL of 1 M aqueous HCl. The mixture was evaporated in vacuo to remove organic solvents. The residue was extracted with 400 mL of ether. The ether layer was washed with 150 mL of saturated NaHCO$_3$, 150 mL of brine, dried over Na$_2$SO$_4$, and evaporated in vacuo to give a light tan oil, which was dissolved in 100 mL of DMSO. NaCN (4.15 g, 85 mmol, 1.1 equiv.) was added to the solution. The mixture was stirred vigorously for 14 h. The mixture was poured into 300 mL of q water. The aqueous mixture was extracted with 200 mL of ether. The ether extracts were washed with 100 mL of saturated NaHCO$_3$, 100 mL of brine, dried over Na$_2$SO$_4$, and evaporated in vacuo to give 9.8 g of a brown oil. $^1$H-NMR (DMSO-d$_6$): δ 7.00 (m, 2H), 6.90 (m, 1H), 4.02 (s, 2H), 3.78 (s, 3H).

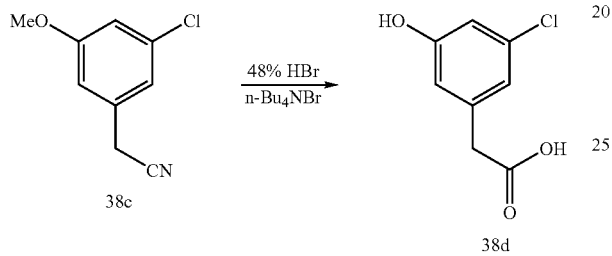

3-Chloro-5-hydroxyphenylacetic acid (38d). To a flask containing 38c (1.2 g, 6.6 mmol, 1.0 equiv.), was added 9 mL of 48% aqueous HBr, followed by tetrabutylammonium bromide (0.30 g, 0.93 mmol, 0.14 equiv.). The mixture was heated in a 125° C. oil bath for 36 h. The mixture was cooled to room temperature, and poured into 80 mL of water. The aqueous mixture was extracted three times with 40 mL of EtOAc. The combined EtOAc extracts were washed with 50 mL of brine, dried over Na$_2$SO$_4$, and evaporated in vacuo to give a dark brown solid, which was purified by silica gel chromatography to give 1.0 g of 38d as a white solid. $^1$H-NMR (DMSO-d$_6$): δ 12.34 (br s, 1H), 9.87 (s, 1H), 6.74 (s, 1H), 6.68 (s, 1H), 6.63 (s, 1H), 3.40 (s, 2H).

3-Chloro-5-(4-ethylcarbamoyl-2-nitrophenoxy)-phenylacetic acid (38e) was prepared using the method described for compound 27b (Scheme 7, above). $^1$H-NMR (DMSO-d$_6$): δ 12.51 (br s, 1H), 8.76 (t, J=6.0 Hz, 1H), 8.56 (s, 1H), 8.16 (d, J=8 Hz, 1H), 7.27 (d, J=8.0 Hz, 1H), 7.25 (m, 1H), 7.17 (m, 1H), 7.05 (m, 1H), 3.64 (s, 2H), 3.29 (m, 2H), 1.13 (t, J=8 Hz, 3H). MS (ESI$^+$): 379.1 (M+H).

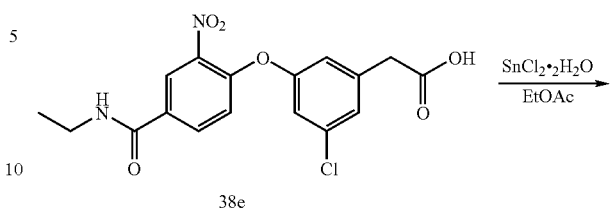

3-Chloro-5-(4-ethylcarbamoyl-2-nitrophenoxy)-phenylacetic acid (38f) To a solution of 38e (1.0 g, 2.64 mmol, 1.0 equiv.) in 20 mL of EtOAc was added SnCl$_2$.2H$_2$O (1.91 g, 8.4 mmol, 3.2 equiv.). The mixture was heated to reflux for 2 h. After cooling to room temperature, the mixture was poured into 50 mL of water. Saturated NaHCO$_3$ was added to adjust the pH value of the mixture to 3. The mixture was filtered through Celite to remove solid precipitates. The filtrate was extracted with EtOAc. The EtOAc extracts were washed with brine, dried over Na$_2$SO$_4$, and evaporated in vacuo to give 0.64 g of a light tan solid. $^1$H-NMR (DMSO-d$_6$): δ 12.45 (br s, 1H), 8.28 (t, J=6 Hz, 1H), 7.28 (s, 1H), 7.05 (s, 1H), 7.01 (d, J=4 Hz, 1H), 6.85 (d, J=8 Hz, 1H), 6.79 (m, 2H), 5.18 (br s, 2H), 3.57 (s, 2H), 3.24 (m, 2H), 1.09 (t, J=8 Hz, 3H). MS (ESI$^+$): 349.1 (M+H).

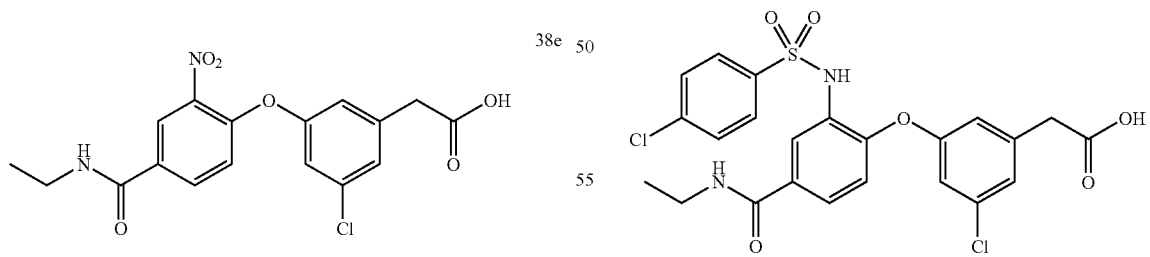

3-Chloro-5-(4-ethylcarbamoyl-2-p-chlorobenzenesulfonylamino-phenoxy)-phenylacetic acid (38) was prepared from compound 38f using the method described in Example 27. $^1$H-NMR (DMSO-d$_6$): δ 12.53 (br s, 1H), 10.27 (s, 1H), 8.51 (t, J=4 Hz, 1H), 7.95 (s, 1H), 7.65 (m, 3H), 7.48 (m, 2H), J=9 Hz, 1H), 6.62 (m, 2H), 4.08 (q, J=6.7 Hz, 1H), 3.64 (s, 2H), 2.34 (s, 3H), 1.16 (t, J=6.7 Hz, 3H). MS (ESI⁻): 468.1 (M−H).

Example 39

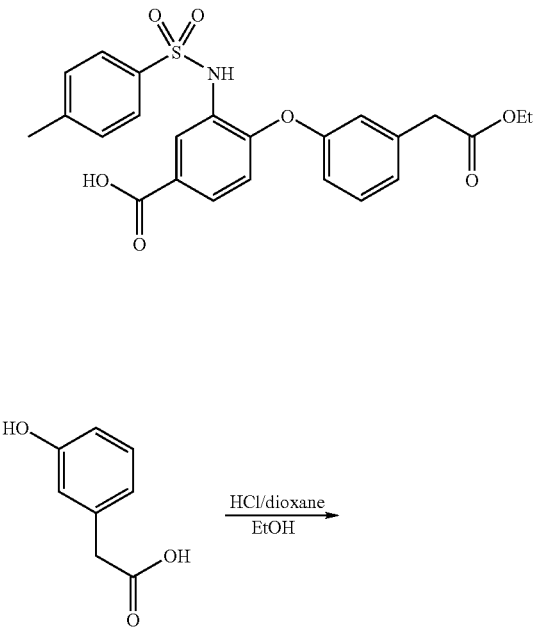

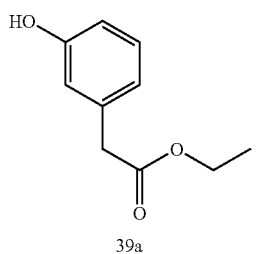

Ethyl 3-hydroxyphenylacetate (39a) was prepared using the method described for the preparation of 31. ¹H-NMR (DMSO-d$_6$): δ 9.38 (s, 1H), 7.10 (t, J=8.0 Hz, 1H), 6.65 (m, 2H), 7.13 (m, 3H), 4.07 (q, J=7.1 Hz, 2H), 3.54 (s, 2H), 1.18 (t, J=7.2 Hz, 3H).

3-(4-Carboxyl-2-p-toluenesulfonylamino-phenoxy)phenylacetic acid (39) was prepared using compound 39a following the reaction sequence described in Example 6. ¹H-NMR (DMSO-d$_6$): δ 12.9 (br s, 1H), 10.8 (s, 1H), 7.96 (s, 1H), 7.66 (m, 1H), 7.62 (m, 2H), 7.30 (m, 2H), 7.08 (m, 1H), 6.64 (d,

Example 40

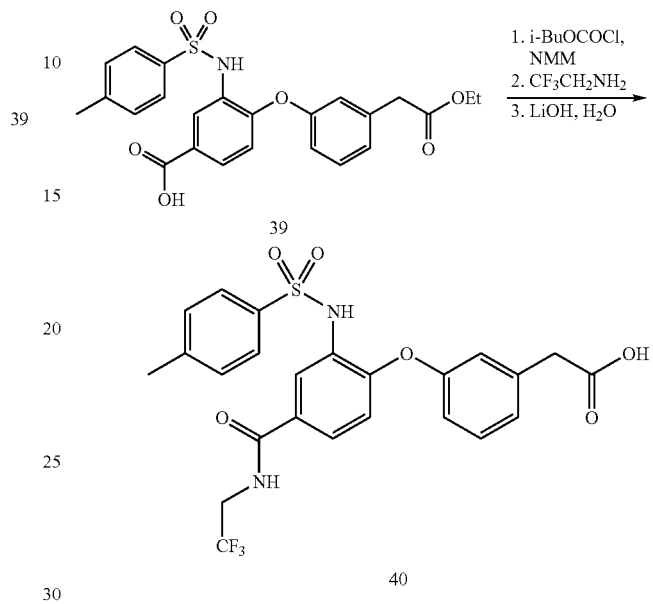

3-[4-(2,2,2-Trifluoroethyl)carbamoyl-2-p-toluenesulfonylamino-phenoxy]phenyl-acetic acid (40). To a solution of 39 (30 mg, 0.064 mmol, 1.0 equiv.) was in 0.15 mL of DMF was added isobutylchloroformate (12.4 μL, 0.096 mmol, 1.5 equiv.), and triethylamine (17.8 μL, 0.13 mmol, 2.0 equiv.). After 1 h at room temperature, trifluoroethylamine (12.5 mg, 0.13 mmol, 2.0 equiv.) was added, and the mixture was stirred for another 2 h. Water (0.1 mL) was added, followed by LiOH (27 mg, 0.64 mmol, 10 equiv.). After stirring at room temperature for 4 h, the mixture was acidified with 10% aqueous citric acid. Extractive workup with EtOAc gave a yellow residue, which was purified by reverse phase HPLC to give 3 mg of 40 as a white solid. ¹H-NMR (DMSO-d$_6$): δ 12.38 (br s, 1H), 10.06 (s, 1H), 9.07 (t, J=6.0 Hz, 1H), 7.99 (s, 1H), 7.98 (s, 1H), 7.64 (d, J=8.0 Hz, 1H), 7.57 (m, 2H), 7.26 (m, 3H), 7.06 (d, J=8.0 Hz, 1H), 6.66 (d, J=8.0 Hz, 1H), 6.49 (s, 1H), 6.49 (d, J=8.0 Hz, 1H), 4.06 (m, 2H), 3.54 (s, 2H), 2.33 (s, 3H). MS (ESI⁺): 523.1 (M+H).

Example 41

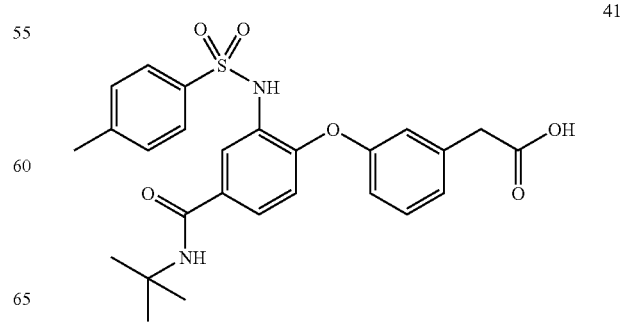

3-[4-t-Butylcarbamoyl-2-p-toluenesulfonylamino-phenoxy]phenyl-acetic acid (41) was prepared following the procedure described in Example 40. $^1$H-NMR (DMSO-d$_6$): δ 12.38 (br s, 1H), 9.97 (br s, 1H), 7.86 (m, 1H), 7.72 (s, 1H), 7.54 (m, 3H), 7.24 (m, 2H), 7.03 (m, 2H), 6.61 (d, J=8.4 Hz, 1H), 6.54 (m, 1H), 6.45 (m, 1H), 3.52 (s, 2H), 2.32 (s, 3H), 1.35 (s, 9H). MS (ESI$^+$): 497.2 (M+H).

Example 42

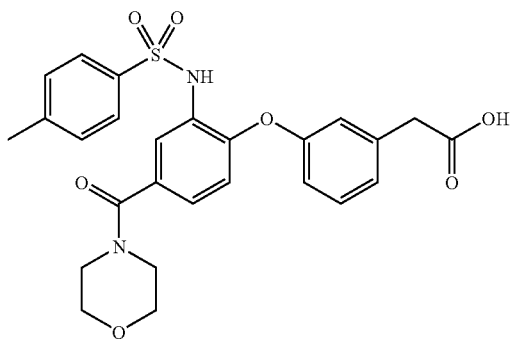

3-[4-Morphorlinocarbamoyl-2-p-toluenesulfonylaminophenoxy]phenyl-acetic acid (42) was prepared in a similar fashion as 40. $^1$H-NMR (DMSO-d$_6$): δ 12.38 (br s, 1H), 10.09 (s, 1H), 7.58 (m, 2H), 7.37 (s, 1H), 7.27 (m, 3H), 7.15 (m, 1H), 7.05 (m, 1H), 6.65 (m, 1H), 6.53 (m, 1H, 3.85-3.60 (m, 8H), 2.55 (s, 2H), 2.35 (s, 3H). MS (ESI$^+$): 511.2 (M+H).

Example 43

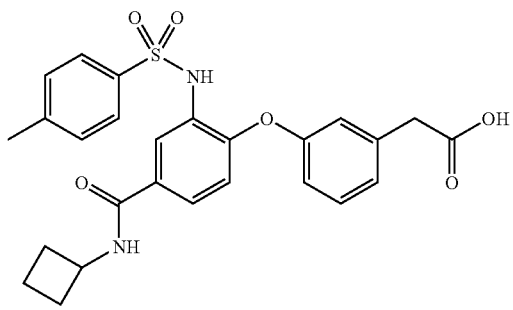

3-(4-Cyclobutylcarbamoyl-2-p-toluenesulfonylaminophenoxy)phenyl-acetic acid (43) was prepared in a similar fashion as 40. $^1$H-NMR (DMSO-d$_6$): δ 12.40 (br s, 1H), 9.99 (s, 1H), 8.59 (d, J=8 Hz, 1H), 7.93 (s, 1H), 7.58 (m, 3H), 7.24 (m, 3H), 7.04 (m, 1H), 6.63 (d, J=8 Hz, 1H), 6.54 (s, 1H), 4.38 (m, 1H), 3.53 (s, 2H), 2.32 (s, 3H), 2.19 (m, 2H), 2.04 (m, 2H), 1.68 (m, 2H). MS (ESI$^+$): 495.1 (M+H).

Example 44

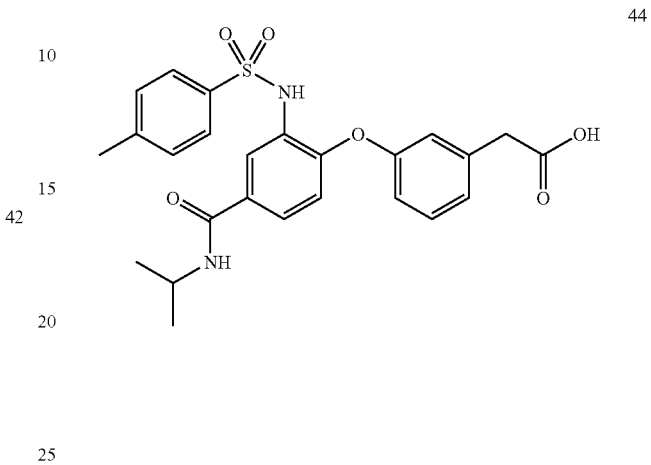

3-(4-Isopropylcarbamoyl-2-p-toluenesulfonylamino-phenoxy)phenyl-acetic acid (44) was prepared in a similar fashion as 40. $^1$H-NMR (DMSO-d$_6$): δ 12.38 (br s, 1H), 9.99 (br s, 1H), 8.19 (m, 1H), 7.93 (m, 1H), 7.60 (m, 3H), 7.27 (m, 3H), 7.04 (m, 1H), 6.65 (m, 1H), 6.47 (m, 1H), 6.45 (m, 1H), 4.05 (m, 1H), 3.52 (s, 2H), 2.32 (s, 3H), 1.16 (d, J=6.4 Hz, 1H). MS (ESI$^+$): 482.1 (M+H).

Example 45

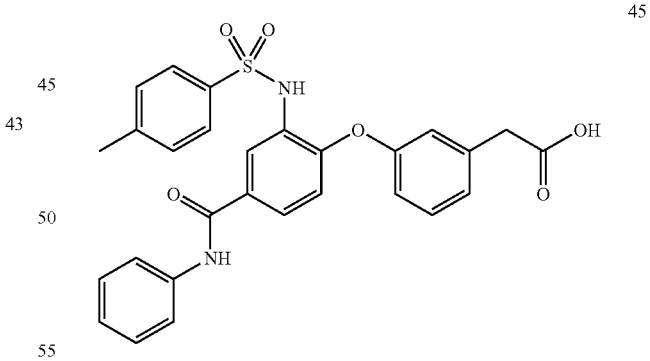

3-(4-Phenylcarbamoyl-2-p-toluenesulfonylamino-phenoxy)phenyl-acetic acid (45) was prepared in a similar fashion as 40. $^1$H-NMR (DMSO-d$_6$): δ 12.38 (br s, 1H), 10.22 (s, 1H), 8.04 (m, 1H), 7.73 (m, 3H), 7.60 (m, 2H), 7.35 (m, 3H), 7.10 (s, 1H), 6.86 (d, J=8.0 Hz, 1H), 6.61 (s, 1H), 6.35 (m, 1H), 3.58 (s, 2H), 3.29 (m, 2H), 1.11 (t, J=8.0 Hz, 3H). MS (CI$^+$): 523.1 (M+H).

7.27 (m, 3H), 7.11 (m, 2H), 6.70 (m, 1H), 6.52 (s, 1H), 6.50 (m, 1H), 3.54 (s, 2H), 2.33 (s, 3H). MS (ESI+): 517.1 (M+H).

Example 46

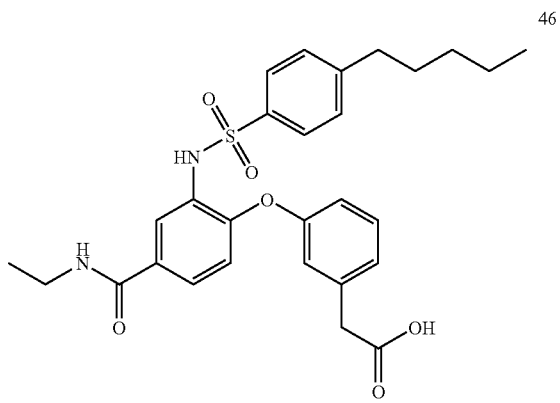

Example 46 was prepared in similar fashion as 27. $^1$H-NMR (CDCl$_3$): δ 7.98 (d, J=3.30 Hz, 1H), 7.70-7.72 (d, J=8.11 Hz, 1H), 7.64-7.66 (d, J=8.32 Hz, 1H), 7.54-7.57 (dd, J=2.10, 8.60 Hz, 1H), 7.18-7.24 (m, 2H), 7.09-7.11 (m, 1H), 6.73 (s, 1H), 6.65-6.67 (m, 1H), 6.46-6.48 (dd, J=1.96, 8.08 Hz, 1H), 6.32-6.34 (m, 1H), 3.62 (s, 2H), 3.50-3.53 (m, 2H), 2.61-2.65 (m, 2H), 1.60 (m, 2H) 1.31-1.33 (m, 2H), 1.26-1.32 (m, 5H), 0.74 (m, 3H), MS (ES+) 525.2 (M+H).

Example 47

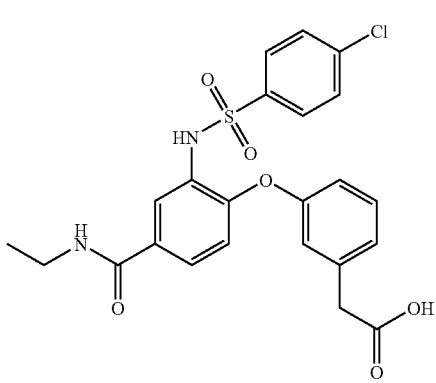

Example 47 was prepared in similar fashion as 27. $^1$H-NMR (CDCl$_3$): δ 7.59-7.67 (m, 2H), 7.57 (d, J=1.90, 1H), 7.34-7.35 (m, 1H), 7.24-7.28 (m, 1H), 7.19 (s, 1H), 7.11 (m, 1H), 6.68-6.70 (d, J=8.62 Hz, 1H), 6.59 (s, 1H), 6.51 (m, 1H), 6.29 (m, 1H), 3.63 (s, 2H), 3.49-3.55 (m, 2H), 1.21-1.27 (m, 3H). MS (ES+) 489.1 (M+H).

Example 48

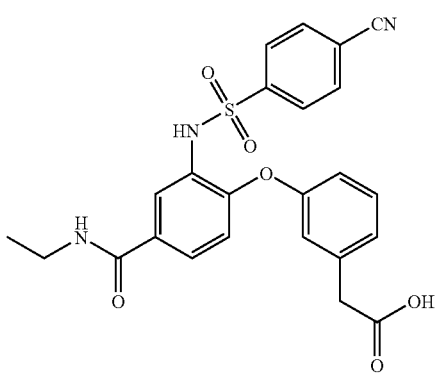

Example 48 was prepared in similar fashion as 27. $^1$H-NMR (CDCl$_3$): δ 7.86-7.88 (m, 2H) 7.70-7.72 (m, 2H), 7.59-7.61 (dd, J=2.16, 8.59 Hz, 1H), 7.25-7.28 (m, 1H), 7.12 (m, 1H), 6.73-6.76 (d, J=8.59 Hz, 1H), 6.63 (m, 1H), 6.61 (m, 1H), 6.10 (m, 1H), 3.61 (s, 2H), 3.52-3.54 (m, 2H), 1.28-1.32 (m, 3H). MS (ES+) 480.1 (M+H).

Example 49

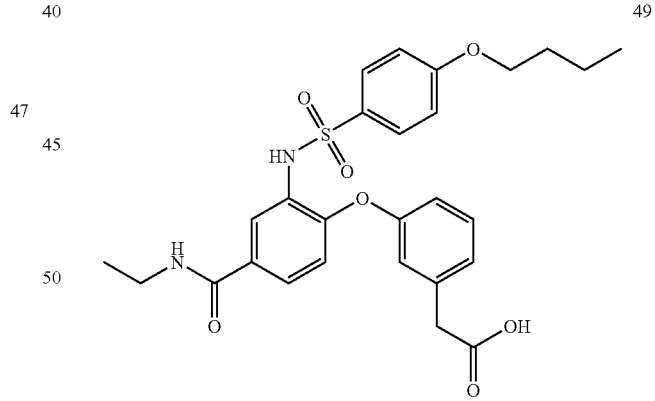

Example 49 was prepared in similar fashion as 27. $^1$H-NMR (CDCl$_3$): δ 7.86-7.88 (m, 2H), 7.70-7.72 (m, 2H), 7.59-7.61 (dd, J=2.16, 8.59, 1H), 7.16 (s, 1H), 7.02-7.04 (m, 1H), 6.83-6.84 (m, 1H), 6.65-6.67 (m, 1H), 6.58-6.59 (m, 1H), 6.38-6.41 (m, 1H), 3.59 (s, 2H), 3.49-3.52 (m, 2H), 3.47-3.49 (m, 2H), 1.76-1.79 (m, 2H), 1.46-1.49 (m, 2H), 1.28-1.32 (m, 3H), 0.95-1.00 (m, 3H), MS (ES+) 527.1 (M+H).

Example 50

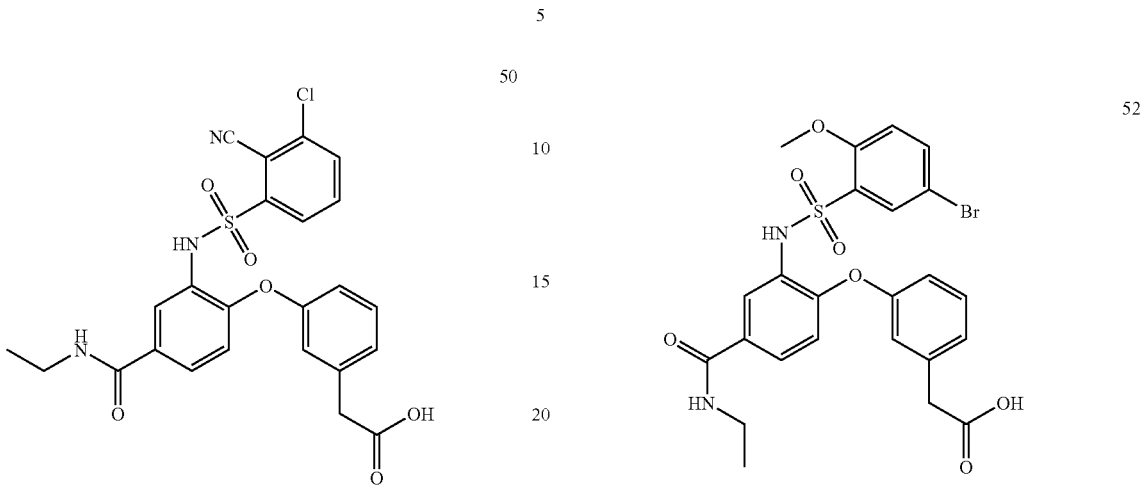

Example 50 was prepared in similar fashion as 27. $^1$H-NMR (CDCl$_3$): δ 7.59-7.91 (m, 2H), 7.51-7.58 (dd, J=1.98, 8.58 Hz, 1H), 7.47-7.51 (m, 1H), 7.33-7.34 (m, 1H), 7.06-7.08 (m, 1H), 6.85-6.87 (m, 1H), 6.73-6.76 (m, 1H), 6.54-6.56 (dd, J=2.36, 8.18 Hz, 1H), 6.14-6.16 (m, 1H), 3.63 (s, 2H), 3.49-3.56 (m, 2H), 1.24-1.28 (m, 3H). MS (ES+) 606.2 (M+H).

Example 51

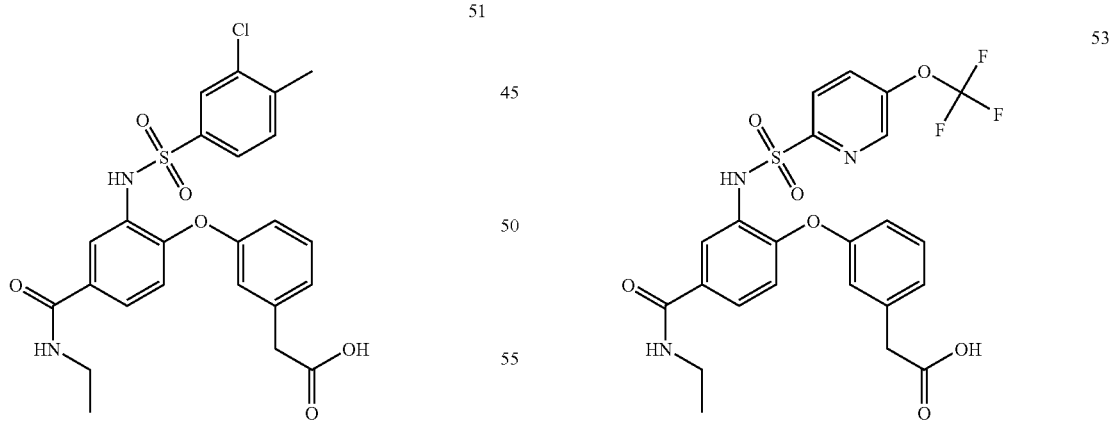

Example 51 was prepared in similar fashion as 27. $^1$H-NMR (CDCl$_3$): δ 7.76-7.77 (m, 1H), 7.55-7.60 (m, 1H), 7.52-7.57 (m, 2H), 7.05 (m, 1H), 7.02-7.04 (m, 1H), 6.72-6.74 (m, 2H), 6.55-6.60 (m, 1H), 6.10 (m, 1H), 3.65 (s, 2H), 3.52-3.54 (m, 2H), 2.42 (s, 3H), 0.89-0.91 (m, 3H). MS (ES+) 503.1 (M+H).

Example 52

Example 52 was prepared in similar fashion as 27. $^1$H-NMR (CDCl$_3$): δ 7.93-7.97 (m, 2H), 7.72 (s, 1H), 7.60-7.62 (dd, J=2.08, 8.51 Hz, 1H), 7.53-7.54 (m, 1H), 7.51-7.52 (d, J=2.53 Hz, 1H), 7.09-7.11 (m, 1H), 6.77-6.79 (m, 1H), 6.64-6.67 (m, 1H), 6.13 (m, 1H), 3.67 (s, 3H), 3.63 (s, 2H), 3.51-3.53 (m, 2H), 1.21-1.27 (m, 3H). MS (ES+) 563.1 (M+H).

Example 53

Example 53 was prepared in similar fashion as 27. $^1$H-NMR (CDCl$_3$): δ 8.27-8.29 (d, J=8.18, 1H), 8.21-8.23 (m, 2H), 7.98-8.00 (m, 1H), 7.53-7.55 (dd, J=2.16, 8.61 Hz, 1H), 7.10-7.12 (m, 1H), 6.80 (s, 1H), 6.66-6.69 (m, 2H), 6.38-6.41 (m, 1H), 3.67 (s, 2H), 3.46-3.53 (m, 2H), 1.21-1.29 (m, 3H). MS (ES+) 670.0 (M+H).

Example 54

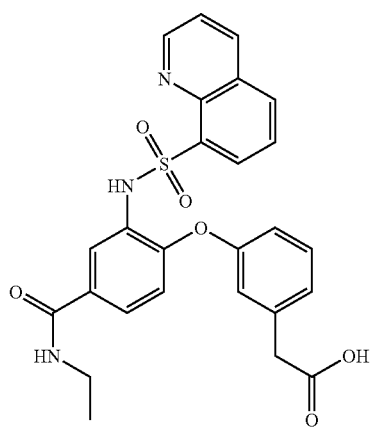

Example 54 was prepared in similar fashion as 27. $^1$H-NMR (CDCl$_3$): δ 8.33-8.35 (m, 1H), 8.08-8.09 (m, 1H), 8.04-8.06 (m, 1H), 7.94-7.96 (m, 1H), 7.89 (s, 1H), 7.56-7.58 (m, 1H), 7.49-7.54 (m, 1H), 6.99-7.02 (m, 1H), 6.94-6.98 (m, 1H), 6.61-6.64 (d, J=8.66 Hz, 1H), 6.61 (m, 1H), 6.16-6.18 (m, 1H), 6.12 (m, 1H), 3.63 (s, 2H), 3.49-3.57 (m, 2H), 1.28-1.31 (m, 3H). MS (ES+) 506.1 (M+H).

Example 55

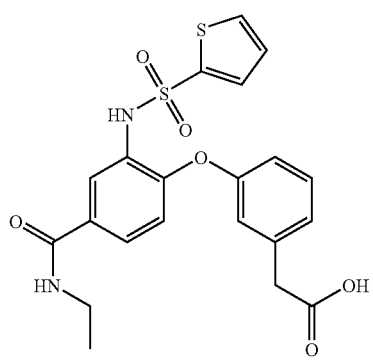

Example 55 was prepared in similar fashion as 27. $^1$H-NMR (CDCl$_3$): δ 7.62-7.64 (m, 1H), 7.57-7.58 (d, J=4.82 Hz, 1H), 7.51-7.52 (m, 1H), 7.19 (s, 1H), 7.12-7.14 (m, 1H), 7.02-7.04 (m, 1H), 6.74-6.76 (d, J=8.56 Hz, 1H), 6.69 (m, 1H), 6.67-6.68 (m, 1H), 6.15-6.17 (m, 1H), 3.64 (s, 2H), 3.52-3.55 (m, 2H), 1.21-1.27 (m, 3H). MS (ES+) 461.1 (M+H).

Example 56

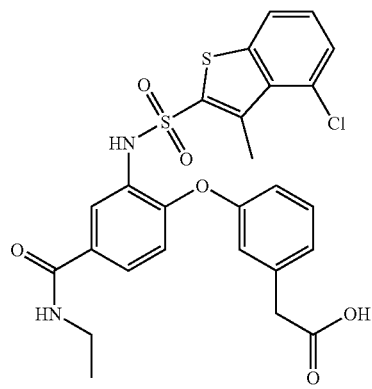

Example 56 was prepared in similar fashion as 27. $^1$H-NMR (CDCl$_3$): δ 7.60-7.70 (m, 1H), 7.53-7.55 (m, 2H), 7.30-7.33 (m, 2H), 7.24-7.28 (m, 1H), 7.19 (m, 1H), 7.11 (m, 1H), 6.68-6.70 (d, J=8.58 Hz, 1H), 6.51 (m, 1H), 3.63 (s, 2H), 3.46-3.51 (m, 2H), 2.43 (s, 3H), 1.21-1.27 (m, 3H). MS (ES+) 560.1 (M+H).

Example 57

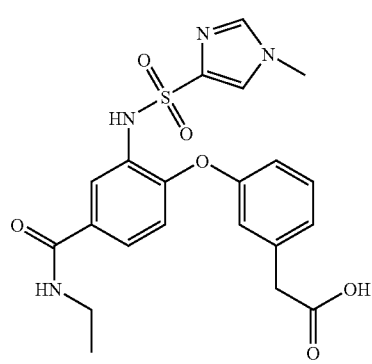

Example 57 was prepared in similar fashion as 27. $^1$H-NMR (CDCl$_3$): δ 7.53-7.54 (m, 2H), 7.32-7.33 (m, 1H), 7.10-7.11 (m, 2H), 7.02 (m, 1H), 7.00-7.01 (m, 1H), 6.76-6.78 (d, J=8.60 Hz, 1H), 6.51 (m, 1H), 3.67 (s, 2H), 3.63 (s, 3H), 3.49-3.52 (m, 2H) 1.21-1.27 (m, 3H). MS (ES+) 459.1 (M+H).

Example 58

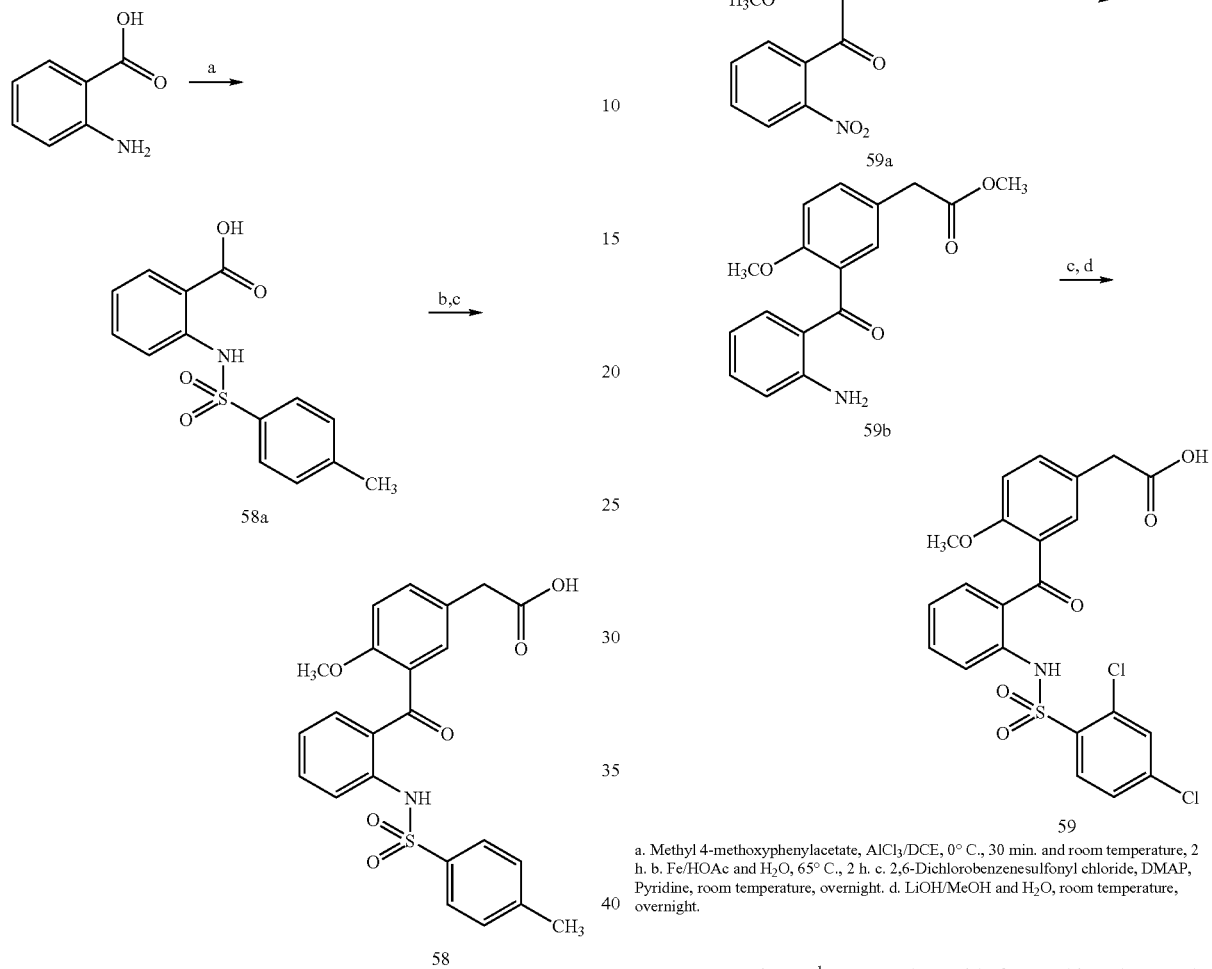

a. 4-Toluenesulfonyl chloride, Na₂CO₃/H₂O, 70° C., 1 h (Org. Synth. Coll. Vol. IV, (1963) 34:35). b. SOCl₂/DCM, room temperature, 4 days. c. 4-Methoxyphenylacetic acid, AlCl₃/DCE, 50° C., 3 h.

Example 58 was prepared according to Scheme 8. ¹H NMR (CDCl₃): δ 11.15 (s, 1H), 7.76 (m, 3H), 7.38 (m, 3H), 7.22 (d, 2H), 7.04 (s, 1H), 6.93 (m, 2H), 3.63 (s, 3H), 3.59 (s, 2H), 2.36 (s, 3H). MS (ESI⁺) 440.1 [MH]⁺.

Example 59

Scheme 9.

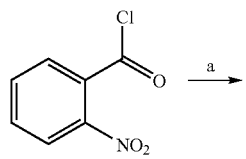

a. Methyl 4-methoxyphenylacetate, AlCl₃/DCE, 0° C., 30 min. and room temperature, 2 h. b. Fe/HOAc and H₂O, 65° C., 2 h. c. 2,6-Dichlorobenzenesulfonyl chloride, DMAP, Pyridine, room temperature, overnight. d. LiOH/MeOH and H₂O, room temperature, overnight.

Compound 59a. ¹H NMR (CDCl₃): δ 8.17 (d, 1H), 7.93 (s, 1H), 7.72 (t, 1H), 7.59 (t, 1H), 7.48 (m, 1H), 7.41 (d, 1H), 6.86 (d, 1H), 3.73 (s, 3H), 3.65 (s, 2H), 3.49 (s, 3H). MS (ESI⁺) 330.1 [MH]⁺.

Compound 59b. ¹H NMR (CDCl₃): δ 7.28 (m, 3H), 7.17 (s, 1H), 6.95 (d, 1H), 6.70 (d, 1H), 6.54 (t, 1H), 3.77 (s, 3H), 3.70 (s, 3H), 3.60 (s, 2H). MS (ESI⁺) 300.1 [MH]⁺.

Example 59 was prepared according to Scheme 9. ¹H NMR (CDCl₃): δ 11.68 (s, 1H), 8.15 (d, 1H), 7.62 (d, 1H), 7.47 (s, 1H), 7.38 (m, 4H), 7.20 (s, 1H), 6.97 (d, 2H), 3.67 (s, 3H), 3.64 (s, 2H). MS (ESI⁺) 494.0 [MH]⁺.

Example 60

Scheme 10.

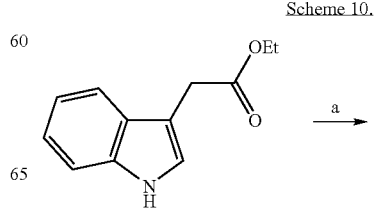

77

-continued

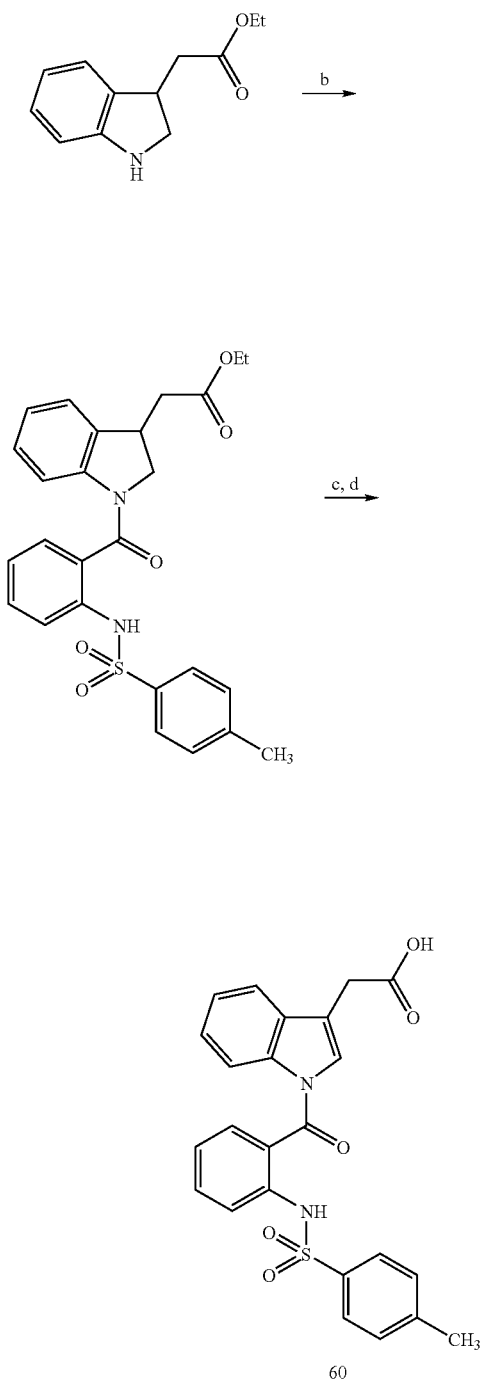

a. NaBH₃CN/HOAc, room temperature 10 min. (J. Med. Chem. (1997) 40:4222). b. compound 58a (see Scheme 8, above), EDC, HOBt, NMM, room temperature, overnight. c. LiOH/MeOH and water, room temperature, overnight. d. DDQ/toluene, 110° C., 6 h.

Example 60 was prepared according to Scheme 10. $^1$H NMR (CDCl₃): δ 8.65 (s, 1H), 8.18 (d, 1H), 7.87 (d, 1H), 7.60 (m, 4H), 7.44 (m, 3H), 7.30 (m, 1H), 6.93 (m, 3H), 3.78 (s, 2H), 2.10 (s, 3H). MS (ESI⁺) 449.1 [MH]⁺.

78

Example 61

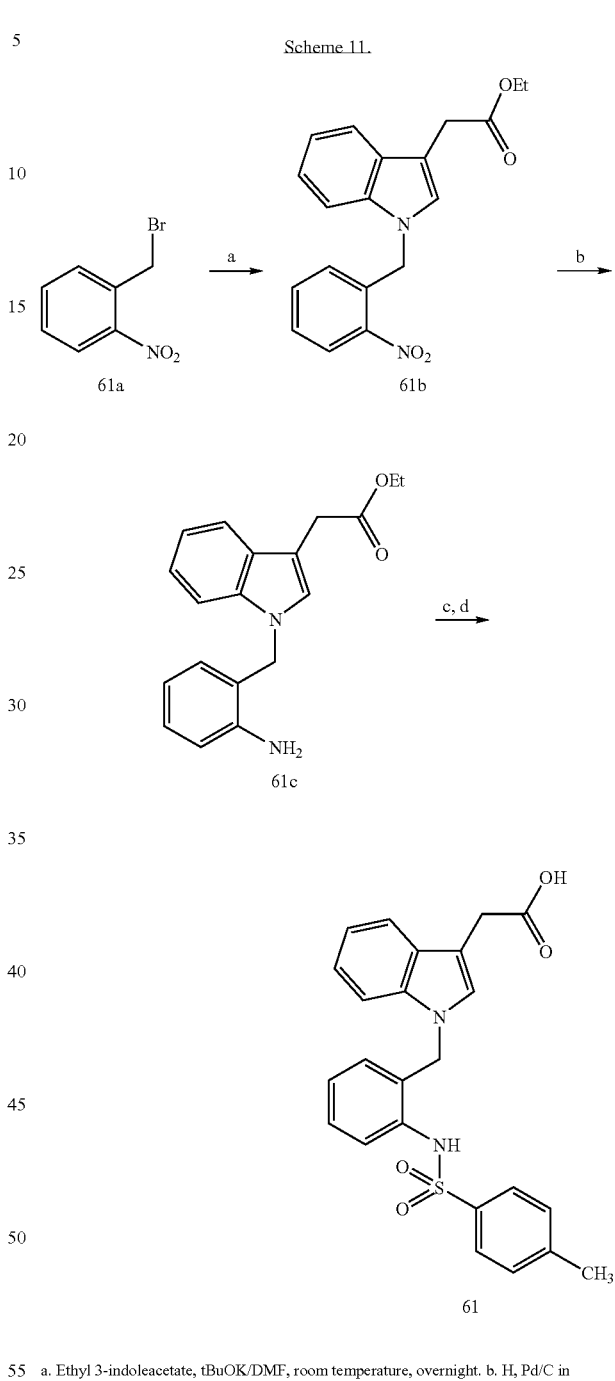

a. Ethyl 3-indoleacetate, tBuOK/DMF, room temperature, overnight. b. H, Pd/C in ethanol, room temperature, 3 h. c. 4-Toluenesulfonyl chloride, DMAP/pyridine. d. LiOH/THF, MeOH and water, room temperature, overnight.

Compound 61b. $^1$H NMR (CDCl₃): δ 8.20 (m, 1H), 7.70 (m, 1H), 7.43 (m; 2H), 7.20 (m, 4H), 6.54 (m, 1H), 5.76 (s, 2H), 4.20 (m, 2H), 3.83 (s, 2H), 1.30 (t, 3H). MS (ESI⁺) 339.1 [MH]⁺.

Example 61 was prepared according to Scheme 11. $^1$H NMR (CDCl₃): δ 7.59 (m, 2H), 7.25 (m, 1H), 7.12 (m, 6H), 6.98 (m, 1H), 6.73 (m, 1H), 6.60 (s, 1H), 5.17 (s, 2H), 3.82 (s, 2H), 2.44 (s, 3H). MS (ESI⁺) 435.1 [MH]⁺.

Example 62

Scheme 12.

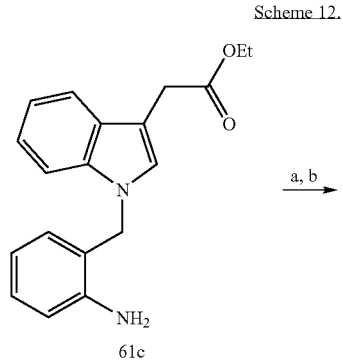

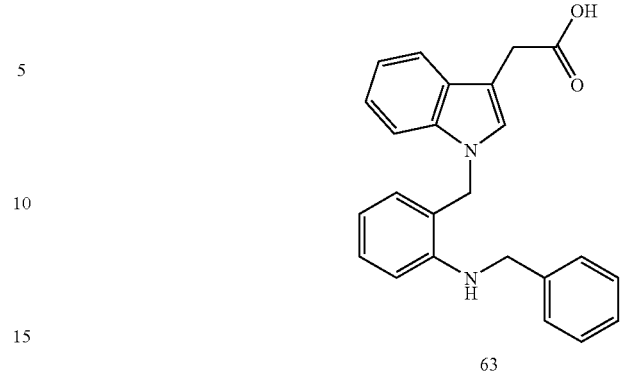

a. Phenylacetaldehyde, NaBH(OAc)₃/DCE, r.t, overnight. b. LiOH/THF, MeOH and water, room temperature, overnight.

Example 63 was prepared according to Scheme 13. $^1$H NMR (CDCl$_3$): δ 7.63 (m, 1H), 7.35 (m, 1H), 7.21 (m, 6H), 7.06 (m, 3H), 6.98 (s, 1H), 6.75 (m, 1H), 6.68 (m, 1H), 5.17 (s, 2H), 4.23 (s, 2H), 3.76 (s, 2H). MS (ESI$^+$) 371.2 [MH]$^+$.

Example 64

Scheme 14.

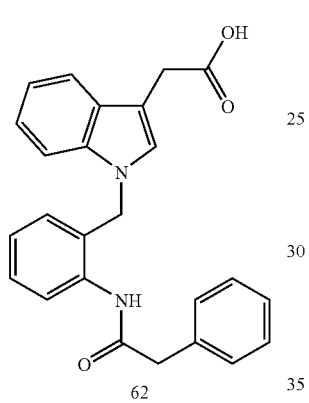

a. Phenylacetyl chloride, Net/DCM, room temperature, overnight. b. LiOH/THF, MeOH and water, room temperature, overnight.

Example 62 was prepared according to Scheme 12. $^1$H NMR (CDCl$_3$): δ 8.65 (m, 1H), 8.58 (m, 1H), 7.20 (m, 7H), 7.04 (m, 4H), 6.85 (s, 1H), 6.80 (s, 1H), 5.08 (s, 2H), 3.75 (s, 2H), 3.40 (s, 2H). MS (ESI$^+$) 399.2 [MH]$^+$.

Example 63

Scheme 13.

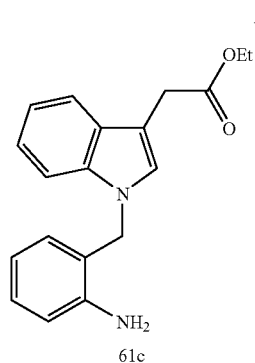

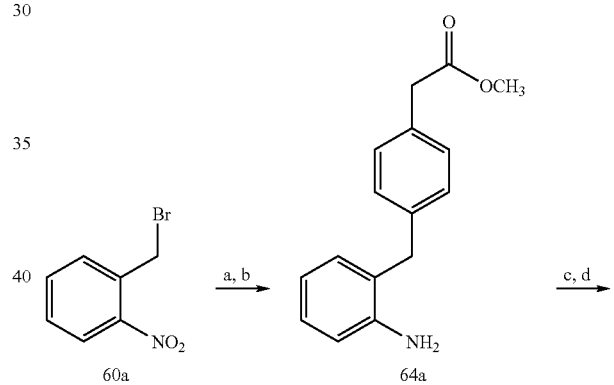

a. Methyl phenylacetate, AlCl₃, 55° C., 6 h. b. H₂, Pd/C in methanol, room temperature, 2 h. c. 4-Toluenesulfonyl chloride, DMAP/pyridine. d. LiOH/THF, MeOH and water, room temperature, overnight.

Example 64 was prepared according to Scheme 14. $^1$H NMR (CDCl$_3$): δ 7.52 (m, 2H), 7.36 (m, 1H), 7.20 (m, 7H), 6.95 (m, 1H), 6.26 (m, 1H), 3.64 (s, 2H), 3.61 (s, 2H), 2.41 (s, 3H). MS (ESI$^+$) 396.1 [MH]$^+$.

Example 65

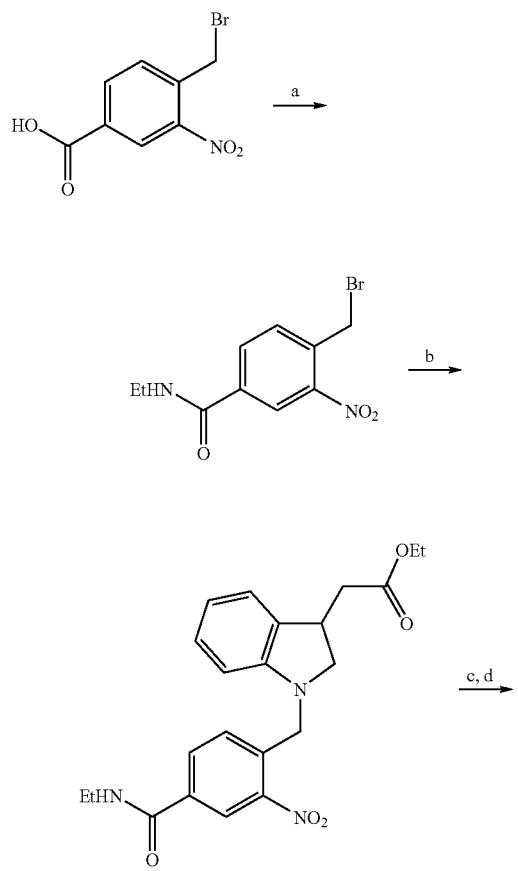

-continued

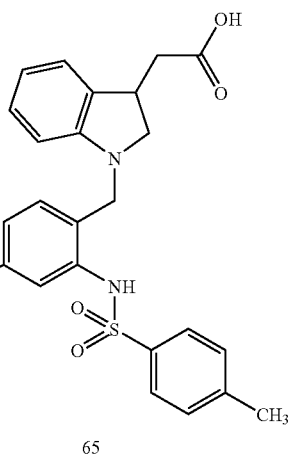

65 a. Ethylamine, EDC, HOBt, NMM in DCM, r.t, 2 h. b. Ethyl 3-dihydroindoleacetate, K$_2$CO$_3$/DMF, room temperature, overnight. c. H$_2$, Pd/C in ethanol. d. 4-Toluenesulfonyl chloride, DMAP, Pyridine, room temperature, overnight. e. LiOH/THF, MeOH, and water, room temperature, overnight.

Compound 65a. $^1$H NMR (CDCl$_3$): δ 8.95 (s, 1H), 7.87 (s, 1H), 7.61 (m, 3H), 7.24 (d, 2H), 7.20 (d, 1H), 7.15 (d, 1H), 7.10 (t, 1H), 6.89 (t, 1H), 6.34 (d, 1H), 6.14 (br s, 1H), 4.16 (m, 2H), 3.76 (dd, 2H), 3.65 (m, 1H), 3.52 (m, 2H), 3.30 (t, 1H), 2.81 (m, 2H), 2.54 (m, 1H), 2.42 (s, 3H), 1.28 (m, 6H). MS (ESI$^+$) 536.2 [MH]$^+$.

Example 65 was prepared according to Scheme 15. $^1$H NMR (CDCl$_3$): δ 8.80 (br s, 1H), 7.87 (s, 1H), 7.61 (m, 3H), 7.24 (d, 2H), 7.20 (d, 1H), 7.15 (d, 1H), 7.10 (t, 1H), 6.89 (t, 1H), 6.34 (d, 1H), 6.24 (br s, 1H), 3.78 (dd, 2H), 3.65 (m, 1H), 3.52 (m, 2H), 3.30 (t, 1H), 2.85 (m, 2H), 2.59 (m, 1H), 2.42 (s, 3H), 1.28 (m, 3H). MS (ESI$^+$) 508.2 [MH]$^+$.

Example 66

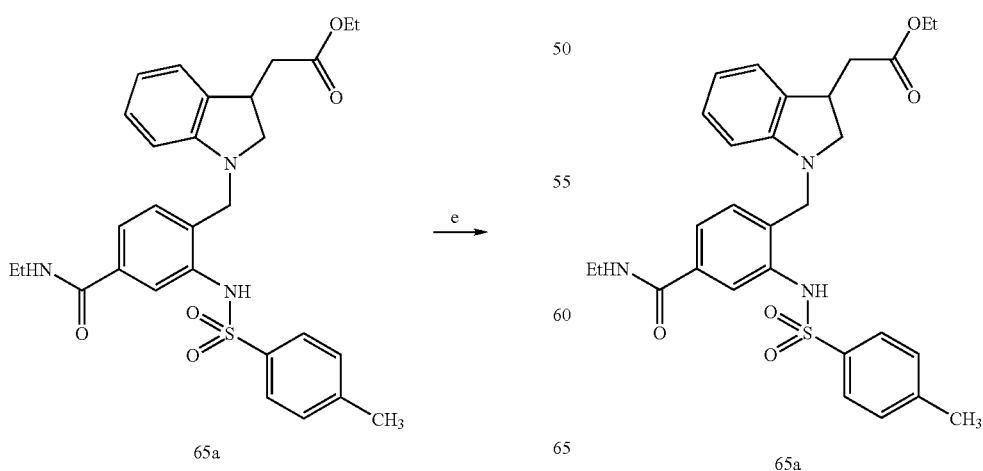

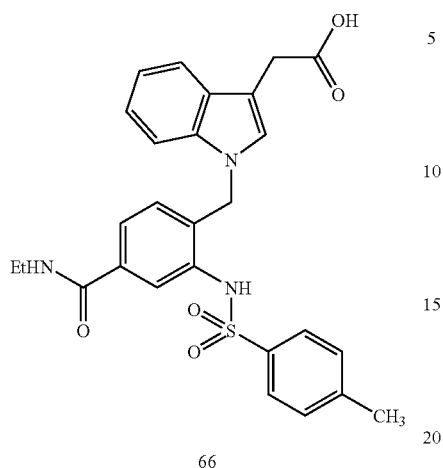

66 a. o-Chloranil in MTBE and THF, room temperature, 20 min.
b. LiOH/THF, MeOH and water, room temperature, overnight.

Example 66 was prepared according to Scheme 16. $^1$H NMR (CDCl$_3$): δ 7.56 (m, 3H), 7.39 (s, 1H), 7.36 (m, 1H), 7.21 (d, 2H), 7.07 (m, 2H), 6.84 (s, 1H), 6.78 (d, 1H), 6.55 (d, 1H), 6.16 (br s, 1H), 5.05 (s, 2H), 3.77 (s, 2H), 3.38 (m, 2H), 2.40 (s, 3H), 1.67 (t, 3H). MS (ESI$^+$) 506.2 [MH]$^+$.

Example 67

Scheme 17.

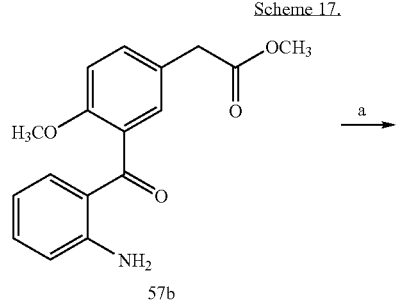

57b

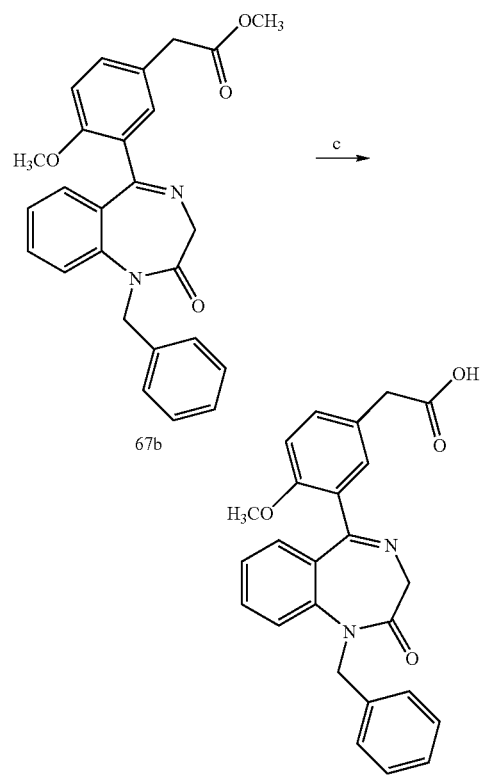

a. Glycine methyl ester HCl salt/pyridine, 110° C., 3 days. b. Benzyl bromide, tBuOK/DMF, room temperature, overnight. c. LiOH/THF, MeOH, and water, room temperature, overnight.

Compound 67a. $^1$H NMR (CDCl$_3$) δ 7.50 (m, 1H), 7.38 (m, 2H), 7.22 (d, 1H), 7.10 (m, 2H), 6.84 (d, 1H), 4.32 (s, 2H), 3.69 (s, 3H), 3.57 (s, 2H), 3.52 (s, 3H). MS (ESI$^+$) 339.1 [MH]$^+$.

Compound 67b. $^1$H NMR (CDCl$_3$) δ 7.50-7.20 (m, 9H), 7.33 (m, 2H), 7.17 (d, 1H), 7.05 (m, 2H), 6.88 (d, 1H), 5.52 (d, 1H), 5.04 (d, 1H), 4.98 (d, 1H), 3.96 (d, 1H), 3.76 (s, 3H), 3.64 (s, 2H), 3.37 (s, 3H). MS (ESI$^+$) 447.2 [MH]$^+$.

Example 67 was prepared according to Scheme 17. $^1$H NMR (CDCl$_3$ with drops of CD$_3$OD) δ 7.37 (m, 3H), 7.18 (m, 6H), 7.08 (d, 1H), 7.04 (m, 2H), 6.80 (d, 1H), 5.39 (d, 1H), 4.93 (d, 1H), 4.77 (d, 1H), 3.86 (d, 1H), 3.53 (s, 2H), 3.29 (s, 3H). MS (ESI$^+$) 433.2 [MH]$^+$.

Example 68

Scheme 18

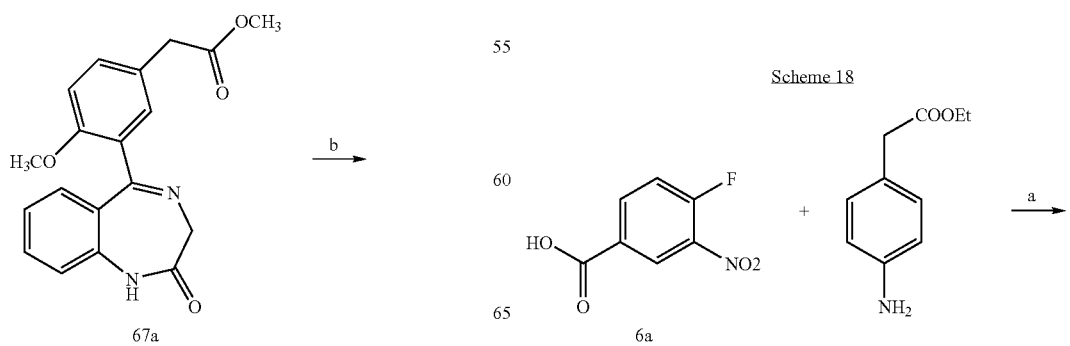

-continued

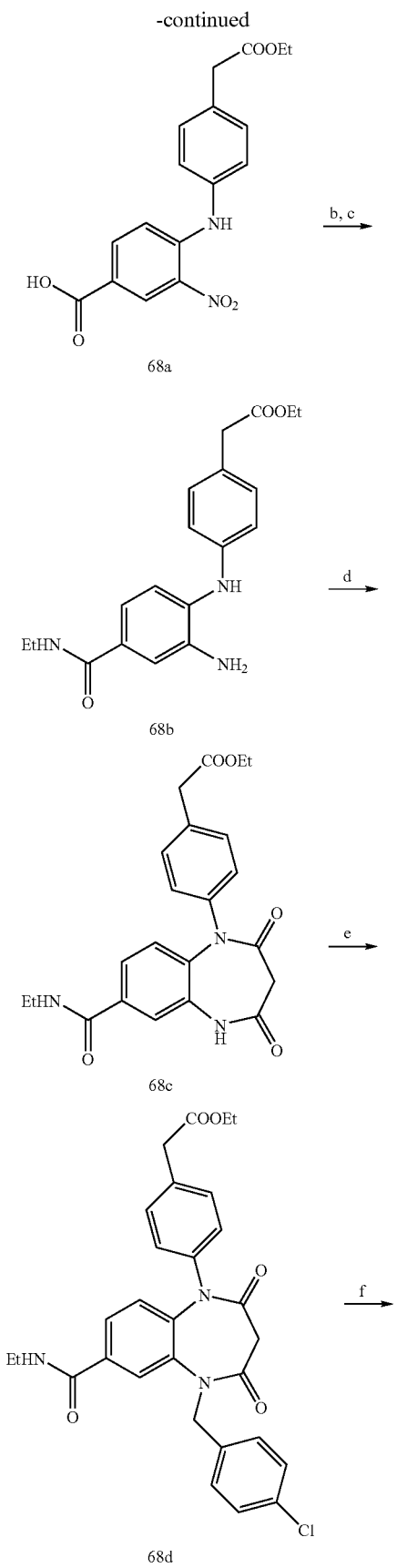

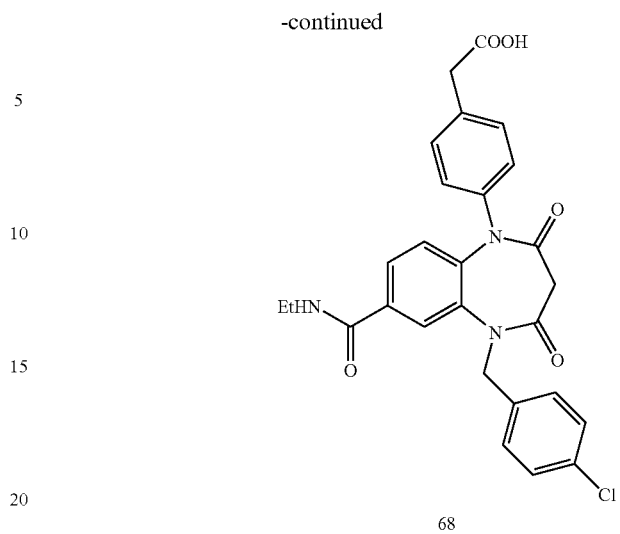

a. NEt₃/EtOH, 100° C., 5 days; b. EtNH₂, EDC, HOBt, NMM/DCM, r.t., 4 h; c. H₂, Pd/C, EtOH, r.t., 1 h; d. Malonyl dichloride/THF, r.t., 2 days; e. 4-Chlorobenzyl chloride, tBuOK/DMF, r.t., overnight; f. LiOH/THF, MeOH, and water, r.t., overnight.

Compound 68a. $^1$H NMR (CDCl$_3$) δ 9.85 (s, 1H), 9.01 (s, 1H), 8.01 (d, 2H), 7.41 (d, 2H), 7.28 (d, 2H), 7.20 (d, 1H), 4.21 (q, 2H), 3.68 (s, 2H), 1.30 (t, 3H). MS (ESI$^+$) 345.1 [MH]$^+$.

Compound 68c. $^1$H NMR (CDCl$_3$) δ 9.35 (s, 1H), 7.77 (s, 1H), 7.43 (d, 2H), 7.33 (d, 2H), 7.13 (d, 2H), 6.96 (d, 1H), 6.50 (br s, 1H), 4.15 (q, 2H), 3.62 (s, 2H), 3.53 (s, 2H), 3.48 (m, 2H), 1.25 (m, 6H). MS (ESI$^+$) 410.2 [MH]$^+$.

Compound 68d. $^1$H NMR (CDCl$_3$) δ 8.05 (s, 1H), 7.35 (m, 1H), 7.22 (m, 4H), 7.14 (d, 2H), 6.88 (d, 1H), 6.63 (d, 2H), 6.10 (br s, 1H), 5.86 (d, 1H), 4.69 (d, 1H), 4.17 (q, 2H), 3.65-3.45 (m, 4H), 2.87 (s, 1H), 2.89 (s, 1H), 1.27 (m, 6H). MS (ESI$^+$) 534.2 [MH]$^+$.

Example 68 was prepared according to Scheme 18. $^1$H NMR (CDCl$_3$ with drops of CD$_3$OD) δ 8.05 (s, 1H), 7.38 (d, 1H), 7.20 (m, 4H), 7.12 (d, 2H), 6.86 (d, 1H), 6.59 (d, 2H), 5.86 (d, 1H), 4.69 (d, 1H), 3.58 (s, 2H), 3.51 (s, 2H), 3.46 (q, 2H), 1.24 (t, 3H). MS (ESI$^+$) 506.1 [MH]$^+$.

Example 69

Scheme 19.

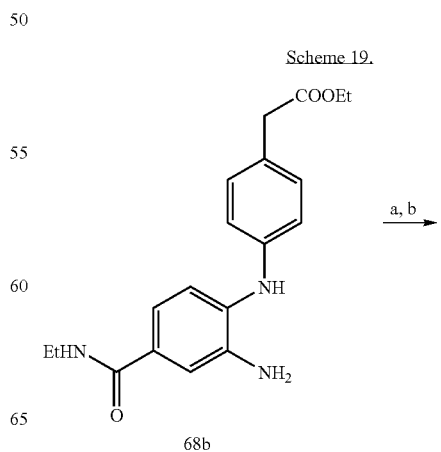

-continued

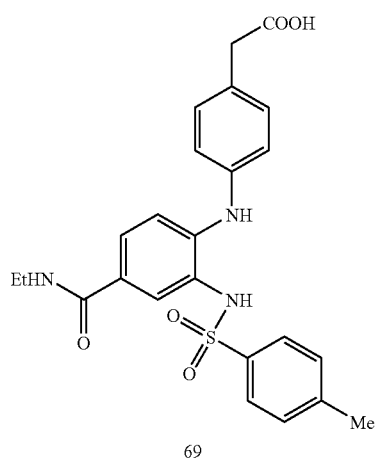

69 a. p-Toluenesulfonyl chloride, DMAP, Pyridine, r.t., overnight: b. LiOH/THF, MeOH, and water, r.t., overnight.

Example 69 was prepared according to Scheme 19. $^1$H NMR (CDCl$_3$ with drops of CD$_3$OD) δ 7.54 (d, 2H), 7.35 (m, 1H), 7.14 (m, 6H). 6.83 (d, 2H), 3.51 (s, 2H), 3.34 (q, 2H), 2.30 (s, 3H), 1.16 (t, 3H). MS (ESI$^+$) 468.2 [MH]$^+$.

Example 70

Scheme 20.

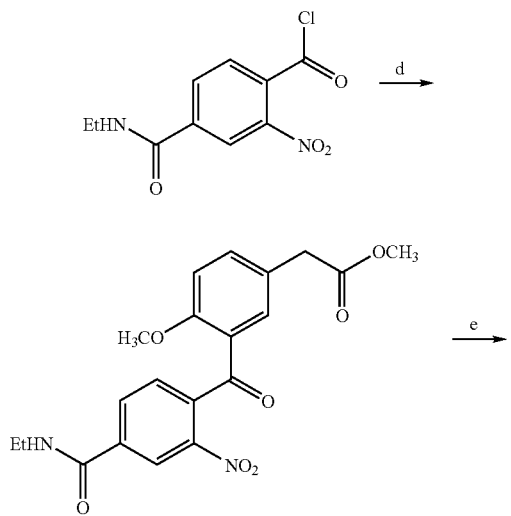

-continued

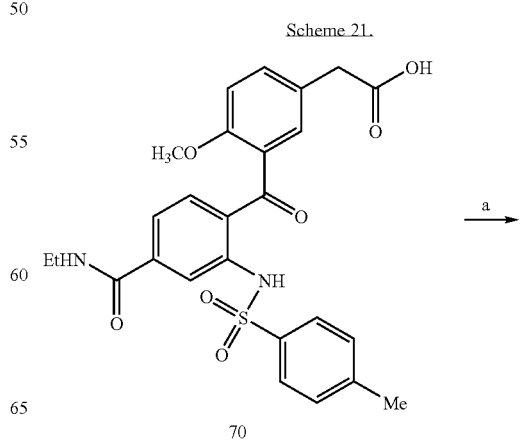

70 a. EtNH$_2$, EDC, HOBt, NMM/DCM, r.t., 4 h. b. LiOH/THF, MeOH, r.t., overnight. c. SOCl$_2$/DCM, 60° C., 8 h. d. Methyl 4-methoxyphenylacetate, AlCl$_3$/DCE, r.t., 2 h. e. Iron/HOAc, water, 65° C., 30 min. f. p-Toluenesulfonyl chloride, DMAP, pyridine, r.t., overnight. g. LiOH/THF, MeOH, water, r.t., overnight.

Example 70 was prepared according to Scheme 20. $^1$H NMR (CDCl$_3$) δ 10.96 (s, 1H), 8.00 (s, 1H), 7.74 (d, 2H), 7.40 (m, 3H), 7.22 (d, 2H), 7.07 (s, 1H), 6.91 (d, 1H), 6.18 (br s, 1H), 3.61 (s, 2H), 3.59 (s, 3H), 3.50 (m, 2H), 2.35 (s, 3H), 1.27 (t, 3H). MS (ESI$^+$) 511.2 [MH]$^+$.

Example 71

Scheme 21.

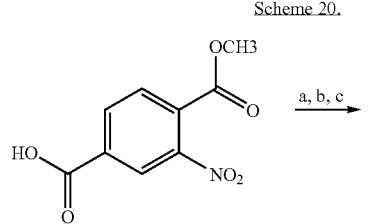

70

-continued

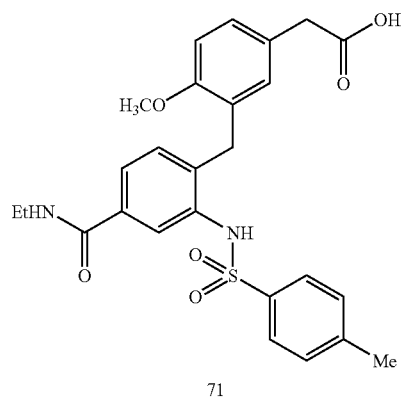

a. Triethylsilane, TFA, room temperature, overnight.

Example 71 was prepared according to Scheme 21. $^1$H NMR (CDCl$_3$) δ 8.11 (s, 1H), 7.73 (s, 1H), 7.56 (d, 1H), 7.50 (d, 2H), 7.30 (d, 1H), 7.17 (m, 3H), 7.00 (s, 1H), 6.86 (d, 1H), 6.15 (br s, 1H), 3.99 (s, 3H), 3.52 (s, 2H), 3.47 (m, 4H), 2.35 (s, 3H), 1.27 (t, 3H). MS (ESI$^+$) 497.2 [MH]$^+$.

Example 72

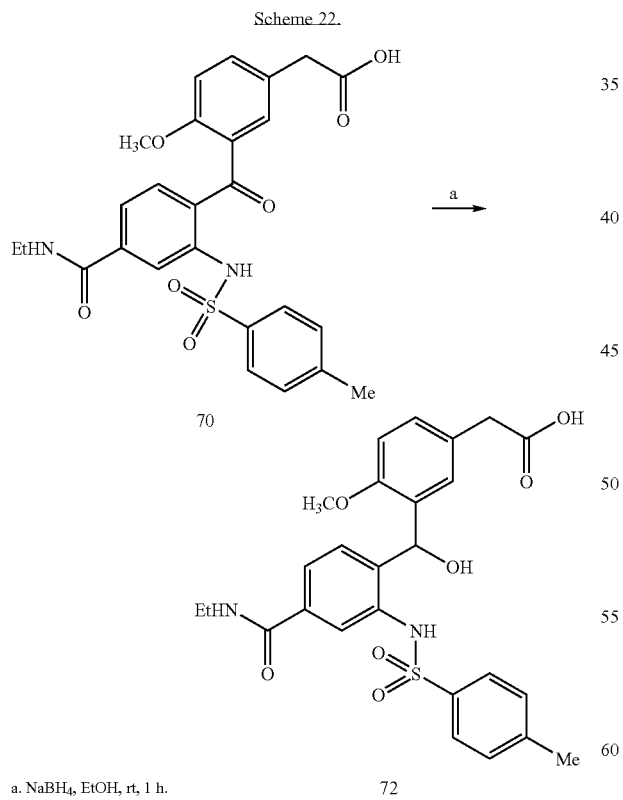

a. NaBH$_4$, EtOH, rt, 1 h.

Example 72 was prepared according to Scheme 22. $^1$H NMR (CDCl$_3$) δ 8.42 (s, 1H), 7.76 (s, 1H), 7.61 (d, 2H), 7.50 (d, 1H), 7.21 (m, 3H), 7.06 (d, 1H), 6.97 (s, 1H), 6.86 (d, 1H), 6.15 (br s, 1H), 5.58 (s, 1H), 3.82 (s, 3H), 3.53 (s, 2H), 3.47 (m, 2H), 2.39 (s, 3H), 1.24 (t, 3H). MS (ESI$^+$) 513.2 [MH]$^+$.

Example 73

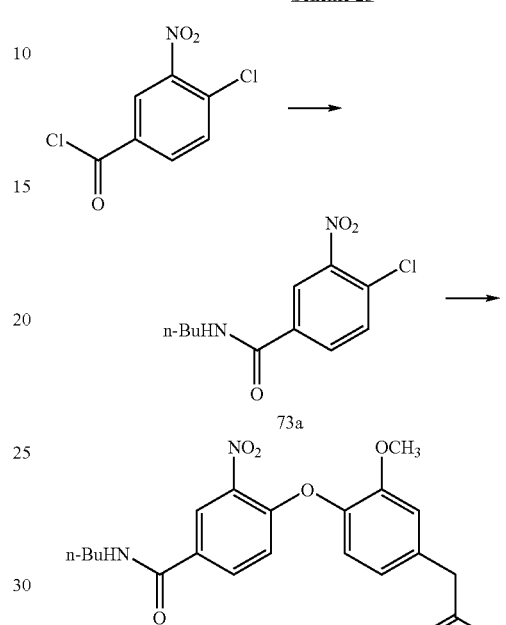

Compound 73a. To a solution of 4-chloro-3-nitrobenzoyl chloride (440 g, 2 mol), in THF (1 L) at 0° C., was added slowly a mixture of n-butylamine (198 mL, 2 mol) and triethylamine (279 mL, 2 mol) over 4 h. During addition the temperature of the reaction mixture was kept below 5° C. After addition, the mixture u % as stirred at 0° C. for 12 h. The reaction mixture was treated with EtOAc (1 L) and water (1 L). The aqueous layer was separated, and the organic layer was washed with brine (2N HCl was added to adjust pH to 2) twice and water once. The organic layer was treated with ether (2.5 L). After stirring, the solid generated was collected by filtration to give 400 g of the desired product. $^1$H NMR (DMSO-$d_6$) δ 8.78 (t, 1H), 8.50 (d, 1H), 8.15 (dd. 1H), 7.90 (d, 1H), 3.29 (q, 2H), 1.52 (m, 2H), 1.34 (m, 2H), 0.91 (t, 3H). MS (ESI$^+$) 257.0 [MH]$^+$.

Compound 73b. To a mixture of 73a (339 g, 1.32 mol) and homovanilic acid (244 g, 1.34 mol) in DMSO (1 L), was added cesium carbonate (947 g, 2.9 mol). The mixture was heated to 65° C. After 1 h of heating, 100 g more of cesium carbonate and 200 mL of DMSO were added. Two h later another 100 g of cesium carbonate and 200 mL of DMSO were added. Heating and stirring were continued for 6 h more. After cooling, EtOAc (3 L) and water (2 L) were added, and the mixture was acidified with concentrated HCl to pH2. During the acidification, the temperature was kept below 30° C. The aqueous layer was separated, and the organic layer was heated to 50° C. and washed with brine (2N HCl was added to adjust pH to 2) twice and water once. The organic layer was cooled to 0° C., and the crystal formed was collected and washed with 50% EtOAc/hexane. The mother liquor was concentrated, and the residue was recrystallized in hot EtOAc. Yield 480 g. $^1$H NMR (DMSO-$d_6$) δ 12.4 (s, 1H), 8.64 (t, 1H), 8.50 (d, 1H), 8.05 (dd, 1H), 7.19 (d, 1H), 7.16 (d, 1H), 6.96 (dd, 1H), 6.86 (d, 1H), 3.73 (s, 3H), 3.64 (s, 2H), 3.27 (q, 2H), 1.52 (m, 2H), 1.34 (m, 2H), 0.91 (t, 3H). MS (ESI$^+$) 403.1 [MH]$^+$.

Compound 73c. Pd/C (15 g, 10% wet) was added to 73b (402 g, 1 mol) in 1N NaOH (1 L, 1 mol) and water (0.2 L). The mixture was shaken under hydrogen (40 psi) for 3 h at r.t. The catalyst was removed by filtration through celite, and the celite was washed with water (1 L). The filtrate was neutralized by adding slowly 2N HCl (0.5 L) to the filtrate which was vigorously stirred. The fine powder generated was collected by filtration to give 365 g of the desired product. $^1$H NMR (DMSO-$d_6$) δ 12.4 (bs, 1H), 8.14 (t, 1H), 7.24 (d, 1H), 7.07 (d, 1H), 6.92 (dd, 1H), 6.87 (m, 2H), 6.43 (d, 1H), 5.00 (bs, 2H), 3.77 (s, 3H), 3.58 (s, 2H), 3.21 (q, 2H), 1.47 (m, 2H), 1.31 (m, 2H), 0.90 (t, 3H). MS (ESI$^+$) 373.2 [MH]$^+$.

Compound 73d. Concentrated sulfuric acid (22.4 mL) was added dropwise to a stirred solution of 73c (150 g) in methanol (800 mL) at r.t. The mixture was then heated to 60° C. for 5 h. Most of the methanol was removed under vacuum, and the residue was taken by EtOAc (800 mL) and neutralized by saturated sodium carbonate. The organic layer was separated, and the aqueous layer was extracted with EtOAc (400 mL). The combined organic layers were dried with MgSO$_4$ and concentrated to give the desired product in quantitative yield. $^1$H NMR (DMSO-$d_6$) δ 8.14 (t, 1H), 7.24 (d, 1H), 7.08 (d, 1H), 6.93 (dd, 1H), 6.86 (m, 2H), 6.45 (d, 1H), 5.05 (bs, 2H), 3.77 (s, 3H), 3.69 (s, 2H), 3.65 (s, 3H), 3.21 (q, 2H), 1.47 (m, 2H), 1.31 (m, 2H), 0.90 (t, 3H). MS (ESI$^+$) 387.2 [MH]$^+$.

Example 73. 2,4-Dichlorobenzenesulfonyl chloride (112 g, 455 mmol) was added to a mixture of 73d (135 g, 350 mmol) and 2,6-lutidine (57 mL, 490 mmol) in THF (500 mL) at r.t. The mixture was heated to 60° C. and stirred for 12 h. After cooling to r.t., water (300 mL) and 10N NaOH (180 mL) were added. The mixture was stirred at r.t. for 2 h, acidified to pH 2 with concentrated HCl, and extracted with EtOAc (1 L). The organic layer was washed with brine (2N HCl was added to adjust pH to 2) three times, dried with MgSO$_4$, and concentrated. The residue was treated with DCM (300 mL), stirred, and collected by filtration. Then the product was recrystallized in hot EtOH (95%) (400 mL) to give 120 g of the desired product. The mother liquor was concentrated, and the residue was purified using the method to give 30 g of desired product. $^1$H NMR (DMSO-14) δ 12.4 (bs, 1H), 10.2 (bs, 1H), 8.38 (t, 1H), 7.87 (d, 1H), 7.84 (d, 1H), 7.75 (d, 1H), 7.58 (dd, 1H), 7.50 (dd, 1H), 7.04 (d, 1H), 6.81 (dd, 1H), 6.55 (d, 1H), 6.40 (d, 1H), 3.62 (s, 3H), 3.59 (s, 2H), 3.23 (q, 2H), 1.49 (m, 2H), 1.31 (m, 2H), 0.91 (t, 3H). MS (ESI$^+$) 581.1 [MH]$^+$.

Example 74

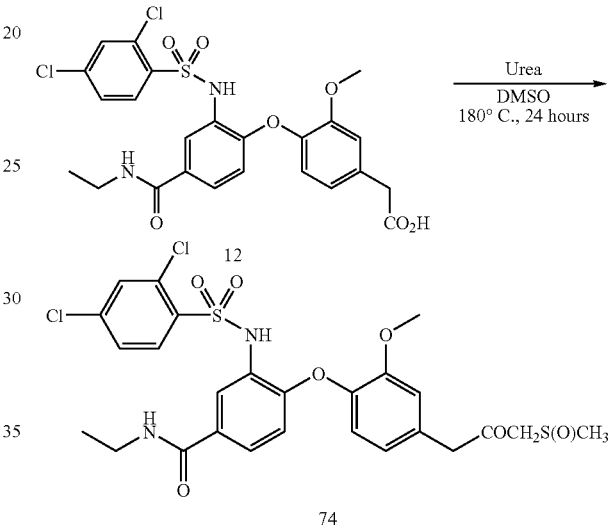

3-(2,4-Dichloro-benzenesulfonylamino)-N-ethyl-4-[4-(3-methanesulfinyl-2-oxo-propyl)-2-methoxy-phenoxy]-benzamide (74). Example 74 was prepared from Example 12 according to Scheme 24. 400 MHz $^1$H NMR (CDCl$_3$) δ: 7.95 (d, J=8.5 Hz, 1H), 7.87 (d, J=2.1 Hz, 1H), 7.81 (s, 1H), 7.44 (dd, J=8.6, 2.16 Hz, 1H), 7.40 (d, J=1.88 Hz, 1H), 7.31 (dd, J=8.44, 1.88 Hz, 1H), 6.92 (d. J=1.76 Hz, 1H), 6.71 (d, J=8.08 Hz, 1H), 6.55 (d, J=8.56 Hz, 1H), 5.18 (s, 2H), 3.68 (s, 3H), 3.67 (s, 2H), 3.46 (m, 2H), 2.22 (s, 3H), 1.24 (dd, J=7.24, 7.24 Hz, 3H). LCMS (ES−) m/z 611 (M−1).

Example 75

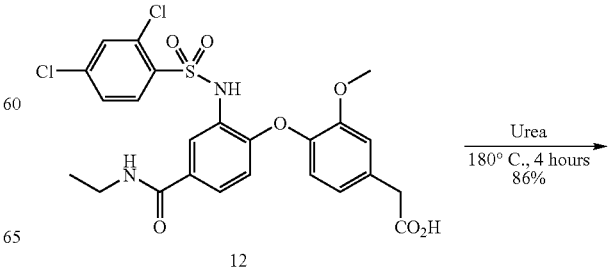

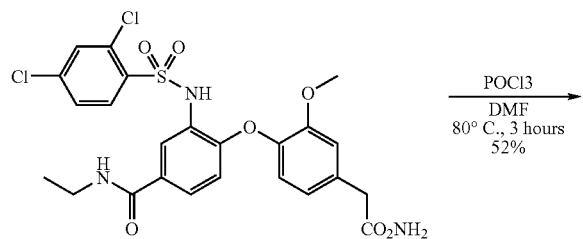

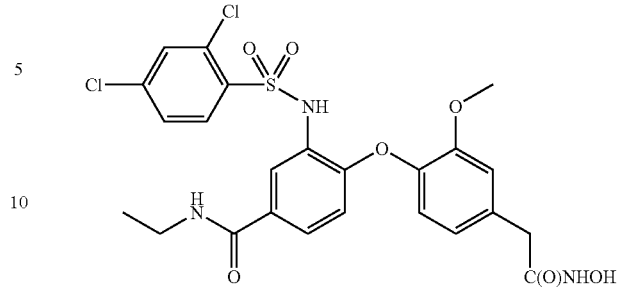

76

3-(2,4-Dichloro-benzenesulfonylamino)-N-ethyl-4-(4-hydroxy-carbamoylmethyl-2-methoxy-phenoxy)-benzamide (76) was prepared according to Scheme 26. 400 MHz $^1$H NMR (Acetone-$d_6$) δ: 10.2 (s, 1H), 8.82 (s, 1H), 8.06 (d, J=2.04 Hz, 1H), 7.97 (d, J=8.52 Hz, 1H), 7.75 (s, 1H), 7.65 (d, J=2.0 Hz, 1H), 7.58 (dd, J=8.64, 2.12 Hz, 1H), 7.53 (dd, J=8.52, 2.08 Hz, 1H), 7.12 (s, 1H), 6.89 (dd, J=8.08, 1.76 Hz, 1H), 6.75 (d, J=8.04 Hz, 1H), 6.45 (d, J=8.56 Hz, 1H), 3.68 (s, 3H), 3.45 (s, 2H), 3.40 (m, 2H), 1.14 (dd, J=7.20, 7.20 Hz, 3H). LCMS (ES−) m/z 567 (M−1).

Example 77

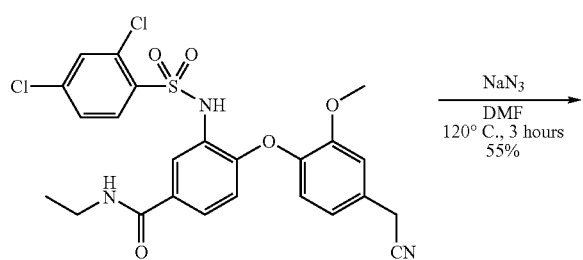

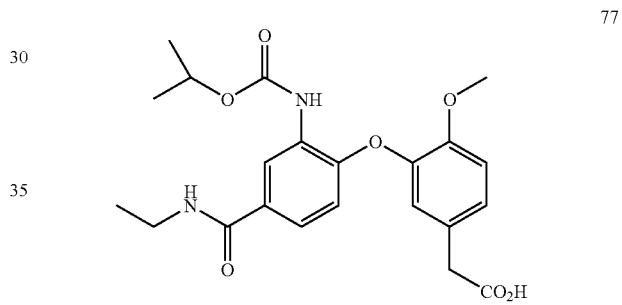

77

[3-(4-Ethylcarbamoyl-2-isopropoxycarbonylamino-phenoxy)-4-methoxy-phenyl]-acetic acid (77). 400 MHz $^1$H NMR (Acetone-$d_6$) δ: 10.9 (br s, 1H), 8.63 (d, J=2.07 Hz, 1H), 8.03 (s, 1H), 7.72 (br s, 1H), 7.46 (dd, J=8.52, 2.19 Hz, 1H), 7.20 9dd, J=8.35, 2.16 Hz, 1H), 7.15 (d, J=2.10, 1H), 7.13 (d, J=8.39 Hz, 1H), 6.69 (d, J=8.51 Hz, 1H), 5.00 (m, 1H), 3.80 (s, 3H), 3.61 (s, 2H), 3.42 (m, 2H), 1.29 (d, J=6.25 Hz, 6H), 1.19 (dd, J=7.13, 7.13 Hz, 3H). LCMS (ES−) m/z 429 (M−1).

Example 78

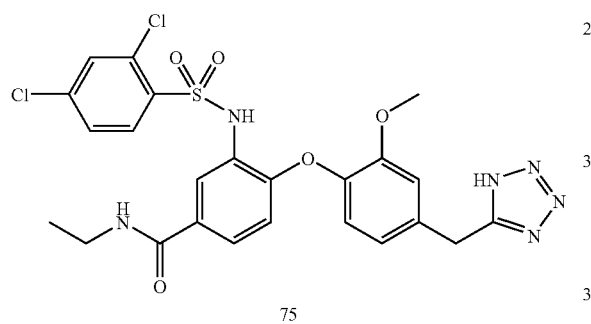

75

3-(2,4-Dichloro-benzenesulfonylamino)-N-ethyl-4-[2-methoxy-4-(1H-tetrazol-5-ylmethyl)-phenoxy]-benzamide (75) was prepared according to Scheme 25. 400 MHz $^1$H NMR (Acetone-$d_6$) δ: 8.60 (br s, 1H), 8.04 (d, J=2.12 Hz, 1H), 7.94 (d, J=8.52 Hz, 1H), 7.72 (br s, 1H), 7.61 (d, J=2.04 Hz, 1H), 7.55 (dd, J=8.60, 2.2 Hz, 1H), 7.49 (dd, J=8.48, 2.12 Hz, 1H), 7.16 (d, J=2.16 Hz, 1H), 6.90 (dd, J=8.12, 2.16 Hz, 1H), 6.78 (d, J=8.16 Hz, 1H), 6.48 (d, J=8.52 Hz, 1H), 4.38 (s, 2H), 3.67 (s, 3H), 3.38 9m, 2H), 1.16 (dd, J=7.16, 7.16 Hz, 3H). LCMS (ES+) m/z 578 (M+1).

Example 76

Scheme 26

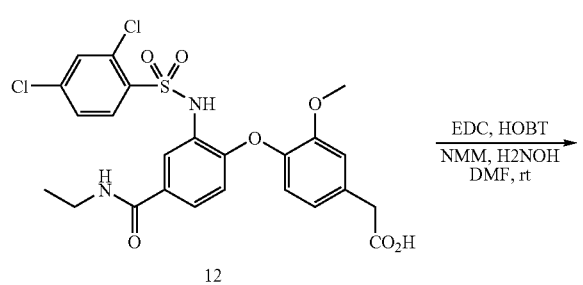

Scheme 27

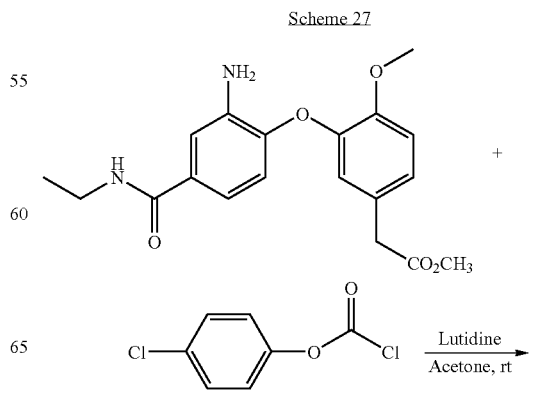

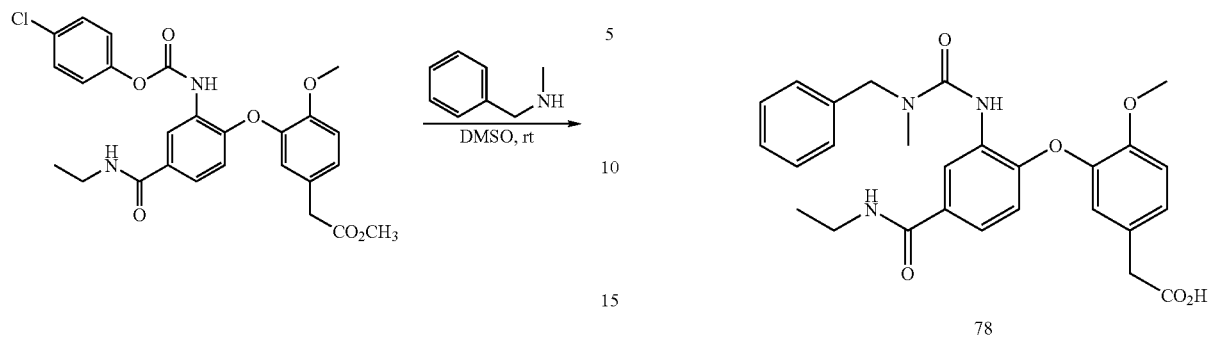
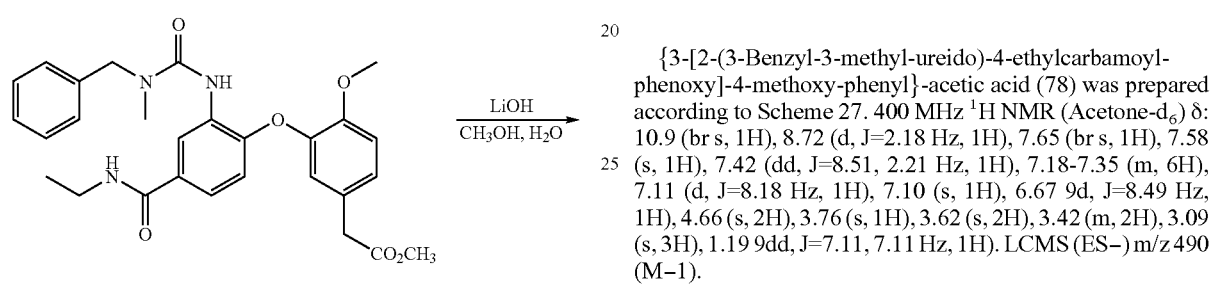
{3-[2-(3-Benzyl-3-methyl-ureido)-4-ethylcarbamoyl-phenoxy]-4-methoxy-phenyl}-acetic acid (78) was prepared according to Scheme 27. 400 MHz $^1$H NMR (Acetone-$d_6$) δ: 10.9 (br s, 1H), 8.72 (d, J=2.18 Hz, 1H), 7.65 (br s, 1H), 7.58 (s, 1H), 7.42 (dd, J=8.51, 2.21 Hz, 1H), 7.18-7.35 (m, 6H), 7.11 (d, J=8.18 Hz, 1H), 7.10 (s, 1H), 6.67 9d, J=8.49 Hz, 1H), 4.66 (s, 2H), 3.76 (s, 1H), 3.62 (s, 2H), 3.42 (m, 2H), 3.09 (s, 3H), 1.19 9dd, J=7.11, 7.11 Hz, 1H). LCMS (ES−) m/z 490 (M−1).
Example 79
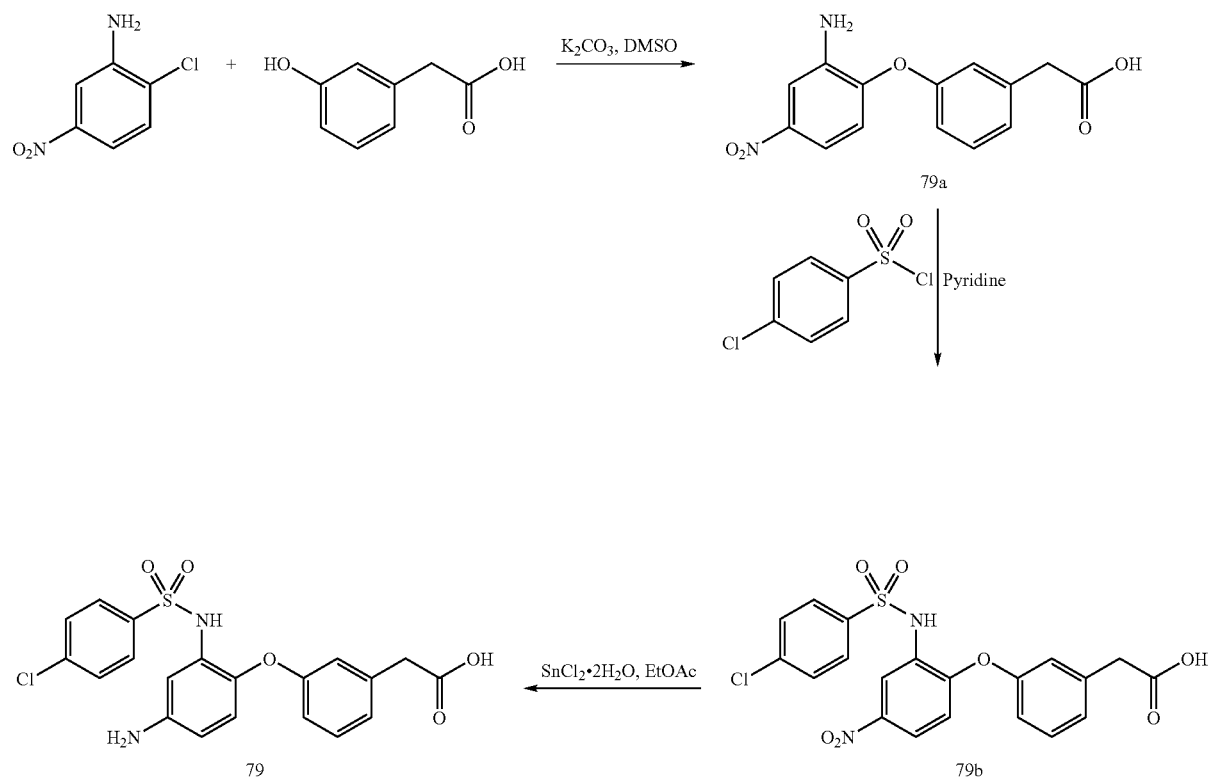

3-(2-Amino-4-nitrophenoxy)phenylacetic acid (79a) A mixture of 2-fluoro-5-nitroaniline (3.1 g, 20 mmol, 1.0 equiv.) 3-hydroxyphenylacetic acid (3.04 g, 20 mmol, 1.0 equiv.) and $K_2CO_3$ (6.9 g 50 mmol, 2.5 equiv.) in 20 mL of DMSO was heated to 130° C. and stirred at that temperature for 18 h. After cooling to room temperature, the mixture was poured into aqueous citric acid. The resulting mixture was extracted twice with EtOAc. The combined organic extract was washed with brine, dried over sodium sulfate, and evaporated in vacuo to give a dark brown foam, which was purified by silica gel chromatography to give 4.3 g of 1 as a yellow solid. MS (ESI$^+$): 289.0 (M+H).

3-[2-(4-Chlorophenylsulfonylamino)-4-nitrophenoxy] phenylacetic acid (79b) To a solution of 79a (4.3 g, 14.9 mmol, 1.0 equiv.) in 20 mL of pyridine, was added 4-chlorosulfonyl chloride (3.67 g, 17.4 mmol, 1.2 equiv.). The mixture was stirred at room temperature for 4 h. The mixture was diluted with 100 mL of EtOAc and washed twice with 100 mL of 10% aqueous citric acid, once with 50 mL of brine, dried over $Na_2SO_4$, and concentrated in vacuo to give a brown solid, which was purified by silica gel chromatography to give 6.2 g of 79b as a yellow solid. $^1$H-NMR (400 MHz, DMSO-d$_6$): δ 12.45 (br s, 1H), 10.66 (s, 1H), 8.21 (d, J=4 Hz, 1H), 7.75 (d, J=8 Hz, 2H), 7.60 (d, J=8 Hz, 2H), 7.33 (t, J=8 Hz, 1H), 7.15 (m, 1H), 6.77 (d, J=12 Hz, 1H), 6.64 (m, 3H), 3.58 (s, 2H). MS (ESI–): 461.1 (M–H).

3-[2-(4-Chlorophenylsulfonylamino)-4-aminophenoxy] phenylacetic acid (79) To a solution of 79b (5.5 g, 11.9 mmol, 1.0 equiv.) in 50 mL of EtOAc was added $SnCl_2.2H_2O$ (8.04 g, 35.6 mmol, 3.1 equiv.). The mixture was heated to reflux for 2 h. After cooling to room temperature, the mixture was poured into 50 mL of water. Saturated NaHCO$_3$ was added to adjust the pH value of the mixture to 3. The mixture was filtered through Celite to remove solid precipitates. The filtrate was extracted with EtOAc. The EtOAc extract was washed with brine, dried over $Na_2SO_4$; and evaporated in vacuo to give a light tan solid, which was purified by silica gel chromatography to give 79 as a white solid. $^1$H-NMR (400 MHz, DMSO-d$_6$): δ 12.41 (br s, 1H), 9.83 (s, 1H), 7.635 (d, J=8.4 Hz, 2H), 7.449 (d, J=8.4 Hz, 1H), 7.09 (t, J=8.0 Hz, 1H), 6.87 (d, J=7.6 Hz, 1H), 6.77 (s, 1H), 6.59 (d, J=8.4 Hz, 1H), 6.55 (s, 1H), 6.44 (m, 1H), 6.34 (dd, J=8.4, 2.4 Hz, 1H), 3.47 (s, 2H), 3.56 (s, 2H); MS (ESI$^-$): 431.1 (M+H).

Example 80

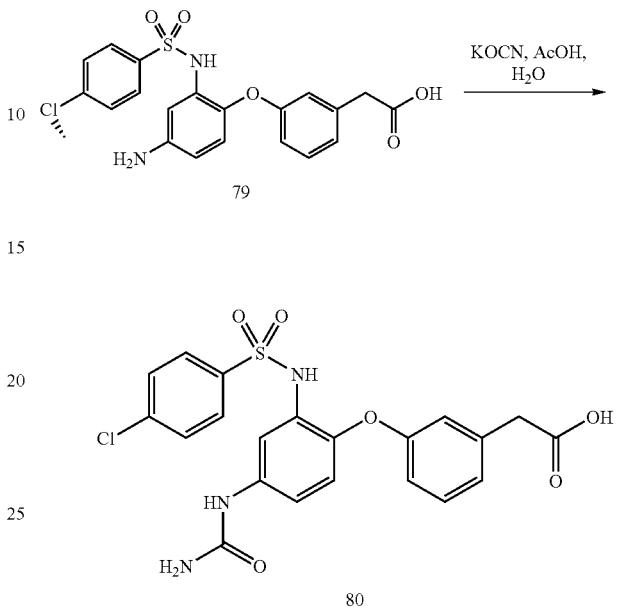

3-[2-(4-Chlorophenylsulfonylamino)-4-ureido-phenoxy] phenylacetic acid (80) To a solution of 79 (86 mg, 0.2 mmol, 1.0 equiv.) in 0.4 mL of AcOH, was added potassium cyanate (32 mg, 0.4 mmol, 2 equiv.), followed by 0.2 mL of water. The mixture was stirred at room temperature for 3 h, and evaporated in vacuo to give a yellow foam. The foam was dissolved in minimal amount of EtOAc and purified by silica gel chromatography to give 26 mg of 80 as a white solid. $^1$H-NMR (400 MHz, DMSO-d$_6$): δ 12.35 (br s, 1H), 9.98 (br s, 1H), 8.62 (s, 1H), 7.66 (d, J=8 Hz, 2H), 7.48 (m, 3H), 7.21 (d, J=8 Hz, 1H), 7.13 (t, J=8 Hz, 1H), 6.91 (d, J=8.0 Hz, 1H), 6.69 (d, J=8 Hz, 1H), 6.56 (s, 1H), 6.38 (d, J=8 Hz, 1H), 5.82 (s, 2H), 3.49 (s, 2H); MS (ESI$^+$): 476.0 (M+H).

Example 81

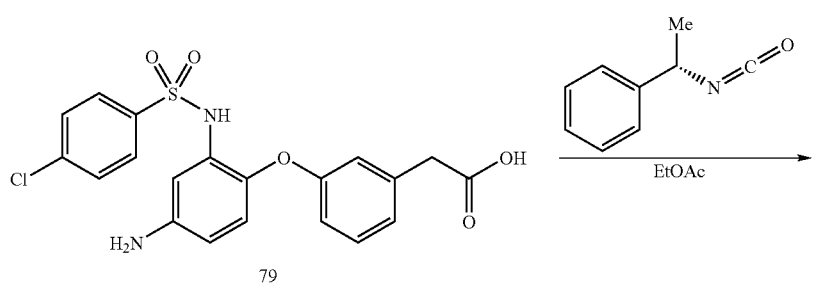

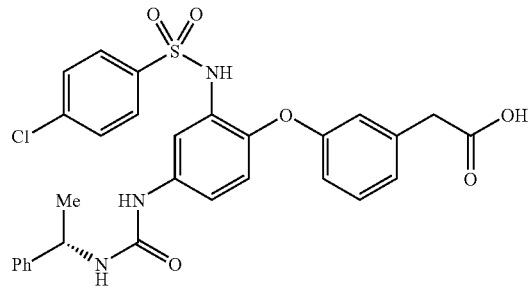

81

(S)-3-{2-(4-Chlorophenylsulfonylamino)-4-[3-(1-phenylethyl)ureido]-phenoxy}phenylacetic acid (81) To a solution of 79 (60 mg, 0.14 mmol, 1.0 equiv.) in 0.4 mL of EtOAc, was added (S)-1-phenylethyl isocyanate (31 mg, 0.21 mmol, 1.5 equiv.). The mixture was stirred at room temperature for 14 h, and directly loaded onto silica gel column for purification. The product, 81, was a white solid (21 mg). $^1$H-NMR (400 MHz, DMSO-$d_6$): δ 12.33 (br s, 1H), 9.97 (br s, 1H), 8.49 (s, 1H), 7.64 (d, J=8 Hz, 2H), 7.46 (m, 3H), 7.35 (m, 4H), 7.17 (m, 1H), 7.15 (d, J=8.0 Hz, 1H), 7.11 (t, J=8 Hz, 1H), 6.91 (d, J=8.0 Hz, 1H), 6.68 (d, J=8 Hz, 1H), 6.54 (m, 2H), 6.36 (d, J=8 Hz, 1H), 4.80 (m, 1H), 3.49 (s, 2H), 1.38 (d, J=8 Hz, 3H); MS (ESI$^+$): 580.1 (M+H).

Example 82

3-[2-(4-Chlorophenylsulfonylamino)-4-propionylaminophenoxy]phenylacetic acid (82). To a solution of 79 (60 mg, 0.14 mmol, 1.0 equiv.) in 1.0 mL of EtOAc, was added propionic anhydride (27 mg, 0.21 mmol, 1.5 equiv.). The mixture was stirred at room temperature for 6 h, and directly loaded onto silica gel column for purification. The product, 82, was a white solid (38 mg). $^1$H-NMR (400 MHz, DMSO-$d_6$): δ 12.35 (br s, 1H), 10.05 (br s, 1H), 9.93 (s, 1H), 7.72 (s, 1H), 7.66 (d, J=8 Hz, 2H), 7.48 (d, J=8 Hz, 2H), 7.41 (d, J=8 Hz, 1H), 7.14 (t, J=8 Hz, 1H), 6.93 (d, J=8.0 Hz, 1H), 6.72 (d, J=8 Hz, 1H), 6.56 (s, 1H), 6.39 (d, J=8 Hz, 1H), 3.50 (s, 2H), 2.30 (q, J=6.7 Hz, 2H), 1.07 (t, J=6.7 Hz, 3H); MS (ESI$^+$): 489.2 (M+H).

Scheme 31

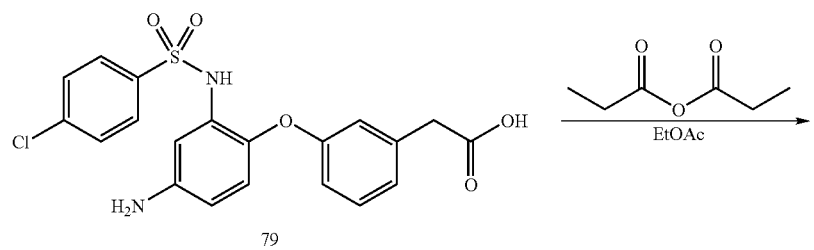

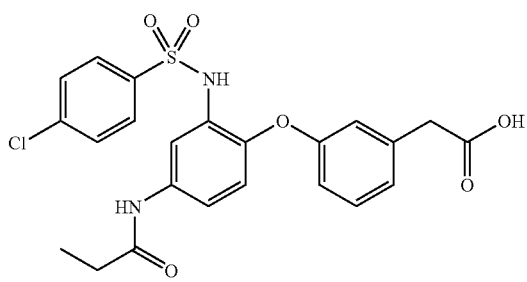

82

Examples 83 and 84

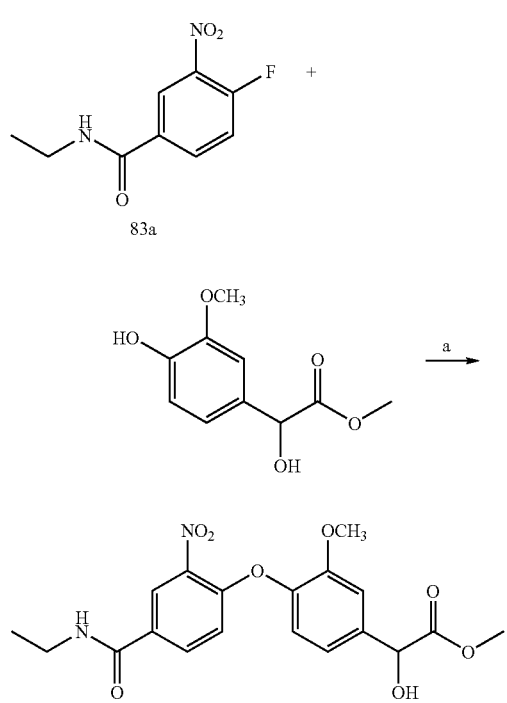

Scheme 32.

R = Cl, 83
R = OH, 84 a. K₂CO₃, DMSO, 60° C., overnight; b. Fe, AcOH, 60° C., 3 h; c. 3,4-Dichlorobenzenesulfonyl chloride, 2,6-lutidine, CH₂Cl₂, overnight; d. LiOH/THF, MeOH, and water, r.t., 2 h.

Example 83 was prepared according to Scheme 32. $^1$H NMR (CDCl$_3$) δ 7.94 (d, J=1.5 Hz, 1H), 7.88 (d, J=1.5 Hz, 1H), 7.56 (m, 2H), 7.46 (m, 2H), 7.08 (s, 1H), 6.99 (d, J=7.9 Hz, 1H), 6.66 (d, J=8.0 Hz, 1H), 6.57 (d, J=8.6 Hz, 1H), 6.27 (br s, 1H), 4.79 (s, 1H), 3.68 (s, 3H), 3.52 (m, 2H), 1.26 (t, J=7.2 Hz, 3H). MS (ESI$^+$) 583.0 [MH]$^+$.

Example 84 was prepared according to Scheme 32. $^1$H NMR (CDCl$_3$) δ 7.96 (d, J=2.1 Hz, 1H), 7.89 (d, J=2.1 Hz, 1H), 7.50 (m, 4H), 7.10 (s, 1H), 7.02 (m, 1H), 6.70 (d, J=8.2 Hz, 1H), 6.61 (d, J=8.6 Hz, 1H), 6.14 (br s, 1H), 5.26 (s, 1H), 3.73 (s, 3H), 3.52 (m, 2H), 1.23 (t, J=7.2 Hz, 3H). MS (ESI$^+$) 569.0 [MH]$^+$.

Example 85

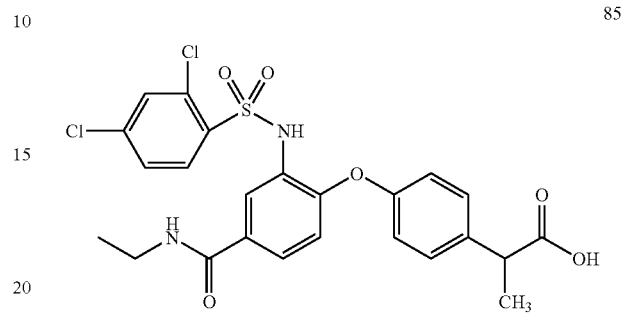

85

Example 85 was prepared from 2-(4-hydroxyphenyl)propionic acid methyl ester following the procedure described for 84. $^1$H NMR (DMSO-d$_6$) δ 12.15 (br s, 1H), 10.32 (s, 1H), 8.49 (br t, J=5.3 Hz, 1H), 7.91 (d, J=2.0 Hz, 1H), 7.79 (d, J=8.5 Hz, 1H), 7.67 (br d, J=9.5 Hz, 1H), 7.58 (d, J=2.0 Hz, 1H), 7.45 (dd, J=2.0, 8.5 Hz, 1H), 7.23 (d, J=8.6 Hz, 2H), 6.78 (d, J=8.6 Hz, 1H), 6.59 (d, J=8.5 Hz, 2H), 3.67 (q, J=7.1 Hz, 1H), 3.30 (m, 2H), 1.38 (d, J=7.1 Hz, 3H), 1.12 (t. J=7.2 Hz, 3H). MS (ESI$^+$) 537.1 [MH]$^+$.

Example 86

Scheme 33.

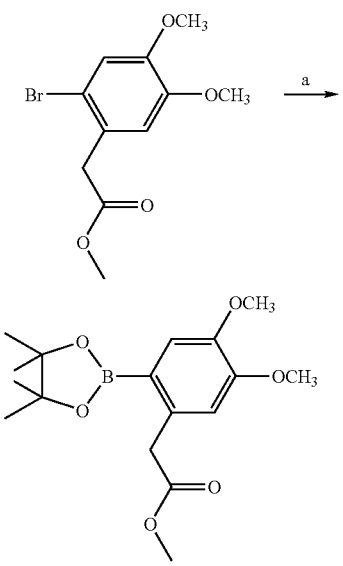

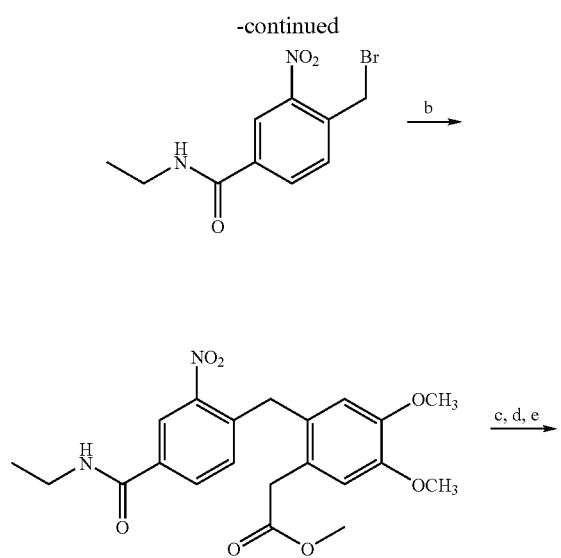
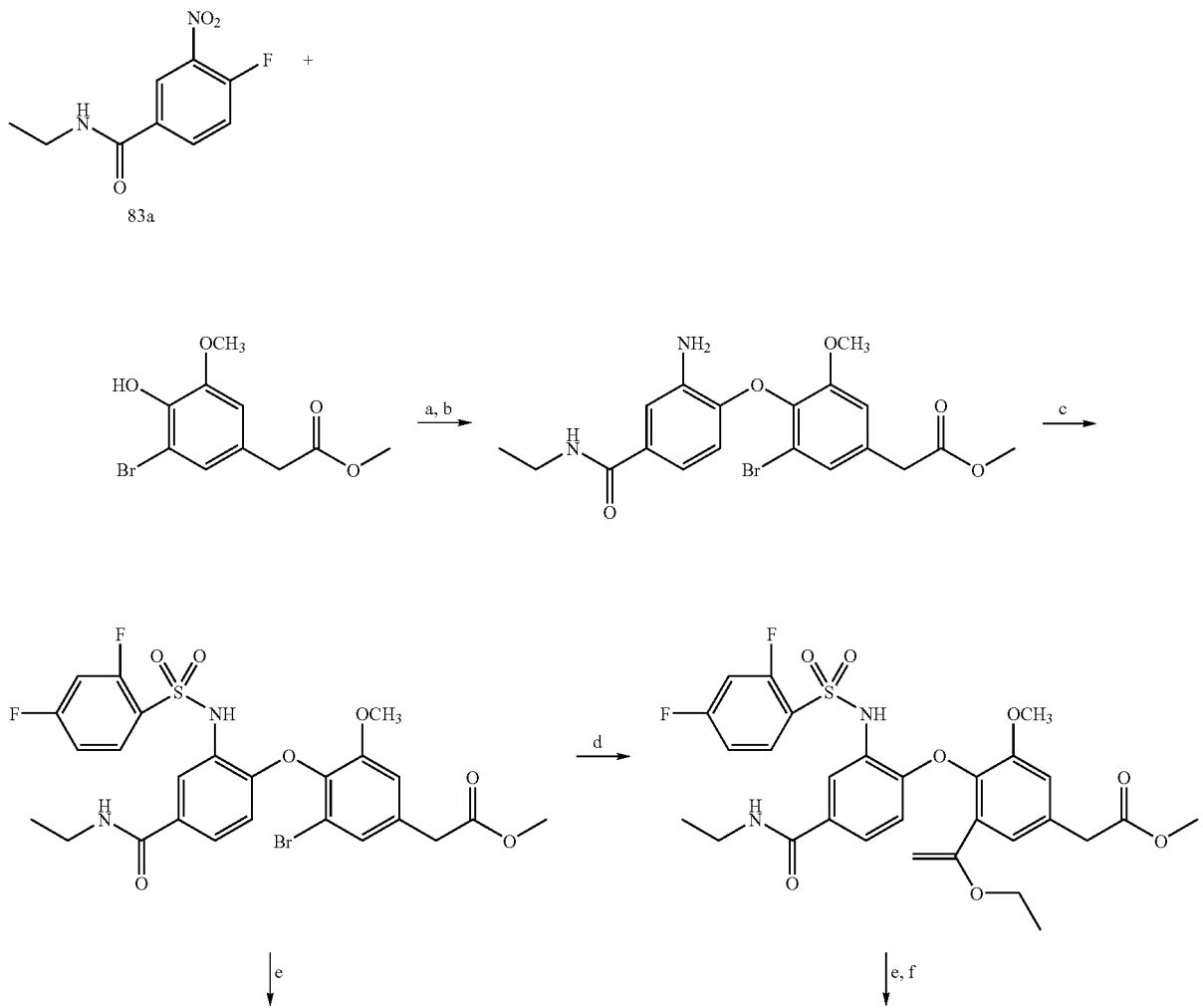
a. PdCl$_2$(dppf), KOAc, DMSO, 80° C., overnight; b. PdCl$_2$(dppf), K$_2$CO$_3$, DME, 80° C., overnight. c. Fe, AcOH, 60° C., 3 h; d. 4-Chlorobenzenesulfonyl chloride, 2,6-lutidine, CH$_2$Cl$_2$, overnight; e. LiOH/THF, MeOH, and water, r.t., 2 h.
Example 86 was prepared according to Scheme 33. $^1$H NMR (DMSO-d$_6$) δ 12.3 (br s, 1H), 8.38 (br s, 1H), 7.68 (m, 5H), 7.53 (m, 2H), 6.84 (s, 1H), 6.76 (d, J=7.8 Hz, 1H), 6.32 (s, 1H), 3.74 (s, 4H), 3.64 (s, 3H), 3.52 (s, 3H), 3.24 (m, 2H), 1.09 (t, J=7.2 Hz, 3H). MS (ESI$^+$) 547.0 [MH]$^+$.
Examples 87 and 88

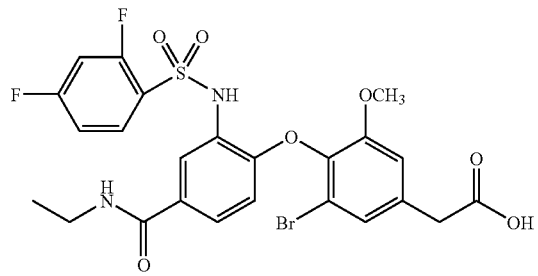
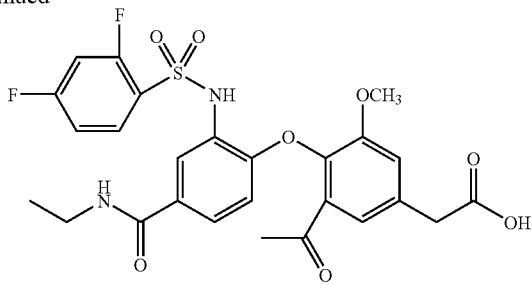

87

88 a. K$_2$CO$_3$, DMSO, 60° C., overnight; b. Fe, AcOH, 60° C., 3 h; c. 2,4-Difluorobenzenesulfonyl chloride, 2,6-lutidine, CH$_2$Cl$_2$, overnight; d. Pd(PPh$_3$)$_4$, tributyl(1-ethoxy vinyl)tin, toluene, reflux, 6 h; e. LiOH/THF, MeOH, and water, r.t., 2 h; f. 2N HCl, 5 minutes.

Example 87 was prepared according to Scheme 34. $^1$H NMR (CDCl$_3$) δ 7.93 (d, J=2.1 Hz, 1H), 7.87 (m, 1H), 7.59 (s, 1H), 7.50 (dd, J=2.2, 8.6 Hz, 1H), 7.16 (d, J=1.8 Hz, 1H), 6.93 (m, 2H), 6.87 (d, J=1.8 Hz, 1H), 6.42 (d, J=8.6 Hz, 1H), 6.28 (br t, J=5.6 Hz, 1H), 3.65 (s, 2H), 3.64 (s, 3H), 3.48 (m, 2H), 1.25 (t, J=7.2 Hz, 3H). MS (ESI$^+$) 599.0 [MH]$^+$.

Example 88 was prepared according to Scheme 34. $^1$H NMR (DMSO-d$_6$) δ 12.5 (br s, 1H), 10.37 (s, 1H), 8.42 (br t, J=5.5 Hz, 1H), 7.93 (d, J=1.6 Hz, 1H), 7.82 (m, 1H), 7.53 (br d, J=8.0 Hz, 1H), 7.44 (br t, J=8.8 Hz, 1H), 7.23 (s, 1H), 7.17 (m, 2H), 6.43 (d, J=8.5 Hz, 1H), 3.66 (s, 2H), 3.48 (s, 3H), 3.24 (m, 2H), 2.31 (s, 3H), 1.11 (t, J=7.2 Hz, 3H). MS (ESI$^+$) 563.0 [MH]$^+$.

Example 89

Scheme 35.

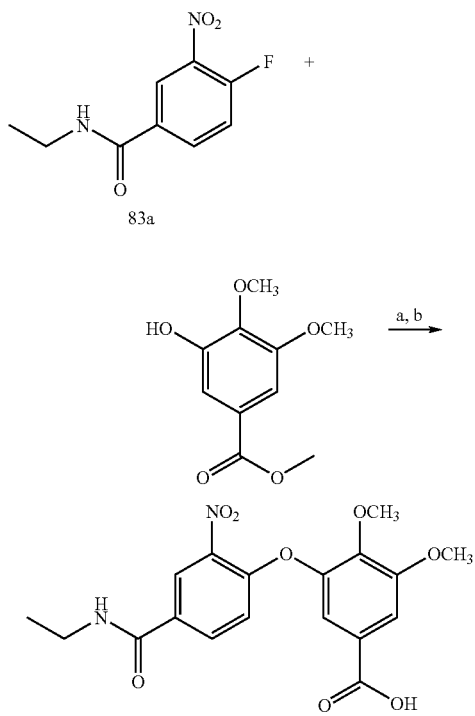

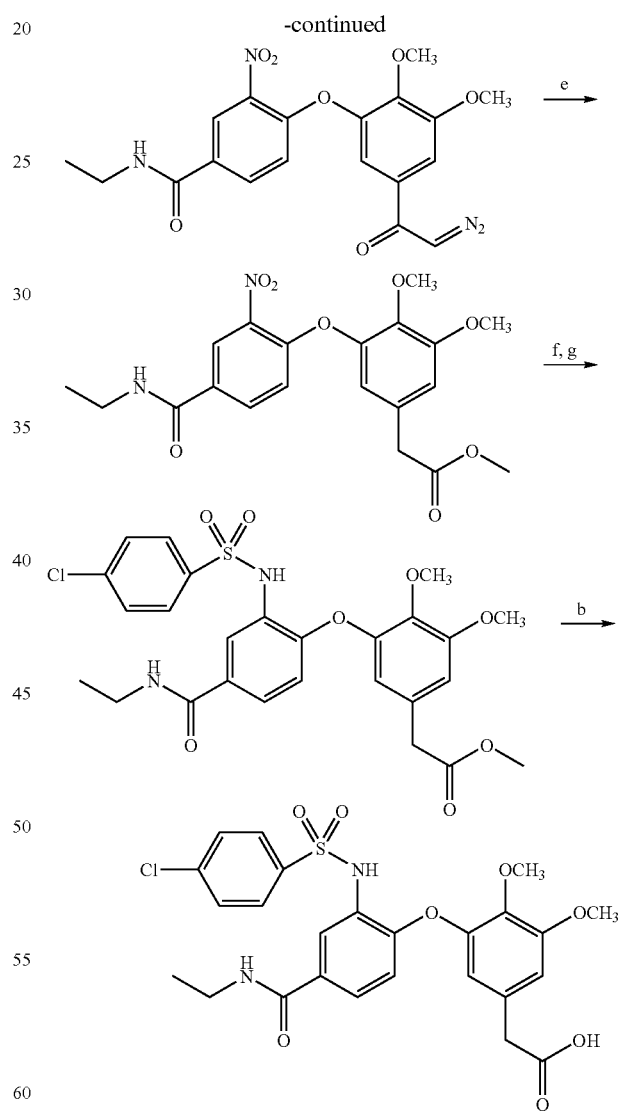

89 a. K$_2$CO$_3$, DMSO, 60° C., overnight; b. LiOH/THF, MeOH, and water, r.t., 2 h; c. thionyl chloride, 80° C., 6 h; d. TMSCHN2, TEA, THF/CH$_3$CN; e. silver benzoate, MeOH, r.t., 2 h; f. Fe, AcOH, 60° C., 3 h; g. 4-Chlorobenzenesulfonyl chloride, 2,6-lutidine, CH$_2$Cl$_2$, overnight.

Example 89 was prepared according to Scheme 35. $^1$H NMR (DMSO-d$_6$) δ 12.4 (br s, 1H), 10.26 (s, 1H), 8.43 (br t, J=5.5 Hz, 1H), 7.92 (d, J=2.1 Hz, 1H), 7.74 (d, J=8.6 Hz, 2H), 7.60 (d, J=8.6 Hz, 2H), 7.57 (dd, J=2.2, 8.6 Hz, 1H), 6.84 (d, J=1.7 Hz, 1H), 6.47 (d, J=8.6 Hz, 1H), 5.97 (d, J=1.7 Hz, 1H), 3.81 (s, 3H), 3.52 (s, 3H), 3.48 (s, 2H), 3.27 (m, 2H), 1.11 (t, J=7.2 Hz, 3H). MS (ESI$^+$) 549.0 [MH]$^+$.

Examples 90 and 91

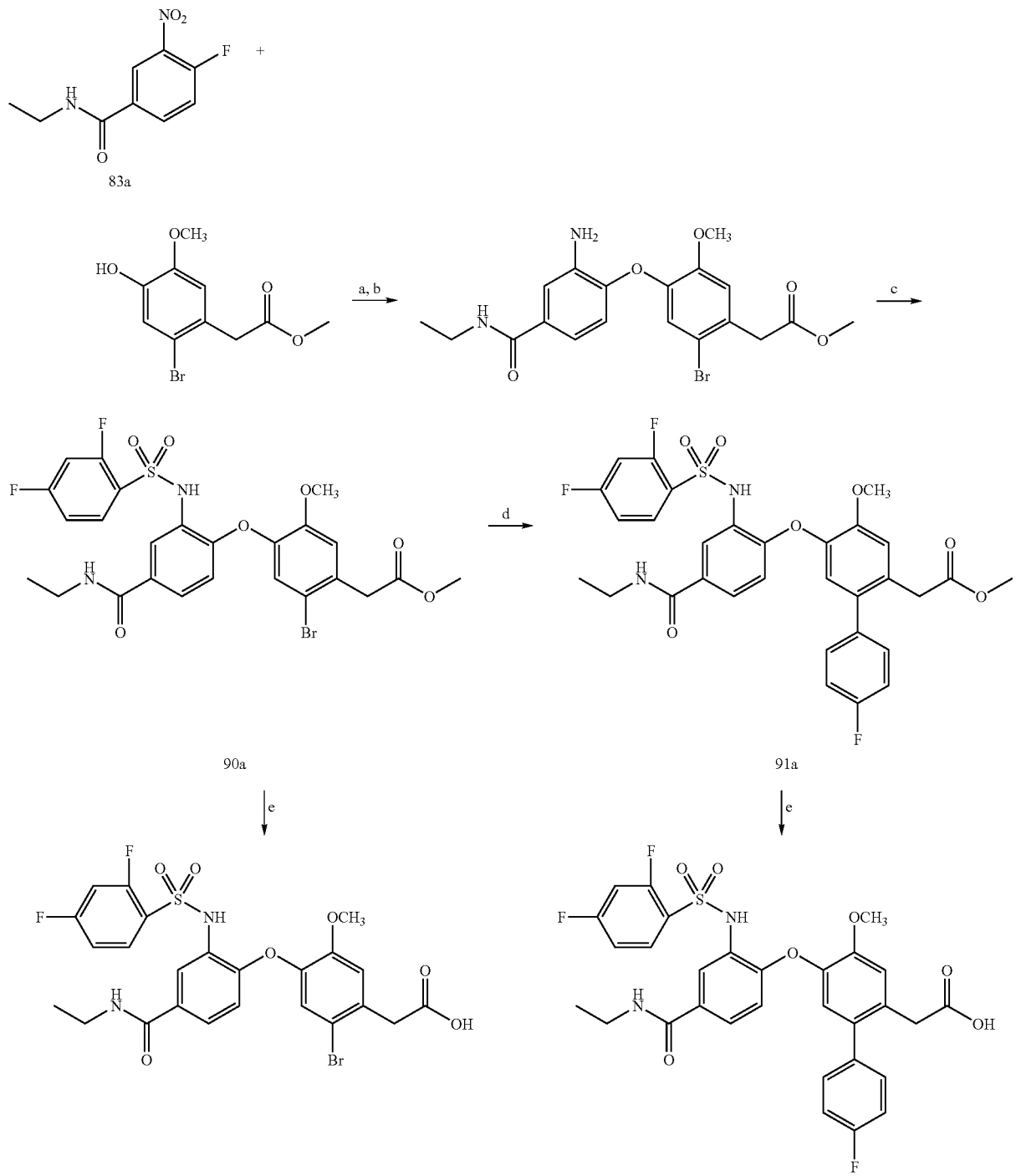

a. K$_2$CO$_3$, DMSO, 60° C., overnight; b. Fe, AcOH, 60° C., 3 h; c. 2,4-Difluorobenzenesulfonyl chloride, 2,6-lutidine, CH$_2$Cl$_2$, overnight; d. Pd(PPh$_3$)$_4$, 4-fluorophenylboronic acid, Na$_2$CO$_3$, DME, 85° C., 6 h; e. LiOH/THF, MeOH, and water, r.t., 2 h.

Example 90 was prepared according to Scheme 36 $^1$H NMR (DMSO-d$_6$) δ 12.5 (br s, 1H), 10.75 (s, 1H), 8.47 (br s, 1H), 7.89 (d, 1H), 7.72 (m, 1H), 7.62 (m, 1H), 7.44 (m, 1H), 7.26 (s, 1H), 7.17 (m, 1H), 6.66 (s, 1H), 6.50 (d, J=8.8 Hz, 1H), 3.72 (s, 2H), 3.66 (s, 3H), 3.25 (m, 2H), 1.12 (t, J=7.2 Hz, 3H). MS (ESI$^+$) 599.0 [MH]$^+$.

Example 91 was prepared according to Scheme 36 $^1$H NMR (DMSO-d$_6$) δ 12.5 (br s, 1H), 10.36 (s, 1H), 8.46 (br s, 1H), 7.89 (m, 1H), 7.71 (m, 1H), 7.61 (br d, J=7.5 Hz, 1H), 7.41 (m, 1H), 7.27 (m, 4H), 7.19 (s, 1H), 6.99 (t, J=8.9 Hz, 1H), 6.66 (s, 1H), 6.51 (dd, J=2.0, 8.6 Hz, 1H), 3.70 (s, 2H), 3.66 (s, 3H), 3.27 (m, 2H), 1.10 (t, J=7.2 Hz, 3H). MS (ESI$^+$) 615.0 [MH]$^+$.

Examples 92-94

Scheme 37
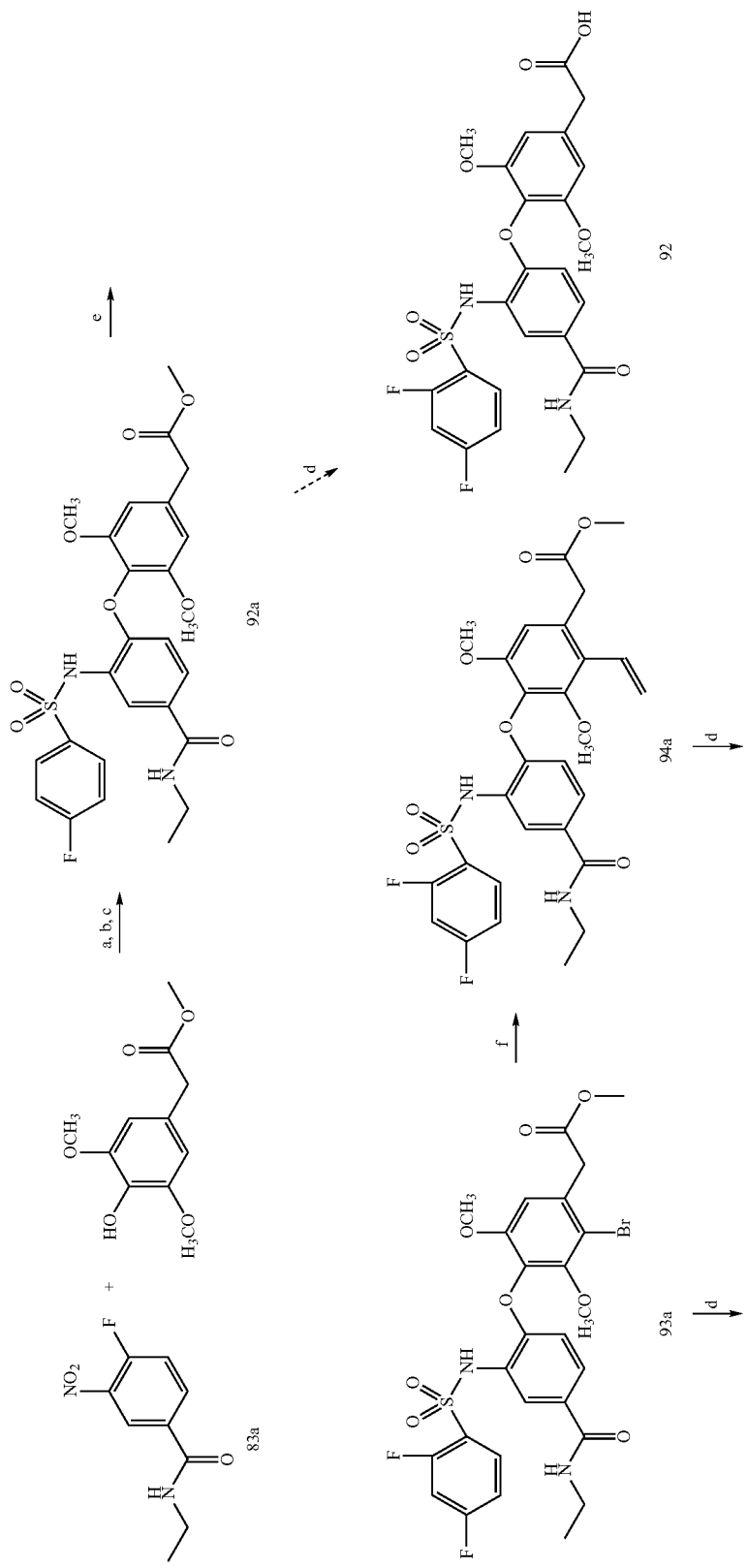

-continued
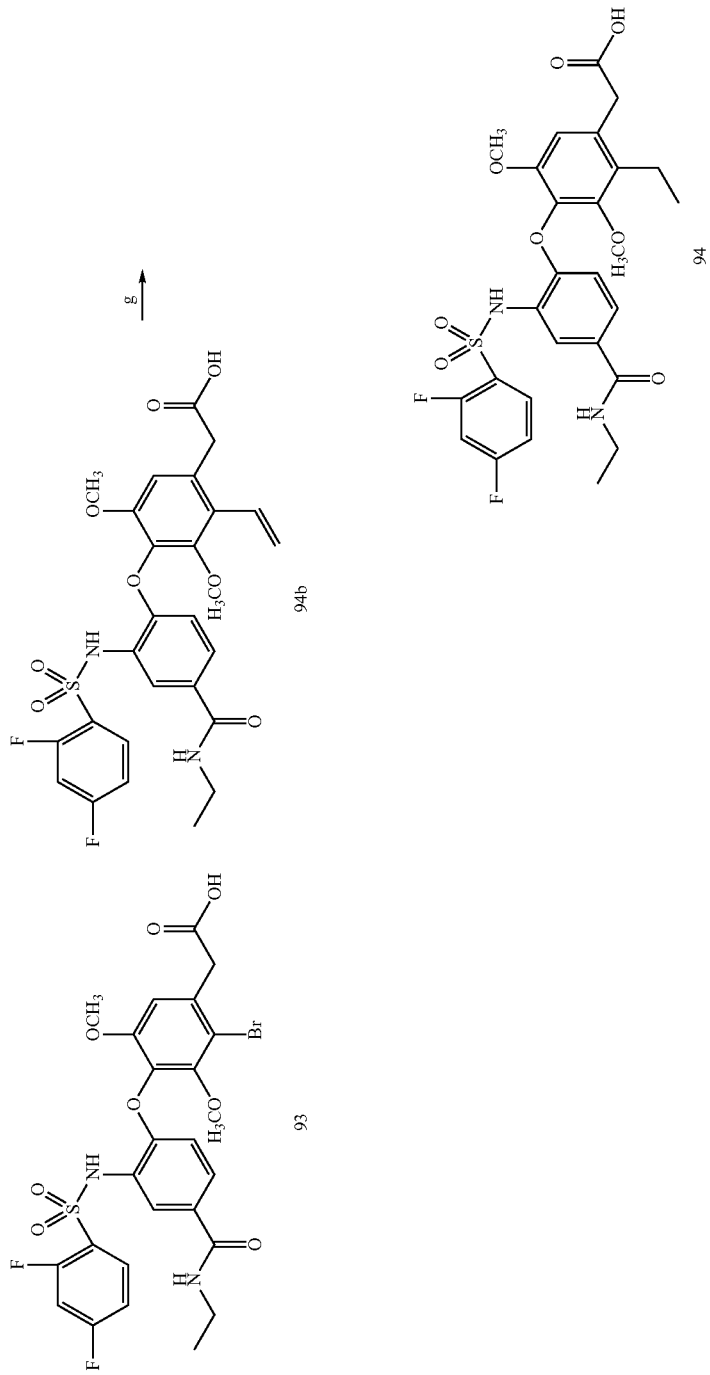
a. $K_2CO_3$, DMSO, 60° C., overnight; b. Fe, AcOH, 60° C., 3 h; c. 2,4-Difluorobenzenesulfonyl chloride, 2,6-lutidine, $CH_2Cl_2$, overnight; d. LiOH/THF, MeOH, and water, r.t., 2 h; e. $Br_2$, AcOH, r.t., overnight; f. $Pd(PPh_3)_4$, tributyl(vinyl)tin, toluene, reflux, 6 h; g. $H_2$, Pd/C, EtOH, r.t., 2 h.

Example 92 was prepared according to Scheme 37. $^1$H NMR (DMSO-d$_6$) δ 12.4 (br s, 1H), 10.20 (s, 1H), 8.37 (br t, J=5.5 Hz, 1H), 7.89 (d, J=2.1 Hz, 1H), 7.81 (m, 1H), 7.48 (m, 2H), 7.18 (dt, J=2.0, 8.6 Hz, 1H), 6.68 (s, 2H), 6.26 (d, J=8.6 Hz, 1H), 3.58 (s, 8H), 3.25 (m, 2H), 1.11 (t, J=7.2 Hz, 3H). MS (ESI$^+$) 551.1 [MH]$^+$.

Example 93 was prepared according to Scheme 37. $^1$H NMR (DMSO-d$_6$) δ 12.5 (br s, 1H), 10.41 (s, 1H), 8.41 (br t, J=5.5 Hz, 1H), 7.89 (d, J=2.1 Hz, 1H), 7.83 (m, 1H), 7.52 (m, 2H), 7.21 (dt, J=1.8, 8.6 Hz, 1H), 7.05 (s, 1H), 6.34 (d, J=8.6 Hz, 1H), 3.76 (s, 2H), 3.63 (s, 3H), 3.53 (s, 3H), 3.25 (m, 2H), 1.10 (t, J=7.2 Hz, 3H). MS (ESI+) 629.0 [MH]$^+$.

Compound 94b. $^1$H NMR (DMSO-d$_6$) δ 12.5 (br s, 1H), 10.34 (s, 1H), 8.39 (br t, J=5.2 Hz, 1H), 7.88 (d, J=2.0 Hz, 1H), 7.84 (m, 1H), 7.52 (m, 2H), 7.21 (m, 1H), 6.85 (s, 1H), 6.61 (dd, J=11.8, 17.9 Hz, 1H), 6.34 (d, J=8.6 Hz, 1H), 5.55 (dd, J=2.0, 17.9 Hz, 1H), 5.45 (dd, J=2.0, 11.8 Hz, 1H), 3.68 (s, 2H), 3.54 (s, 3H), 3.53 (s, 3H), 3.24 (m, 2H), 1.10 (t, J=7.2 Hz, 3H). MS (ESI$^+$) 577.0 [MH]$^+$.

Example 94 was prepared according to Scheme 37. $^1$H NMR (DMSO-d$_6$) δ 12.4 (br s, 1H), 10.32 (s, 1H), 8.38 (br s, 1H), 7.88 (d, J=2.0 Hz, 1H), 7.84 (m, 2H), 7.50 (m, 2H), 7.21 (m, 1H), 6.76 (s, 1H), 6.31 (d, J=8.6 Hz, 1H), 3.61 (s, 2H), 3.60 (s, 3H), 3.50 (s, 3H), 3.37 (m, 2H), 3.25 (m, 2H), 1.10 (t, J=7.2 Hz, 3H), 1.04 (t, J=7.2 Hz, 3H). MS (ESI$^+$) 579.2 [MH]$^+$.

Example 95

Human CRTH2 Binding Assay

Full-length human CRTH2 cDNA was generated by polymerase chain reaction (PCR) using human genomic DNA as template and subsequently cloned into pCDNA3.1(+) (Invitrogen), generating a CRTH2 expression plasmid pHLT124. The plasmid was transfected into 293 cells, which normally express CRTH2, using LipofectAMINE™ reagents (Gibco/BRL). G418 (800 mg/mL) was added to the culture 48 h after transfection and cells were maintained under selection for 3 weeks to ensure that all surviving cells stably expressed CRTH2. These cells are labeled as 293(124) hereafter.

$^3$H-PGD$_2$ binding assay was performed using 293(124) cells. In brief, cells were washed and suspended in RPMI containing 0.5% BSA and 20 mM HEPES. Each assay contained 25,000 cells, appropriate amount of test compound when necessary and a mixture of 1 nM $^3$H-PGD$_2$ (Anmersham Pharmacia Biotech) and 30 nM of unlabeled PGD$_2$ (Cayman Chemicals) in 200 mL final volume. The cell mixture was incubated at room temperature for 2.5 h with shaking and the cells were separated from free $^3$H-PGD$_2$ and transferred onto a filter plate using a cell harvester. Radioactivity bound to the cells was measured on a liquid scintillation counter. Nonspecific binding was determined in the presence of 10 mM of unlabeled PGD$_2$.

Modulation of CRTH2 and/or one or more other PGD$_2$ receptors by test compounds can be assessed by other in vitro and in vivo assays. Examples of such assays include measuring second messenger (e.g., cAMP, IP$_3$ or Ca$^{2+}$) levels, ion flux, phosphorylation levels, transcription levels, and the like. Recombinant or naturally occurring CRTH2 polypeptides and/or other PGD$_2$ receptor peptides can be used and the protein can be isolated, expressed in a cell, expressed in a membrane derived from a cell, expressed in tissue or in an animal. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and/or cytoplasmic domain of a receptor. Gene amplification can also be examined. Furthermore, ligand-binding domains of the protein of interest can be used in vitro in soluble or solid state reactions to assay for ligand binding.

CRTH2-G-protein or another PGD$_2$ receptor-G-protein interactions can also be examined, by, for example, analysis of binding of the G-protein to the receptor or its release from the receptor.

Exemplary compounds of the invention displayed IC$_{50}$ values as shown in Table I in the above-described ligand binding assay.

TABLE I

Example of CRTH2 activity.

| Example # | CRTH2 Binding IC50 |
| --- | --- |
| 1 | ++ |
| 2 | ++ |
| 3 | ++ |
| 4 | + |
| 5 | ++ |
| 10 | +++ |
| 12 | +++ |
| 17 | ++ |
| 18 | +++ |
| 31 | + |
| 33 | ++ |
| 35 | +++ |
| 36 | ++ |
| 63 | ++ |
| 64 | +++ |
| 67 | +++ |
| 70 | +++ |
| 73 | +++ |
| 75 | +++ |
| 77 | ++ |

+ IC50 > 15 μM
++ 15 μM > IC50 > 1 μM
+++ IC50 < 1 μM

Example 96

Cyclic AMP Assays on Human DP Function

Cyclic AMP assays on human DP function are performed using human platelets (AllCells, Berkeley, Calif.) and the 96-well Tropix cAMP ELISA System (Applied Biosystems) following the manufacturer's manual. Briefly, the human platelets rich plasma (PRP) is diluted 1:3 with human plasma and incubated with 1 mM of the phosphodiesterases inhibitor 3-isobutyl-1-methylxanthine (IBMX, Sigma) at 37° C. for 20 min, to prevent hydrolysis of cAMP. 20 μl of the above PRP sample is mixed 1:1:1 with the test compound and PGD$_2$ (both prepared in the assay buffer with DMSO concentration<1%) in a 96-well plate. The assay buffer can be OPTI-free medium (Gibco BRL). After 20 min incubation at 37° C., 20 μl of lysis buffer from the kit is added to each well of the mixture and the plate then incubated at room temperature for 10 min with moderate shaking and at 37° C. for 10 min. After the cell lysis, 60 μl of the cell lysate together with 30 μl of diluted cAMP-AP conjugate and 60 μl anti-cAMP antibody is then transferred into a kit assay plate and the plate incubated at room temperature for 30 min with shaking. The plate is then washed with wash buffer and incubated with 100 μl per well of substrate/enhancer solution at room temperature for 60 min. Light signal intensity, which is inversely proportional to the cAMP level in each sample, is measured in a luminometer (CLIPR, Dynamic Devices). The final human plasma concentration in the assay described above is about 33%. The assays are also performed using washed platelets (prepared by centrifuging the PRP at 2000 rpm for 15 min and resuspending the platelets in the assay buffer), or in the presence of higher than about 33% of human plasma by also preparing the test compound and/or $PGD_2$ solution in human plasma.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a respiratory allergic disease or a disease or condition selected from group consisting of asthma, allergic rhinitis, eczema, psoriasis, atopic dermatitis, rheumatoid arthritis, inflammatory bowel disease, Crohn's disease, ulcerative colitis, chronic obstructive pulmonary disease, conjunctivitis, nasal congestion and urticaria, comprising administering to a subject in need thereof a therapeutically effective amount of a compound of formula (XVI):

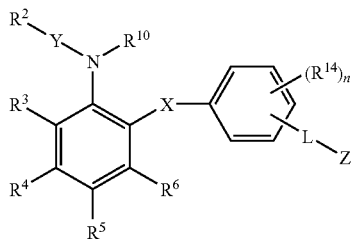

XVI or a pharmaceutically acceptable salt thereof, wherein
Y is —$S(O)_2$—;
X is —O—;
$R^2$ is a substituted or unsubstituted benzene ring;
$R^3$ and $R^5$ are independently selected from the group consisting of hydrogen, halogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —NR'R", —OR', —$NO_2$, —CN, —C(O)R', —$CO_2$R', —C(O)NR'R", —($C_1$-$C_4$)alkylene-C(O)NR'R", —$S(O)_m$R', —$S(O)_k$NR'R", —OC(O)OR', —OC(O)R', —OC(O)NR'R", —N(R''')C(O)NR'R", —N(R")C(O)R' and —N(R")C(O)OR';
$R^4$ is selected from the group consisting of —NHC(O)-cyclo($C_5$-$C_7$)alkyl, —C(O)$NR^{12}R^{13}$ and —NHC(O)-alkyl;
$R^6$ is selected from the group consisting of hydrogen, halogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —NR'R", —$NO_2$, —CN, —C(O)R', —$CO_2$R', —C(O)NR'R", —($C_1$-$C_4$)alkylene-C(O)NR'R", —$S(O)_m$R', —$S(O)_k$NR'R", —OC(O)OR', —OC(O)R', —OC(O)NR'R", —N(R''')C(O)NR'R", —N(R")C(O)R' and —N(R")C(O)OR';

$R^{10}$ is selected from the group consisting of hydrogen, ($C_1$-$C_8$)alkyl, fluoro($C_1$-$C_4$)alkyl, hetero($C_2$-$C_8$)alkyl, aryl, heteroaryl, aryl($C_1$-$C_4$)alkyl, —C(O)R', —$CO_2$R', —C(O)NR'R", —$S(O)_m$R' and —$S(O)_k$NR'R";
L is a divalent linkage selected from the group consisting of a single bond, ($C_1$-$C_6$)alkylene and ($C_2$-$C_4$)heteroalkylene;
Z is —$CO_2R^{12}$;
$R^{12}$ and $R^{13}$ are independently selected from the group consisting of hydrogen, ($C_1$-$C_8$)alkyl, hetero($C_2$-$C_8$)alkyl, aryl, aryl($C_1$-$C_4$)alkyl and heteroaryl;
each $R^{14}$ is independently selected from the group consisting of halogen, ($C_1$-$C_8$)alkyl, fluoro($C_1$-$C_4$)alkyl, —OR', —NR'R", —$NO_2$, —CN, —C(O)R' and aryl;
each R', R" and R''' is independently selected from the group consisting of hydrogen, ($C_1$-$C_6$)alkyl, cyclo($C_3$-$C_8$)alkyl, aryl and aryl($C_1$-$C_4$)alkyl;
each subscript k is independently 0, 1 or 2;
each subscript m is independently 0, 1, 2 or 3; and
the subscript n is 0, 1, 2, 3 or 4.

2. The method of claim 1, wherein the subject has allergic rhinitis.

3. The method of claim 2, wherein the subject has asthma.

4. The method of claim 1, wherein $R^4$ is —NHC(O)-cyclo($C_5$-$C_7$)alkyl.

5. The method of claim 1, wherein $R^2$ is a substituted benzene ring and at least one substituent on the benzene ring is selected from the group consisting of halogen, —$OCF_3$, —$OCH_3$, —($C_1$-$C_5$)alkyl, —CN, and —$NO_2$.

6. The method of claim 1, wherein $R^{10}$ is hydrogen.

7. The method of claim 6, wherein $R^4$ is —C(O)NH—($C_1$-$C_4$)alkyl, and $R^6$ is hydrogen.

8. The method of claim 7, wherein $R^2$ is a benzene ring substituted with 1, 2, or 3 chlorine atoms.

9. The method of claim 1, wherein -L-Z taken together are —$CH_2$COOH.

10. The method of claim 9, wherein the subscript n is 1 or 2.

11. The method of claim 10, wherein $R^{14}$ is —$OCH_2CH_3$ or —$OCH_3$.

12. The method of claim 1, wherein $R^3$, $R^5$ and $R^6$ are each hydrogen.

13. The method of claim 1, wherein the compound has the formula (XVIII):

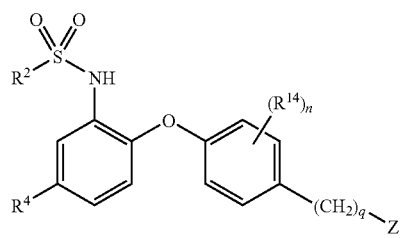

XVIII wherein $R^4$ is —C(O)NH—($C_1$-$C_4$)alkyl; and the subscript q is 0, 1, 2, 3, 4, 5 or 6.

14. The method of claim 1, wherein the compound is selected from the group consisting of

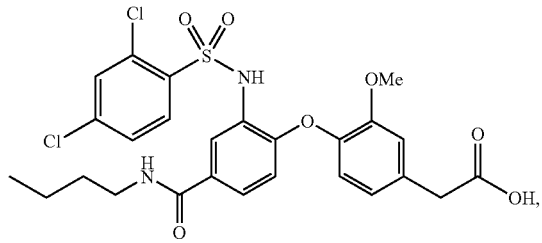

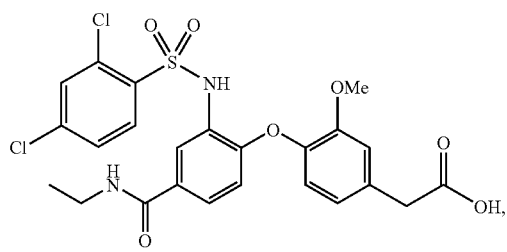

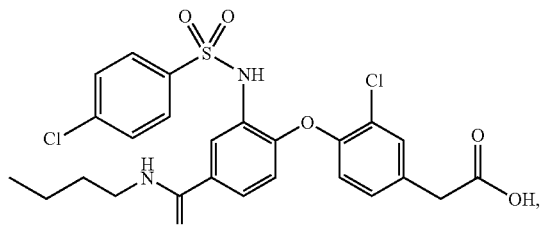

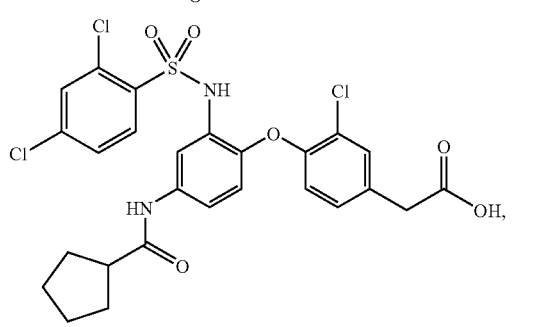 and

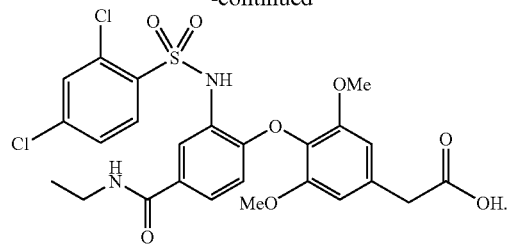

15. The method of claim 1, wherein the compound is

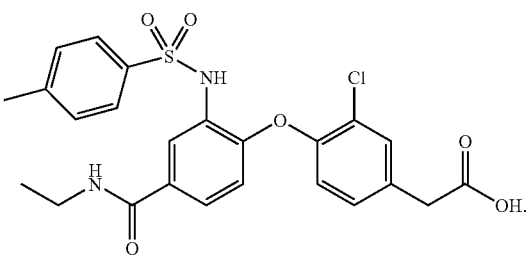

16. The method of claim 1, wherein $R^6$ in the formula (XVI) is hydrogen.

17. The method of claim 1, wherein the subject has eczema, psoriasis or urticaria.

18. The method of claim 1, wherein the subject has atopic dermatitis.

19. The method of claim 1, wherein the subject has rheumatoid arthritis.

20. The method of claim 1, wherein the subject has inflammatory bowel disease, Crohn's disease or ulcerative colitis.

21. The method of claim 1, wherein the subject has chronic obstructive pulmonary disease.

22. The method of claim 1, wherein the subject has conjunctivitis.

23. The method of claim 1, wherein the subject has nasal congestion.

24. A method as in any one of claims 2, 3, 21 and 23, wherein said compound is administered orally, parenterally or topically.

* * * * *